(12) United States Patent
Heemskerk et al.

(10) Patent No.: US 8,110,681 B2
(45) Date of Patent: Feb. 7, 2012

(54) COMPOUNDS FOR THE TREATMENT OF SPINAL MUSCULAR ATROPHY AND OTHER USES

(75) Inventors: Jill Heemskerk, Bethesda, MD (US); Keith D. Barnes, Rexford, NY (US); John M. McCall, Boca Grande, FL (US); Graham Johnson, Madison, CT (US); David Fairfax, Slingerlands, NY (US); Matthew Robert Johnson, Morrisville, NC (US)

(73) Assignees: The United States of America as represented by the Secretary, Department of Health and Human Services, Washington, DC (US); Albany Molecular Research, Inc., Albany, NY (US); Science Applications International Inc. (SAIC), San Diego, CA (US)

(*) Notice: Subject to any disclaimer, the term of this patent is extended or adjusted under 35 U.S.C. 154(b) by 210 days.

(21) Appl. No.: 12/293,268

(22) PCT Filed: Mar. 13, 2007

(86) PCT No.: PCT/US2007/006772
§ 371 (c)(1),
(2), (4) Date: Dec. 30, 2008

(87) PCT Pub. No.: WO2007/109211
PCT Pub. Date: Sep. 27, 2007

(65) Prior Publication Data
US 2009/0312323 A1 Dec. 17, 2009

Related U.S. Application Data

(60) Provisional application No. 60/783,292, filed on Mar. 17, 2006.

(51) Int. Cl.
*C07D 413/04* (2006.01)
*C07D 239/24* (2006.01)
*C07D 401/04* (2006.01)
*C07D 209/46* (2006.01)
*C07D 206/56* (2006.01)
*A61K 31/535* (2006.01)
*A61K 31/44* (2006.01)
*A61K 31/40* (2006.01)
*A01N 43/54* (2006.01)

(52) U.S. Cl. .............. 544/144; 544/242; 546/277.1; 548/472; 548/450; 514/235.2; 514/256; 514/339; 514/414; 514/416

(58) Field of Classification Search .............. None
See application file for complete search history.

(56) References Cited

U.S. PATENT DOCUMENTS

| | | | |
|---|---|---|---|
| 3,542,806 | A | 11/1970 | Helsley et al. |
| 3,997,669 | A | 12/1976 | Carney et al. |
| 4,126,691 | A | 11/1978 | Carney et al. |
| 5,026,856 | A | 6/1991 | Yatsunami et al. |
| 5,567,718 | A | 10/1996 | Shutske et al. |
| 5,595,872 | A | 1/1997 | Wetterau, II et al. |
| 5,739,135 | A | 4/1998 | Biller et al. |
| 5,789,197 | A | 8/1998 | Wetterau, II et al. |
| 5,869,502 | A | 2/1999 | Shutske et al. |
| 5,869,685 | A | 2/1999 | Shutske et al. |
| 5,874,458 | A | 2/1999 | Shutske et al. |
| 5,874,583 | A | 2/1999 | Shutske et al. |
| 6,339,093 | B1 | 1/2002 | Alanine et al. |
| 6,492,365 | B1 | 12/2002 | Wetterau, II et al. |
| 2003/0166590 | A1 | 9/2003 | Wetterau, II et al. |
| 2004/0044063 | A1 | 3/2004 | Stockwell et al. |
| 2005/0054670 | A1 | 3/2005 | Tegley et al. |

FOREIGN PATENT DOCUMENTS

| | | |
|---|---|---|
| DE | 20 34 240 A1 | 1/1971 |
| GB | 1256931 | 3/1969 |
| JP | 56044686 A | 4/1981 |
| JP | 56045955 A | 4/1981 |

(Continued)

OTHER PUBLICATIONS

Jones et al., Prostaglandins, Leukotrienes and Essential Fatty Acids 72 (2005) 289-299.*
Wilson et al, British Journal of Pharmacology (2006) 148, pp. 326-339.*
Tonami et al. Advances in Mass Spectrometry (1980), 8B, pp. 1274-1279.*
Kapples et al., *J. Heterocyclic Chem.*, 34, 1335-1338 (1997).
Lawrence et al., *J. Org. Chem.*, 67 (2), 457-464 (2002).

(Continued)

*Primary Examiner* — Kamal Saeed
*Assistant Examiner* — Nyeemah A Grazier
(74) *Attorney, Agent, or Firm* — Leydig, Voit & Mayer, Ltd.

(57) ABSTRACT

Compounds of Formula (I) or (II) useful for the treatment of spinal muscular atrophy or other uses, as well as methods of using such compounds to increase SMN expression, increase EAAT2 expression, or increase the expression of a nucleic acid that encodes a translational stop codon introduced by mutation or frameshift.

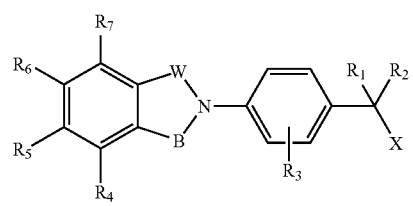

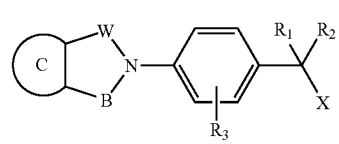

15 Claims, No Drawings

FOREIGN PATENT DOCUMENTS

| | | |
|---|---|---|
| JP | 58045088 A | 3/1983 |
| JP | 03181478 A | 8/1991 |
| WO | WO 00/39114 A2 | 7/2000 |
| WO | WO 02/46164 A1 | 6/2002 |
| WO | WO 02/064564 A1 | 8/2002 |
| WO | WO 2004/009558 A2 | 1/2004 |
| WO | WO 2004/036181 A2 | 4/2004 |
| WO | WO 2004/048332 A1 | 5/2004 |
| WO | WO 2005/021532 A1 | 3/2005 |
| WO | WO 2006/050451 A2 | 5/2006 |
| WO | 2007088189 A1 | 8/2007 |
| WO | WO 2008/045905 A1 | 4/2008 |

OTHER PUBLICATIONS

Lunn et al., *Chem. & Biol.*, 11 (11), 1489-1493 (2004).
MacKinnon et al., *British J. Pharmacology*, 116, 1729-1736 (1995).
Nannini et al., *Arzneimittel-Forsch.* (*Drug Res.*), 23 (8), 1090-1100 (1973).
Nishio et al., *J. Org. Chem.*, 57 (14), 4000-4005 (1992).
Wolstencroft et al., *Hum. Mol. Genet.*, 14 (9), 1199-1210 (2005).
International Preliminary Report on Patentability, Application No. PCT/US2007/006772, dated Sep. 23, 2008.
European Patent Office Communication pursuant to Article 94(3) EPC, Application No. 07 753 404.8-2101; dated Mar. 6, 2009.
European Patent Office Communication pursuant to Article 94(3) EPC, Application No. 07 753 404.8-2101; dated May 11, 2010.
Australian Patent Office, Examination Report in Australian Patent Application No. 2007227398 (Aug. 29, 2011).
CAplus Accession No. 1994:117 (RN 151060-65 0).
Grubb et al., "Excretion balance and urinary metabolites of the S-enantiomer of indobufen in rats and mice," *Biochemical Pharmacology*, 46(8), 1507-1510 (1993).

\* cited by examiner

COMPOUNDS FOR THE TREATMENT OF SPINAL MUSCULAR ATROPHY AND OTHER USES

CROSS-REFERENCE TO RELATED APPLICATIONS

This patent application is the national phase application of PCT/US2007/006772 and claims the benefit of U.S. Provisional Patent Application No. 60/783,292, filed Mar. 17, 2006, which is incorporated by reference.

BACKGROUND OF THE INVENTION

Spinal Muscular Atrophy (SMA) is a paralyzing and often fatal disease of infants and children. To date there is no effective treatment for SMA. This disease is caused by mutations that reduce the level of survival motor neuron protein (SMN), resulting in the loss of motor neurons in the central nervous system. Drugs that increase SMN expression are expected to be useful in the prevention and treatment of SMA. Prior studies in cultured cells have shown that indoprofen, a previously marketed non-steroidal anti-inflammatory drug (NSAID), increases the level of expression of SMN protein via an unknown mechanism (Lunn et al., *Chem. & Biol.*, 11, 1489-1493(2004)). Indoprofen also was shown to increase survival of SMA model mouse fetuses when administered in utero. The mechanism of regulation of SMN expression is not thought to be related to indoprofen's NSAID activity since not all of the NSAIDs tested increase SMN expression. One possible mechanism of action is increased protein translation, as it has been shown that the level of the SMN protein can be improved by drugs that cause translational read-through of nonsense stop codons (Wolstencroft et al., *Hum. Mol. Genet.*, 14, 1199-210 (2005)). However, indoprofen is not a useful drug for SMA because it is only weakly active in increasing SMN expression, does not enter the brain at sufficient levels, and has lethal side effects due, at least in part, to its cyclooxygenase (Cox) inhibitory activity.

Accordingly, there is a need for new compounds, compositions, and methods that can address some of these problems.

BRIEF SUMMARY OF THE INVENTION

The invention provides compounds of Formula I or II:

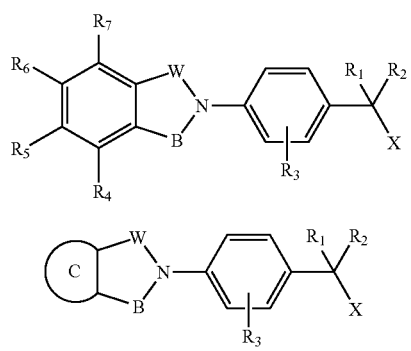

The invention also provides related compounds, as well as methods for making the compounds of the invention, and compositions, especially pharmaceutical compositions, comprising one or more compounds of the invention and a carrier.

The invention further provides a method of increasing SMN expression in a cell comprising administering a compound of the invention to a cell comprising a nucleic acid encoding SMN2, whereby expression of SMN is increased.

The invention additionally provides a method of increasing the expression of excitatory amino acid transporter (EAAT2) in a cell comprising administering a compound of the invention to a cell comprising a nucleic acid that encodes EAAT2, whereby expression of EAAT2 is increased.

Also provided by the invention is a method of increasing in a cell the expression of a nucleic acid that encodes a translational stop codon, the method comprising administering a compound of the invention to a cell comprising a nucleic acid that encodes a translational stop codon, whereby expression of the nucleic acid is increased.

DETAILED DESCRIPTION OF THE INVENTION

The invention provides compounds of Formula I or II:

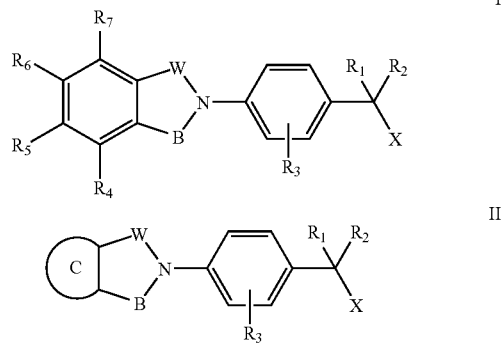

wherein,

W is selected from the group consisting of C(O), C(S), and $CH_2$;

B is $CH_2$ or $CH(C_nH_{2n+1})$, wherein n is an integer of 1 to 8;

C is selected from the group consisting of a fused thiophene ring, a fused pyridine ring, and a cyclohexane ring, any of which can be saturated or contain one or two non-conjugated double bonds;

$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;

$R_3$ is selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy;

$R_4$, $R_5$, $R_6$ and $R_7$ are independently selected from the group consisting of H, hydroxyl, halogen, CN, $NO_2$, sulfonamide, $C_1$-$C_8$ alkyl, $C_3$-$C_6$ cycloalkyl, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ dialkyl amino, $C_1$-$C_4$ alkylamino, $C_3$-$C_6$ cycloalkyl amino, morpholine, heteroaryl (including without limitation thienyl, pyridyl and pyrimidinyl), arylamino, arylalkylamino, phenyl, C(O)R', NR'(COR''), NR'$SO_2$R'' and NR'(CONR''R'''), wherein in R', R'' and R''' are independently H, $C_1$-$C_6$ alkyl, phenyl, or substituted phenyl, and wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine, and the phenyl is optionally substituted with one or more members selected from the group consisting of halogen, $NO_2$, CN, $C_1$-$C_1$ alkyl, $C_1$-$C_4$ haloalkyl, and $C_1$-$C_4$ alkoxy, or $R_4$ and $R_5$, $R_5$ and $R_6$, or $R_6$ and $R_7$, taken together with the carbon to which they are attached, form a ring;

X is selected from the group consisting of

H;

CN;

$C(O)OR_8$, wherein $R_8$ is H or $C_1$-$C_8$ alkyl, and the alkyl optionally is substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, phenyl, and morpholine;

$C(O)NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heteroring such as morphline;

$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine;

$CH_2Z$, wherein Z is halogen;

$C(O)NHOH$;

$C(O)NHCN$;

$C(O)N(R_1)SO_2R_{13}$, wherein in $R_{13}$ is $C_1$-$C_4$ alkyl, phenyl, or substituted phenyl;

$C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more members selected from the group consisting of alkoxy, $C_1$-$C_4$ haloalkyl, $C_1$-$C_6$ dialkylamino, and $C_1$-$C_6$ alkylamino;

provided that when the compound is a compound of Formula I, and each of $R_4$, $R_5$, $R_6$ and $R_7$ are H, then X is not C(O)OH.

As used herein, unless otherwise specified, the term "alkyl" means a saturated straight chain or branched non-cyclic hydrocarbon having an indicated number of carbon atoms (e.g., $C_1$-$C_{20}$, $C_1$-$C_{10}$, $C_1$-$C_4$, etc.). Representative saturated straight chain alkyls include -methyl, -ethyl, -n-propyl, -n-butyl, -n-pentyl, -n-hexyl, -n-heptyl, -n-octyl, -n-nonyl and -n-decyl; while representative saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted.

As used herein, unless otherwise specified, the term "cycloalkyl" means a monocyclic or polycyclic saturated ring comprising carbon and hydrogen atoms and having no carbon-carbon multiple bonds. Examples of cycloalkyl groups include, but are not limited to cyclopropyl, cyclobutyl, cyclopentyl, cyclohexyl, and cycloheptyl, and saturated cyclic and bicyclic terpenes. A cycloalkyl group can be unsubstituted or substituted. Preferably, the cycloalkyl group is a monocyclic ring or bicyclic ring.

As used herein, unless otherwise specified, the term "alkenyl group" means a straight chain or branched non-cyclic hydrocarbon having an indicated number of carbon atoms (e.g., $C_2$-$C_{20}$, $C_2$-$C_{10}$, $C_2$-$C_4$, etc.). Representative straight chain and branched alkenyls include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like. The double bond of an alkenyl group can be unconjugated or conjugated to another unsaturated group. An alkenyl group can be unsubstituted or substituted.

As used herein, unless otherwise specified the term "alkynyl group" means a straight chain or branched non-cyclic hydrocarbon having an indicated number of carbon atoms (e.g., $C_2$-$C_{20}$, $C_2$-$C_{10}$, $C_2$-$C_6$, etc.), and including at least one carbon-carbon triple bond. Representative straight chain and branched alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like. The triple bond of an alkynyl group can be unconjugated or conjugated to another unsaturated group. An alkynyl group can be unsubstituted or substituted.

As used herein, unless otherwise specified, the term "halogen" or "halo" means fluorine, chlorine, bromine, or iodine. Furthermore, unless otherwise specified, the term "haloalkyl" means an alkyl substituted with one or more halogens, wherein alkyl and halogen are defined as above.

As used herein, unless otherwise specified, the term "alkoxy" means —O-(alkyl), wherein alkyl is defined above. Furthermore, as used herein, the term "haloalkoxy" means an alkoxy substituted with one or more halogens, wherein alkoxy and halogen are defined as above.

As used herein, unless otherwise specified, the term "heteroaryl" means a carbocyclic aromatic ring containing from 5 to 14 ring atoms comprising at least one heteroatom, preferably 1 to 3 heteroatoms, independently selected from nitrogen, oxygen, or sulfur. Heteroaryl ring structures include compounds having one or more ring structures, such as mono-, bi-, or tricyclic compounds, as well as fused heterocyclic moieties. Representative heteroaryls are triazolyl, tetrazolyl, oxadiazolyl, pyridyl, furanyl, benzofuranyl, thiophenyl, thiazolyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl, oxazolyl, benzo[1,3]dioxole, and 2,3-dihydro-benzo[1,4]dioxine. A heteroaryl group can be unsubstituted or substituted.

As used herein, unless otherwise specified, the term "alkylamino" means —NH(alkyl) or —N(alkyl)(alkyl), wherein alkyl is defined above. As used herein, unless otherwise specified, the term "aminoalkyl" means -(alkyl)-$NH_2$, wherein alkyl is defined above.

As used herein, unless otherwise specified, the term "substituted" means a group substituted by one to four or more substituents, such as, alkyl, alkenyl, alkynyl, cycloalkyl, aroyl, halo, haloalkyl (e.g., trifluoromethyl), haloalkoxy (e.g., trifluoromethoxy), hydroxy, alkoxy, alkylthioether, cycloalkyloxy, heterocylooxy, oxo, alkanoyl, aryl, arylalkyl, alkylaryl, heteroaryl, heteroarylalkyl, alkylheteroaryl, heterocyclo, aryloxy, alkanoyloxy, amino, alkylamino, arylamino, arylalkylamino, cycloalkylamino, heterocycloamino, mono- and di-substituted amino (in which the two substituents on the amino group are selected from alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, cycloalkylthio, heterocyclothio, alkylthiono, arylthiono, arylalkylthiono, alkylsulfonyl, arylsulfonyl, arylalkylsulfonyl, sulfonamido (e.g., $SO_2NH_2$), substituted sulfonamido, nitro, cyano, carboxy, carbamyl (e.g., $CONH_2$), substituted carbamyl (e.g., CONH-alkyl, CONH-aryl, CONH-arylalkyl or instances where there are two substituents on the nitrogen selected from alkyl or arylalkyl), alkoxycarbonyl, aryl, substituted aryl, guanidino, substituted or unsubstituted heterocycloalkyl, substituted or unsubstituted heteroaryl (such as, indolyl, imidazolyl, furyl, thienyl, thiazolyl, pyrrolidyl, pyridyl, pyrimidyl and the like).

Whenever a range of the number of atoms in a structure is indicated (e.g., a $C_1$-$C_8$, $C_1$-$C_6$, $C_1$-$C_4$, or $C_1$-$C_3$ alkyl, haloalkyl, alkylamino, alkenyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, haloalkyl, alkylamino, alkenyl, etc.) referenced herein encompasses and specifically describes 1, 2, 3, 4, 5, 6, 7, or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, 5-6 carbon atoms, 5-7 carbon atoms, 5-8 carbon atoms, 6-7 carbon atoms, or 6-8 carbon atoms, as appropriate).

The invention encompasses all compounds described by Formulas I and II without limitation. However, for the purposes of further illustration, preferred aspects and elements of the invention are discussed herein.

With respect to Formulas I and II, W can be any member selected from the group consisting of C(O), C(S), and $CH_2$. According to certain preferred aspects of the invention, W is C(O), especially with respect to compounds of Formula I. B is $CH_2$ or $CH(CH_NH_{2N+1})$, wherein n is an integer from 1 to 8.

$R_1$ and $R_2$ can be the same or different, and are selected from the group consisting of H and $C_1$-$C_3$ alkyl, or $R_1$ and $R_2$ may be taken together with the carbon atom to which they are attached to form a $C_3$-$C_5$ or $C_3$-$C_6$ cycloalkyl ring or a carbonyl group. Preferably, $R_1$ and $R_2$ are H or $C_1$-$C_3$ alkyl. More preferably, $R_1$ is H and $R_2$ is $C_1$-$C_3$ alkyl, such as $CH_3$.

$R_3$ can be any member selected from the group consisting of H, halogen, $C_1$-$C_4$ alkyl, $C_1$-$C_4$ alkoxy, $C_1$-$C_4$ haloalkyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy. However, $R_3$ preferably is H.

According to one preferred aspect of the invention, at least one of $R_4$, $R_5$, $R_6$ and $R_7$ is not H. Thus, according to this aspect of the invention, at least one of $R_4$, $R_5$, $R_6$ and $R_7$, preferably $R_5$, $R_6$, and/or $R_7$, is selected from the group consisting of hydroxyl, halogen, CN, $NO_2$, sulfonamide, $C_1$-$C_8$ alkyl, $C_3$-$C_6$ cycloalkyl, $C_1$-$C_6$ alkoxy, $C_1$-$C_6$ haloalkoxy, $C_1$-$C_4$ haloalkyl, $C_2$-$C_8$ alkenyl, amino, $C_1$-$C_4$ dialkyl amino, $C_1$-$C_4$ alkylamino, $C_3$-$C_6$ cycloalkyl amino, morpholine, heteroaryl, arylamino, arylalkylamino, phenyl, and C(O)R', NR'(COR"), $NR'SO_2R''$ and NR'(CONR"R'"), wherein in R', R" and R''' are independently H, $C_1$-$C_6$ alkyl, phenyl or substituted phenyl, and phenyl, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine, and the phenyl is optionally substituted with one or more members selected from the group consisting of halogen, $NO_2$, CN, $C_1$-$C_4$ alkyl, $C_1$-$C_4$ haloalkyl, and $C_1$-$C_4$ alkoxy, or any sub-group or sub-combination thereof.

It is further preferred according to this aspect of the invention that either $R_5$ or $R_6$, or both, are not H. Thus, either $R_5$ or $R_6$, or both, are independently selected as above or from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, and morpholine, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine.

Desirably, $R_5$ is H and $R_6$ is selected as described above, or $R_6$ is selected from the group consisting of halogen, $C_1$-$C_3$ alkyl, $C_1$-$C_6$ alkoxy, $C_1$-$C_4$ dialkyl amino, and $C_1$-$C_4$ haloalkyl. More specific examples of suitable $R_6$ groups include chloro, bromo, methyl, ethyl, propyl, i-propyl, methoxy, ethoxy, propoxy, i-propoxy, cyclohexyloxy, dimethylamino, and $CF_3$. When $R_6$ is not H, it is suitable that each of $R_4$, $R_5$, and $R_7$ are H.

When $R_5$ is not H, $R_5$ advantageously can be selected as described above, or from the group consisting of CN, halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, and morpholine, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine. Specific examples of suitable $R_5$ groups include methyl, ethyl, propyl, or CN. When $R_5$ is not H, it is suitable that each of $R_4$, $R_6$, and $R_7$ are H.

When $R_7$ is not H, $R_7$ can be selected as described above, or from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, and morpholine, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine. More specific examples of suitable $R_7$ groups include $C_1$-$C_8$ alkyl, amino, or $C_1$-$C_4$ alkylamino groups, such as methyl, ethyl, propyl, or amino. When $R_7$ is not H, it is suitable that $R_4$, $R_5$, and $R_6$ are H.

Alternatively, or in addition, $R_4$ and $R_5$, $R_5$ and $R_6$, or $R_6$ and $R_7$, may be taken together with the carbon atoms to which they are attached to form a ring, preferably a 5 or 6 membered heterocyclic ring. Non-limiting examples of such rings include a dioxane or dioxolane ring.

Additional preferred compounds of Formula I are those in which wherein at least one of $R_3$, $R_4$, $R_5$, $R_6$, or $R_7$ is hydroxyl, $C_1$-$C_6$ haloalkoxy, $C_2$-$C_6$ alkenyl, or $C_1$-$C_8$ alkyl substituted with an arylamino or arylalkylamino. Preferably, at least one of $R_3$, $R_4$, $R_5$, $R_6$, or $R_7$ is a $C_1$-$C_6$ haloalkoxy. Non-limiting examples of haloalkoxy groups include —$OCHF_2$.

Alternatively, or in addition, at least one of $R_3$, $R_4$, $R_5$, $R_6$, or $R_7$ is $C(O)R'$, $NR'(COR'')$, $NR'SO_2R''$ and $NR'$ $(CONR''R''')$, wherein in R', R'' and R''' are independently H, $C_1$-$C_6$ alkyl, phenyl or substituted phenyl. Non-limiting examples of such groups include urea (e.g., $NH(CO)NH_2$).

X can be any member selected from the group consisting of H, CN, $C(O)OR_8$, wherein $R_8$ is H or $C_1$-$C_8$ alkyl, and the $C_1$-$C_8$ alkyl optionally is substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, phenyl, and morpholine; $C(O)NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heterering such as morphline; $CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine; $CH_2NR_9R_{10}$, wherein $R_9$ and $R_{10}$ are as defined above; $CH_2Z$, wherein Z is halogen; $C(O)NHOH$; $C(O)NHCN$; $C(O)N(R_1)SO_2R_{13}$, wherein in $R_{13}$ is $C_1$-$C_4$ alkyl, phenyl, or substituted phenyl; $C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; provided that when the compound is a compound of Formula I, and each of $R_4$, $R_5$, $R_6$ and $R_7$ are H, then X is not $C(O)OH$.

While X can be chosen as described above, X is more preferably selected from the group consisting of CN; $C(O)OR_8$, wherein $R_8$ is $C_1$-$C_6$ alkyl, optionally substituted with a phenyl; $C(O)NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heterering such as morphline; $CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine; $CH_2NR_9R_{10}$, wherein $R_9$ and $R_{10}$ are as defined above; and $CH_2Z$, wherein Z is halogen; $C(O)NHOH$; $C(O)NHCN$; $C(O)N(R_1)SO_2R_{13}$, wherein in $R_{13}$ is $C_1$-$C_4$ alkyl, phenyl, or substituted phenyl.

According to another preferred aspect, X is selected from the group consisting of CN; $C(O)OR_8$, wherein $R_8$ is $C_1$-$C_6$ alkyl, optionally substituted with a phenyl; $CH_2OR_{11}$, wherein $R_{11}$ is H, $C_1$-$C_8$ alkyl, or $C_3$-$C_6$ cycloalkyl, wherein the $C_1$-$C_8$ alkyl is optionally substituted one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholine; $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heterering such as morphline; and $CH_2Z$, wherein Z is halogen. X can advantageously be selected as $C(O)OR_8$, wherein $R_8$ is $C_1$-$C_6$ alkyl, optionally substituted with a phenyl, or $CH_2Z$, wherein Z is halogen. More specific examples of suitable X groups include $C(O)OR_8$, wherein $R_8$ is methyl, ethyl, propyl, butyl, t-butyl, or benzyl.

According to another preferred aspect of the invention, when X is selected as described above, and is not $C(O)OH$, each of $R_4$, $R_5$, R and $R_7$ can be H. Also, when at least one of $R_4$, $R_5$, $R_6$ and $R_7$ is not H, and is instead selected as described above, X can advantageously be chosen as $C(O)OH$. This aspect of the invention is especially applicable to Formula I compounds.

According to another aspect of the invention, compounds of Formula I are selected such that W is $C(S)$ or $CH_2$, B is $CH_2$, and $R_1$-$R_7$ are selected as described above.

Specific examples of compounds of the invention are provided in Table 1. Accordingly, the invention encompasses each of the compounds provided in Table 1. To the extent any of the compounds provided in Table 1 fall outside the scope of Formula I or II, such compounds are considered additional aspects of the invention. Preferred compounds of Table 1 include those identified as ALB-116244, ALB-115069, ALB1113310, and ALB 112355.

As those of ordinary skill in the art will appreciate, many of the molecules described herein may contain chiral centers and have more than one stereoisomer (e.g, diastereomer or enantiomer) of the molecule exists. If the stereochemistry of a structure or a portion of a structure is not indicated, for example, with bold or dashed lines, the structure or portion of the structure is to be interpreted as encompassing all stereoisomers of it. The invention specifically contemplates any individual stereoisomers (e.g., diastereomers or enantiomers) of the compounds described herein, as well as mixtures thereof (e.g., racemic mixtures).

The compounds of the invention described herein can be prepared by any of several techniques. By way of a non-limiting example, the compounds can be prepared in accordance with Flow Diagrams 1-5 or as set forth in the Examples.

With respect to Flow Diagram 1, compounds of Formula (a) are commercially available or can be readily prepared using routine techniques. A compound of Formula (b) can be prepared by reacting the Formula (a) ester (R=lower alkyl) with a halogenating agent, such as N-bromosuccinimide (NBS), as illustrated in Flow Diagram 1. The Formula (b) compound (benzyl bromide) is then reacted with a compound of Formula (c) (e.g., aniline) to provide the cyclized product of Formula (d). Formula (e) compounds of the invention can then be prepared by hydrolysis of the ester of Formula (d) under basic or acidic conditions.

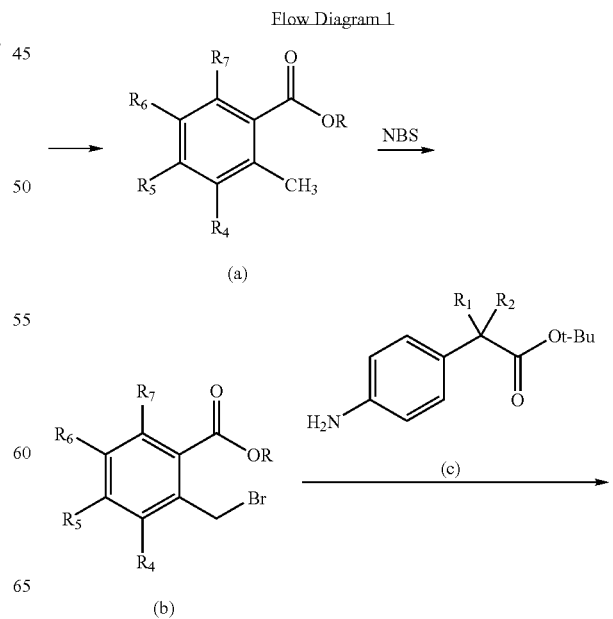

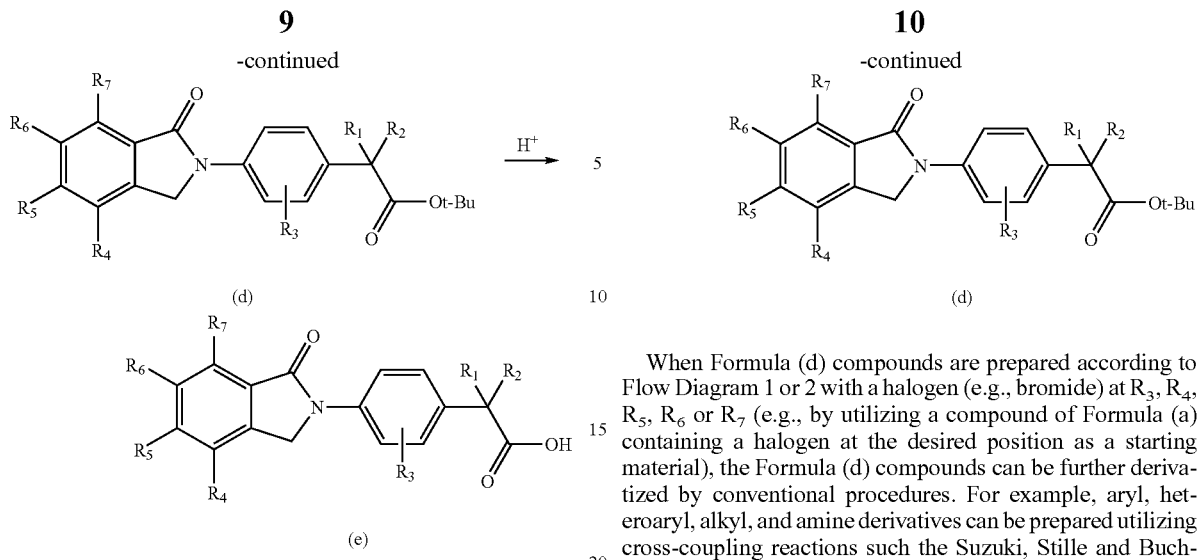

(d)

In some cases the reaction of Formula (b) compounds with Formula (c) compounds results in the production of uncyclized intermediates, as illustrated in Flow Diagram 2 where the uncyclized intermediate is indicated by Formula (f). Hydrolysis of the lower esters of Formula (f) compounds results in Formula (g) acids, which can be treated with a coupling reagent (e.g., EDC) to provide compounds of Formula (d). The compound of Formula (d) can then be hydrolyzed to provide a compound of Formula (e) as illustrated in Flow Diagram 1.

Flow Diagram 2

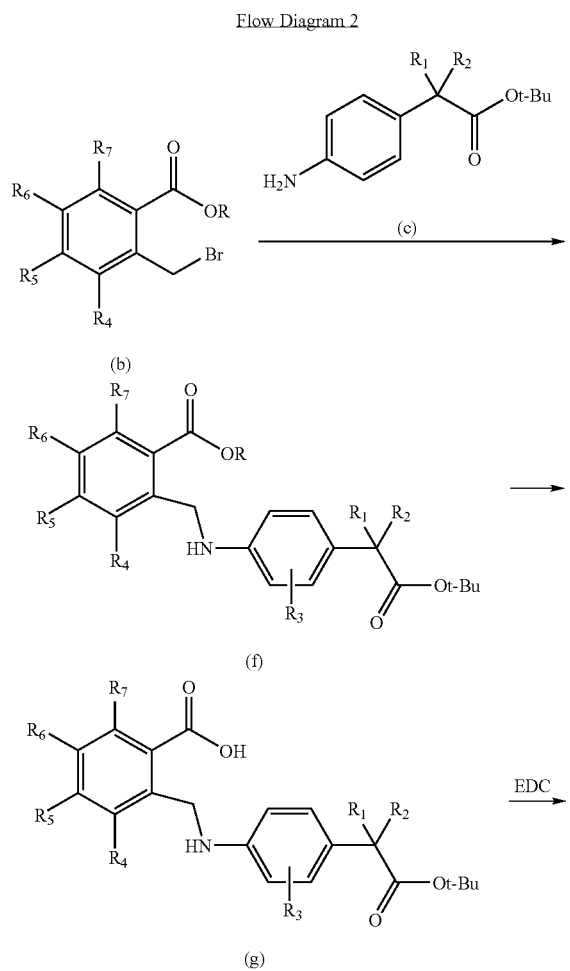

When Formula (d) compounds are prepared according to Flow Diagram 1 or 2 with a halogen (e.g., bromide) at $R_3$, $R_4$, $R_5$, $R_6$ or $R_7$ (e.g., by utilizing a compound of Formula (a) containing a halogen at the desired position as a starting material), the Formula (d) compounds can be further derivatized by conventional procedures. For example, aryl, heteroaryl, alkyl, and amine derivatives can be prepared utilizing cross-coupling reactions such the Suzuki, Stille and Buchwald among others.

When Formula (d) compounds are prepared according to Flow Diagram 1 or 2 with a nitro group at $R_3$, $R_4$, $R_5$, $R_6$ or $R_7$ (e.g., by utilizing a compound of Formula (a) containing a nitro group at the desired position as a starting material), the Formula (d) compounds can be reduced to provide an amine, which can be further derivatized using conventional techniques to provide secondary amines, tertiary amines, amides and sulfonamides.

When Formula (d) compounds are prepared according to Flow Diagram 1 or 2 with a phenol group at $R_3$, $R_4$, $R_5$, $R_6$ or $R_7$ (e.g., by utilizing a compound of Formula (a) containing a phenol group at the desired position as a starting material), the Formula (d) compound can be further derivatized by conventional procedures to provide ethers and esters.

The acid group of Formula (e) compounds prepared according to Flow Diagram 1 or 2 can be derivatized by conventional procedures to provide functional acid derivatives such as esters, amides, and nitriles, or converted to acid isosteres such as acyl sulfonamides, hydroxamic acids, etc.

As illustrated in Flow Diagram 3, Formula (e) acids can be reduced with a reducing reagent (e.g., borane) to provide compounds of Formula (h). Formula (h) compounds can be derivatized by conventional procedures to afford ethers of Formula (i).

Flow Diagram 3

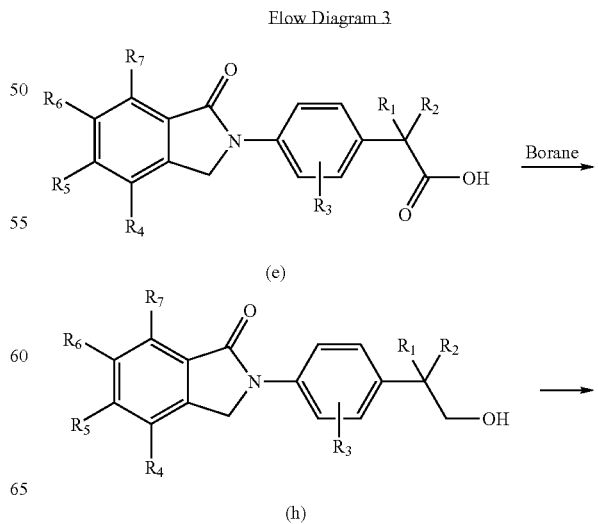

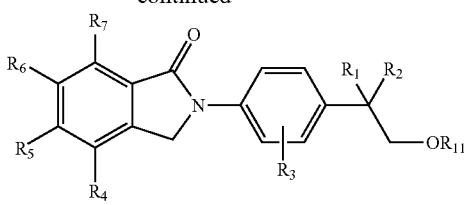

(i)

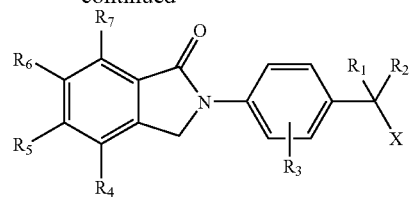

(m)

As illustrated in Flow Diagram 4, Formula (h) compounds can be converted to Formula (j) compounds using a reagent such as triphenylphosphine/carbontetrabromide. Formula (j) compounds can then be reacted with a variety of amines to provide a compound of Formula (k).

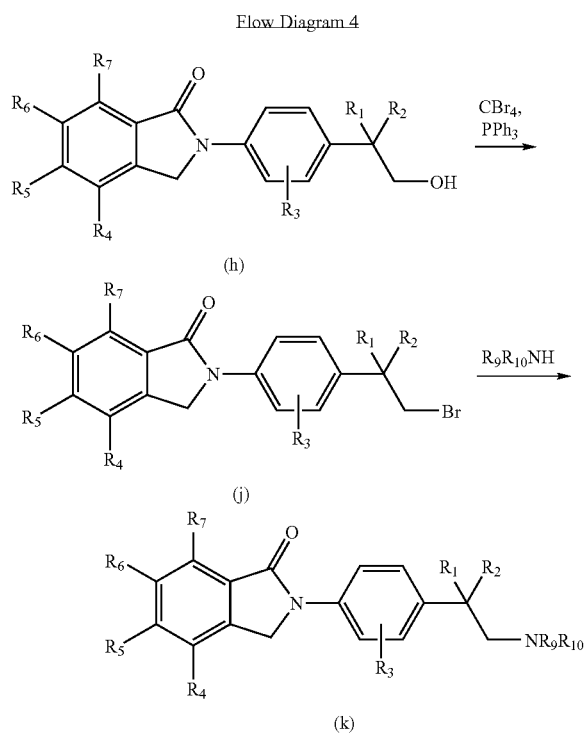

Alternatively, as shown in Flow Diagram 5, some various acid modified analogs can be prepared by cyclization of compounds of Formula (I) with Formula (b) compounds to afford compounds of Formula (m).

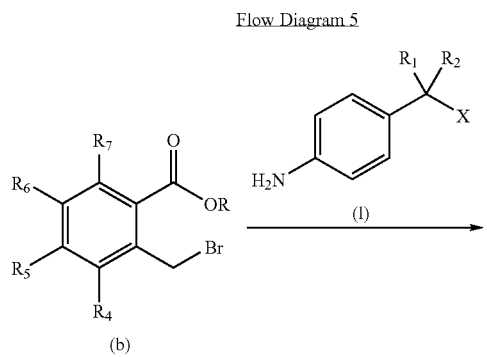

The invention, thus, provides a method of preparing a compound of Formula I or II comprising one or more of the steps set forth above (e.g., Flow Diagrams 1-5) as well as compounds of any of Formulas (a)-(m), which are useful, for example, as intermediates in the preparation of a compound of Formula I or II.

Any one or more of the compounds of the invention described herein can be formed as a composition, such as a pharmaceutical composition, comprising a compound of the invention and a carrier, especially a pharmaceutically acceptable carrier. The pharmaceutical composition can comprise more than one compound of the invention. Alternatively, or in addition, the pharmaceutical composition can comprise one or more compounds of the invention in combination with other pharmaceutically active agents or drugs. Examples of such other pharmaceutically active agents or drugs that may be suitable for use in combination with one or more compound of the invention include drugs that enhance translational read-through (e.g., WO 2004/009558, gentamycin or other aminoglycoside antibiotics), drugs that inhibit one or more histone deacetylase enzymes (e.g., valproate, phenylbutyrate, or hydroxyurea), or drugs that increase SMN expression via other mechanisms. The compounds of the invention also can be administered or formulated in combination with anticancer agents or other antibiotics. Suitable anticancer agents include, without limitation, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol ; mitomycin; bleomycin; doxorubicin; irinotecan; and taxol. Other antibiotics include macrolides (e.g., tobramycin), cephalosporins (e.g., cephalexin, cephradine, cefuroxime, cefprozil, cefaclor, cefixime, or cefadroxil), clarithromycin, erythromycin, penicillins (e.g., penicillin V), and quinolones (e. g., ofloxacin, ciprofloxacin, or norfloxacin).

The composition further comprises a carrier. The carrier can be any suitable carrier. Preferably, the carrier is a pharmaceutically acceptable carrier. With respect to pharmaceutical compositions, the carrier can be any of those conventionally used and is limited only by physio-chemical considerations, such as solubility and lack of reactivity with the active compound(s), and by the route of administration. It will be appreciated by one of skill in the art that, in addition to the following described pharmaceutical composition, the compounds and inhibitors of the present inventive methods can be formulated as inclusion complexes, such as cyclodextrin inclusion complexes, or liposomes.

The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (See, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly (ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

The parenteral formulations will typically contain from about 0.5% to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

One of ordinary skill in the art will readily appreciate that the compounds of the invention described herein can be modified in any number of ways to increase the therapeutic efficacy of the compound. For instance, the compound or inhibitor could be conjugated either directly or indirectly through a linker to a targeting moiety. The practice of conjugating compounds or inhibitors to targeting moieties is known in the art. The term "targeting moiety" as used herein, refers to any molecule or agent that specifically recognizes and binds to a cell-surface receptor, such that the targeting moiety directs the delivery of the compound or inhibitor to a population of cells on which surface the receptor is expressed.

Targeting moieties include, but are not limited to, antibodies, or fragments thereof, peptides, hormones, growth factors, cytokines, and any other naturally- or non-naturally-existing ligands, which bind to cell surface receptors. The term "linker" as used herein, refers to any agent or molecule that bridges the compound or inhibitor to the targeting moiety. One of ordinary skill in the art recognizes that sites on the compounds or inhibitors, which are not necessary for the function of the compound or inhibitor, are ideal sites for attaching a linker and/or a targeting moiety, provided that the linker and/or targeting moiety, once attached to the compound or inhibitor, do(es) not interfere with the function of the compound or inhibitor.

Alternatively, the compounds of the invention described herein can be modified into a depot form, such that the manner in which the compound of the invention is released into the body to which it is administered is controlled with respect to time and location within the body (see, e.g., U.S. Pat. No. 4,450,150). Depot forms of compounds or inhibitors can be, for example, an implantable composition comprising the compound or inhibitor and a porous material, such as a polymer, wherein the compound or inhibitor is encapsulated by or diffused throughout the porous material. The depot is then implanted into the desired location within the body and the compound or inhibitor is released from the implant at a predetermined rate by diffusing through the porous material.

In some contexts, the compounds of the invention can be advantageously administered via an implanted pump that allows intrathecal delivery. Such a delivery method is especially useful for delivery of drugs to the CNS when the drugs administered do not otherwise sufficiently penetrate the blood-brain barrier.

The compounds of the invention described herein can be administered to a cell in vitro. As used herein, the term "in vitro" means that the cell is not in a living organism. The compounds of the invention also can be administered to a cell in vivo. As used herein, the term "in vivo" means that the cell is a part of a living organism or is the living organism. Furthermore, the compounds of the invention can be administered to a host in vivo or ex vivo. The term "ex vivo" as used herein refers to the administration of a compound to a cell or a population of cells in vitro, followed by administration of the cell or population of cells to a host.

Furthermore, the compounds of the invention or composition comprising one or more of the compounds can be administered alone, or in conjunction with of an agent that enhances the efficacy of the compounds of the invention. Such agents can include, for instance, any of the other active agents described herein with respect to the pharmaceutical composition, which agents can be administered in a composition separate from the composition comprising the compounds of the invention.

The amount or dose of the compounds of the invention should be sufficient to effect a therapeutic or prophylactic response in the host over a reasonable time frame. The appropriate dose will depend upon the nature and severity of the disease or affliction to be treated or prevented, as well as by other factors. For instance, the dose also will be determined by the existence, nature and extent of any adverse side effects that might accompany the administration of a particular compound or inhibitor. Ultimately, the attending physician will decide the dosage of the compound or inhibitor of the present invention with which to treat each individual patient, taking into consideration a variety of factors, such as age, body weight, general health, diet, sex, inhibitor to be administered, route of administration, and the severity of the condition being treated. Typically doses might be, for example, 0.1 mg to 1 g daily, such as 5 mg to 500 mg daily.

The compounds of the invention can be administered to a cell, preferably to a cell of a host. Hosts include, for example, bacteria, yeast, fungi, plants, and mammals. Preferably, the host is a mammal. For purposes of the present invention, mammals include, but are not limited to, the order Rodentia, such as mice, and the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human. Furthermore, the host can be the unborn offspring of any of the forgoing hosts, especially mammals or humans, in which case any screening of the host or cells of the host, or administration of compounds to the host or cells of the host, can be performed in utero.

The compounds can be used for any purpose including, without limitation, the treatment, prevention, or diagnosis of a disease or condition, the screening of compounds that can be used to treat, prevent, or diagnose a disease or condition, or the research of the underlying mechanisms or causes of a disease or condition, which research can be used, for example, in the development of methods to treat, prevent, or diagnose the disease or condition. Without wishing to be bound by any particular theory, it is believed that the compounds of the invention are particularly useful with respect to diseases and conditions involving the under-expression of survival motor neuron protein (SMN), diseases and conditions that can be ameliorated by modulation of translational stop codons (e.g., UAA, UAG, UGA; both normal, naturally occurring and mutation introduced stop codons), and diseases and conditions associated with elevated glutamate levels in the central nervous system (CNS) and/or that could be ameliorated by increases in EAAT2 expression.

Preferred compounds of the invention can be used to increase SMN expression in a cell that comprises an SMN2 gene, particularly a cell that does not comprise an SMN1 gene, or that comprises a defective or deleted SMN1 gene. Thus, one aspect of the invention provides a method of increasing SMN expression in a cell comprising administering a compound of the invention to a cell comprising a nucleic acid that encodes SMN2, desirably a cell that comprises a defective or deleted SMN1 gene, whereby SMN expression is increased.

SMN1 and SMN2 refer to two different genes that each encode SMN protein, but that differ by a single base pair. The base pair change in SMN2 results in decreased expression of SMN due to an alternative splicing mechanism that results in an unstable protein that is missing exon 7. As a result, SMN2 transcripts typically are not properly expressed, and SMN protein is produced primarily by SMN1. Most patients that exhibit under-expression of SMN have a defective or mutant SMN1 gene, but an intact SMN2 gene. Without wishing to be bound by any particular theory, it is believed that the compounds of the invention increase the expression of SMN2 via a post-transcriptional mechanism, possibly by increasing translation or otherwise suppressing the effects of translational stop codons introduced by improper splicing of the SMN2 transcript.

The increase in expression of SMN after administration of a compound of the invention can be any increase as compared to the expression level of SMN in the cell in the absence of the compound of the invention. Typically, the cell will have a defective or mutant SMN1 protein and/or reduced levels of SMN protein expression in the absence of a compound of the invention. Methods for detecting and measuring increased SMN expression, particularly through expression of SMN2, are known in the art and described herein.

The cell to which the compound of the invention is administered preferably is in a host. Suitable hosts are as previously described herein. The host is desirably a mammal, especially a human. The method of this aspect of the invention is most suitable for use in conjunction with a host that is afflicted with a disease or at risk for developing a disease, such as a disease associated with the under-expression of SMN. Such diseases include, for example, spinal muscular atrophy (SMA). Preferably, one or more symptoms of the disease are prevented, reduced, or eliminated subsequent to administration of the compound of the invention, thereby effectively treating or preventing the disease to at least some degree. Accordingly, the method of the invention can be used to treat or prevent such a disease.

In a related aspect, the invention provides a method of increasing in a cell the expression of a nucleic acid that encodes a translational stop codon. The stop codon can be a normally occurring stop codon, or a stop codon introduced by mutation or frameshift, particularly a nonsense stop codon. The method comprises administering a compound of the invention to a cell comprising a nucleic acid that encodes a translational stop codon, whereby expression of the nucleic acid is increased. Without wishing to be bound by any particular theory, it is believed that the compounds of the invention permit translational (ribosomal) read-through of stop codons, especially those introduced by mutation or frameshift. According to a preferred aspect of the invention, the stop codon is one that is introduced by a mutation of frameshift, and the compound of the invention permits translational read-through of the stop codon, preferably without interfering with the effect of normal stop codons (e.g., stop codons not introduced by mutation or frameshift, which do not interfere with the production of a full-length protein). The compounds, thus, increase expression of the protein products of such nucleic acids. Compounds of the invention may also modulate gene expression through effects on naturally occurring stop codons.

As used herein, the term "translational stop codon introduced by mutation or frameshift" means any stop codon that results in the premature or otherwise unusual termination of translation and consequential production of a truncated gene product or protein. Translational stop codons introduced by mutation or frameshift include, for example, those that result in a gene product that has reduced stability or reduced activity (or no activity) as compared to the normal, full-length protein product, or results in the reduction or complete absence of a protein product. Translational stop codons introduced by mutation or frameshift also include, for example, those that result in a mRNA that is a target of non-sense-mediated RNA decay. The translational stop codon can be present in the DNA or RNA of any type of cell, and can arise through any type of mutagenesis or frameshift event. For example, the nucleic acid that encodes the translational stop codon can be, without limitation, a defective SMN1 gene or a defective or normal SMN2 gene, or any transcript thereof. In particular, the alternative splicing event that occurs during SMN2 expression, which results in the deletion of SMN exon 7, also creates a nonsense stop codon. The nucleic acid comprising the stop codon can be endogenous to the cell, or a nucleic acid introduced into the cell, for example, by a virus. Without wishing to be bound by any particular theory, it is believed that the compounds of the invention can increase expression of SMN by suppressing the effects of the nonsense stop codons, possibly by allowing translational read-through of the stop codon or by suppressing nonsense-mediated mRNA decay.

An appropriate screening assay can be employed to determine whether a cell or host comprises a nucleic acid that encodes a translational stop codon introduced by mutation or frameshift. For instance, the DNA or RNA of a cell (e.g., a cell of a host or an organism that is pathogenic to the host) can be sequenced or subject to Southern Blot, polymerase chain reaction (PCR), use of the Short Tandem Repeat (STR), or polymorphic length restriction fragments (RFLP) analysis to determine if a nonsense mutation is present. Alternatively, it can be determined if a cell (e.g., a cell of a host) expresses altered levels of a protein encoded by the nucleic acid using western blot or other immunoassays. Other methods of determining whether a nucleic acid that encodes a premature translational stop codon are available.

The cell to which the compound of the invention is administered preferably is in a host. Suitable hosts are as previously described herein. The host is desirably a mammal, especially a human.

The method of this aspect of the invention is most suitable for use in conjunction with a host that is afflicted with a disease, or at risk for developing a disease, associated with a translational stop codon introduced by mutation or frameshift. The types of diseases associated with translational stop codons introduced by mutation or frameshift, the symptoms of which can be ameliorated by the suppression of premature translation termination and/or nonsense-mediated mRNA decay, include, but are not limited to, genetic diseases, autoimmune diseases, blood diseases, collagen diseases, diabetes, neurodegenerative diseases, proliferative diseases, cardiovascular diseases, pulmonary diseases, inflammatory diseases, central nervous system diseases, infectious diseases (bacterial and viral), cancers (including tumors and other cancers), especially cancers associated with p53 mutations.

Specific examples of genetic diseases include, without limitation, SMA, amyloidosis, hemophilia, Alzheimer's disease, Tay Sachs disease, Niemann Pick disease, atherosclerosis, giantism, dwarfism, hypothyroidism, hyperthyroidism, aging, obesity, Parkinson's disease, Huntington's disease, cystic fibrosis, muscular dystrophy, heart disease, kidney stones, ataxia-telangiectasia, familial hypercholesterolemia, retinitis pigmentosa, Duchenne muscular dystrophy, and Marfan syndrome.

Specific examples of inflammatory and autoimmune diseases include, without limitation, arthritis, rheumatoid arthritis, osteoarthritis, and graft versus host disease. Specific examples of blood diseases include, without limitation, hemophilia, Von Willebrand disease, ataxia-telangiectasia, thalassemia (e.g., β-thalassemia), and kidney stones.

Specific examples of blood diseases include, without limitation, hemophilia, Von Willebrand disease, ataxia-telangiectasia, thalassemia (e.g., β-thalassemia), and kidney stones.

Specific examples of collagen diseases include, without limitation, osteogenesis imperfecta and cirrhosis.

Specific examples of central nervous system diseases include, without limitation, multiple sclerosis, muscular dystrophy, Duchenne muscular dystrophy, Alzheimer's disease, Huntington's Disease, Tay Sachs disease, late infantile neuronal ceroidlipofuscinosis (LINCL), Leber's hereditary optic neuropathy, and Parkinson's disease.

Specific examples of infectious diseases include, without limitation, HIV/AIDS, viral hepatitis, HPV infection, and *Pseudomonas aeruginosa* infection.

Specific examples of cancers include cancer of the head and neck, eye, skin, mouth, throat, esophagus, chest, bone, lung, colon, sigmoid, rectum, stomach, prostate, breast, ovaries, kidney, liver, pancreas, brain, intestine, heart or adrenals. More particularly, cancers include include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., Harrison's Principles of Internal Medicine, Eugene Braunwald et al., eds., pp. 491 762 (15th ed. 2001).

Diseases, such as cancers, associated with p53 mutations that result in a translational stop codon include, but are not limited to, the diseases and mutations described in Masuda et al., *Tokai J Exp Clin Med.* 25 (2): 69-77 (2000); Oh et al., *Mol Cells* 10 (3): 275-80 (2000); Li et al., *Lab Invest.* 80 (4): 493-9 (2000); Yang et al., *Zhonghua Zhong Liu Za Zhi* 21 (2):114-8 (1999); Finkelstein et al., *Mol Diagn.* 3(1): 37-41 (1998); Kajiyama et al., *Dis Esophagus.* 11 (4): 279-83 (1998); Kawamura et al., *Leuk Res.* 23 (2): 115-26 (1999); Radig et al., *Hum Pathol.* 29 (11): 1310-6 (1998); Schuyer et al., *Int J Cancer* 76 (3): 299-303 (1998); Wang-Gohrke et al., *Oncol Rep.* 5(1): 65-8 (1998); Fulop et al., *J Reprod Med.* 43 (2): 119-27 (1998); Ninomiya et al., *J Dermatol Sci.* 14 (3):173-8 (1997); Hsieh et al., *Cancer Lett.* 100 (1-2): 107-13 (1996); Rall et al., *Pancreas.* 12(1): 10-7 (1996); Fukutomi et al., *NipponRinsho* 53 (11): 2764-8 (1995); Frebourg et al., *Am J Hum Genet.* 56 (3): 608-15 (1995); Dove et al., *Cancer Surv.* 25: 335-55 (1995); Adamson et al., *Br J Haematol.* 89(1): 61-6 (1995); Grayson et al., *Am J Pediatr Hematol Oncol.* 16 (4): 341-7 (1994); Lepelley et al., *Leukemia* 8 (8): 1342-9 (1994); McIntyre et al., *J Clin Oncol.* 12 (5): 925-30 (1994); Horio et al., *Oncogene.* 9 (4): 1231-5 (1994); Nakamura et al., *Jpn J Cancer Res.* 83 (12): 1293-8 (1992); Davidoff et al., *Oncogene.* 7(1): 127-33 (1992); and Ishioka et al., *Biochem Biophys Res Commun.* 177 (3): 901-6 (1991).

Preferably, one or more symptoms of the disease are prevented, reduced, or eliminated subsequent to administration of the compound of the invention, thereby effectively treating or preventing the disease to at least some degree. Accordingly, the method of the invention can be used to treat or prevent such a disease.

In yet another related aspect, the invention provides a method of increasing the expression of excitatory amino acid transporter (EAAT2) in a cell comprising administering a compound of the invention to a cell comprising a nucleic acid that encodes EAAT2, whereby expression of EAAT2 is increased. Certain diseases (e.g., Parkinson's disease, Alzheimer's disease, amyotrophic lateral sclerosis (ALS), and epilepsy) and other conditions, such as stroke or other trauma to the CNS, are associated with elevated glutamate levels in the CNS that can be toxic, leading to brain damage or even death. Cellular uptake of glutamate via the EAAT2 transporter is responsible, at least in part, for maintaining appropriately low glutamate levels in the CNS. Without wishing to be bound by any particular theory, it is believed that the compounds of the invention can activate or enhance EAAT2 expression, thereby advantageously lowering glutamate levels in the CNS. Methods of detecting and measuring increased EAAT2 expression are known in the art and described, for instance, in Rothstein et al., *Nature,* 43(3), 73-7 (2005).

The cell to which the compound of the invention is administered preferably is in a host. Suitable hosts are as previously described herein. The host is desirably a mammal, especially a human. The method of this aspect of the invention is most suitable for use in conjunction with a host that is afflicted with a disease or condition, or at risk for developing a disease or condition, associated with decreased expression of EAAT2 or elevated glutamate levels in the CNS. Such diseases and conditions include, for example, Parkinson's disease, Alzheimer's disease, amyotrophic lateral sclerosis (ALS), epilepsy, stroke, and other forms of CNS trauma. Preferably, one or more symptoms of the disease or condition are prevented, reduced, or eliminated subsequent to administration of the compound of the invention, thereby effectively treating or preventing the disease or condition to at least some degree. Accordingly, the method of the invention can be used to treat or prevent such a disease or condition.

In addition to the foregoing characteristics, preferred compounds of the invention are able to penetrate the blood-brain barrier so as to accumulate in therapeutically effective amounts, and do not have significant cyclooxygenase (Cox) inhibitory activity (e.g., has less than toxic levels of Cox inhibitory activity).

TABLE 1

| No. | STRUCTURE | Identifier | SMN Splice Reporter Assay (Example 10) | |
|---|---|---|---|---|
| | | | Avg EC50 (uM) | Avg MaxFold Increase |
| 1 | 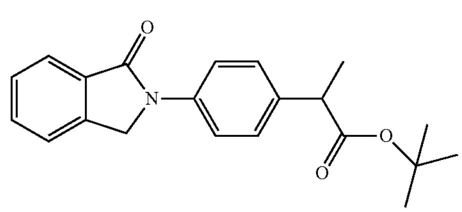 | ALB-111730 | 1.66 | 1.267 |

TABLE 1-continued
| No. | STRUCTURE | Identifier | SMN Splice Reporter Assay (Example 10) | |
| | | | Avg EC50 (uM) | Avg MaxFold Increase |
| --- | --- | --- | --- | --- |
| 2 | 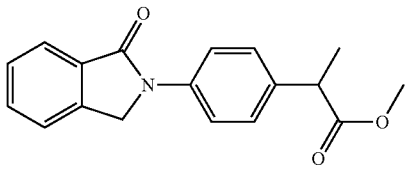 | ALB-111731 | 0.174 | 1.431 |
| 3 | 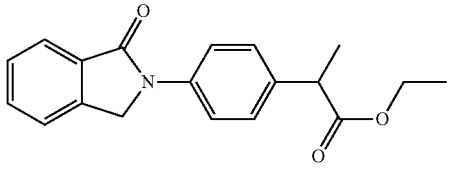 | ALB-111732 | 0.325 | 1.414 |
| 4 | 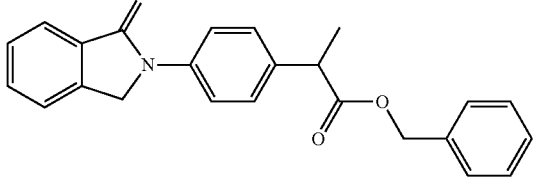 | ALB-111733 | 0.528 | 1.56 |
| 5 | 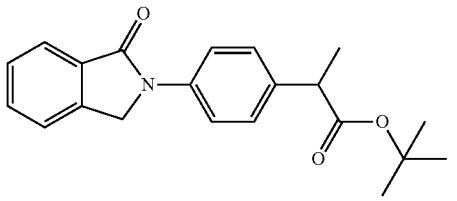 | ALB-111738 | 2.295 | 1.172 |
| 6 | 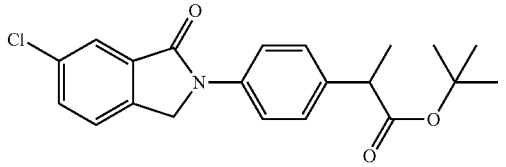 | ALB-111740 | 2.023 | 1.487 |
| 7 | 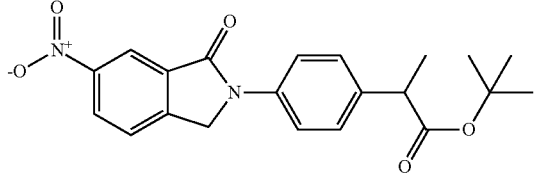 | ALB-111741 | 0.875 | 1.116 |
| 8 | 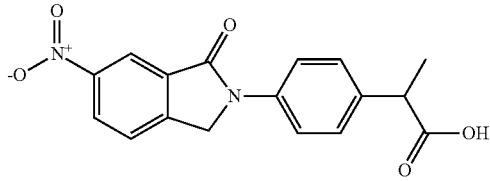 | ALB-111742 | 17.865 | 1.329 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 9 | 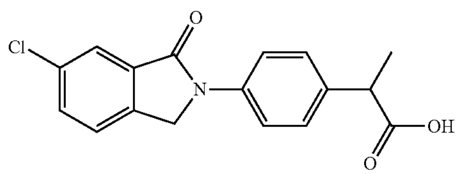 | ALB-111743 | 0.267 | 1.67 |
| 10 | 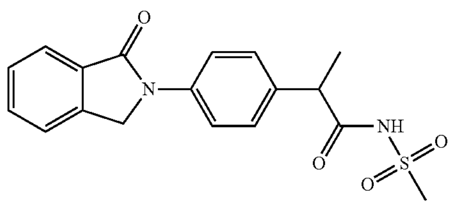 | ALB-111744 | | 1.135 |
| 11 | 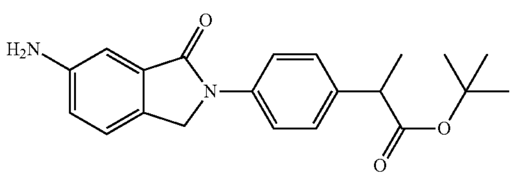 | ALB-111745 | 2.124 | 1.168 |
| 12 | 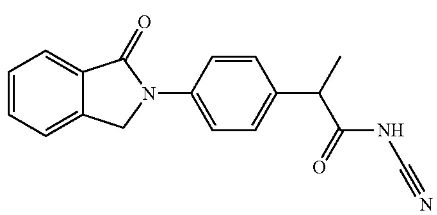 | ALB-111746 | | 1.112 |
| 13 | 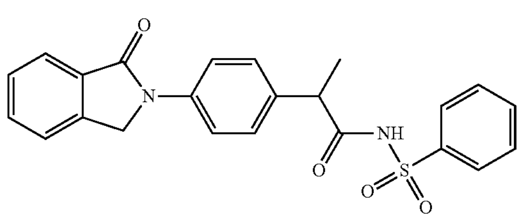 | ALB-111747 | | 1.042 |
| 14 | 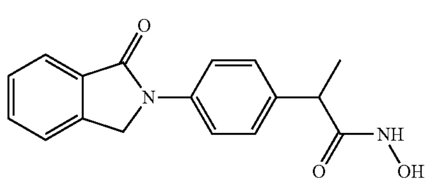 | ALB-111748 | 2.266 | 1.377 |
| 15 | 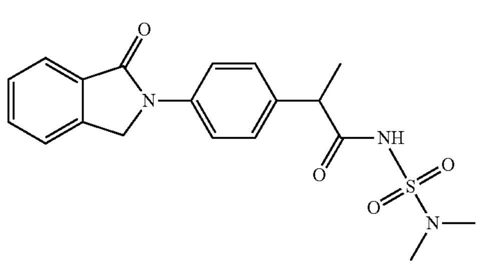 | ALB-111749 | 13.971 | 1.163 |

TABLE 1-continued

| No. | STRUCTURE | Identifier | SMN Splice Reporter Assay (Example 10) Avg EC50 (uM) | Avg MaxFold Increase |
|---|---|---|---|---|
| 16 | 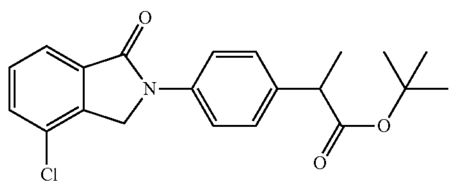 | ALB-111760 | | 1.067 |
| 17 | 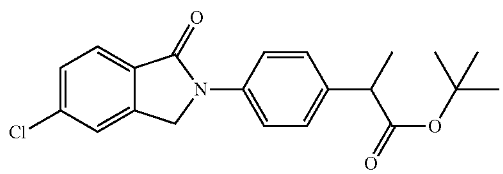 | ALB-111761 | 5.559 | 1.194 |
| 18 | 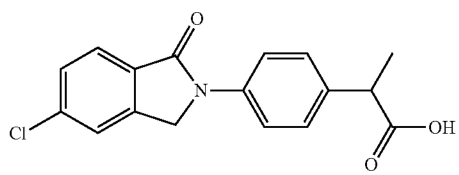 | ALB-111762 | 0.358 | 1.38 |
| 19 | 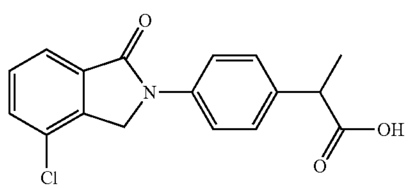 | ALB-111763 | 13.868 | 1.169 |
| 20 | 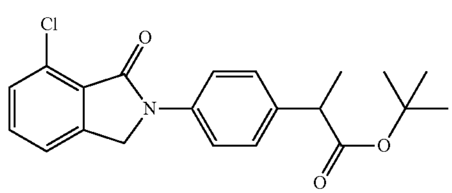 | ALB-111783 | 1.562 | 1.129 |
| 21 | 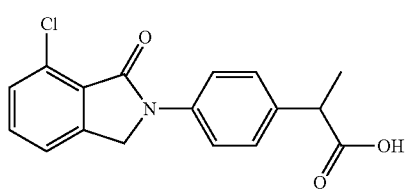 | ALB-111784 | 1.129 | 1.408 |
| 22 | 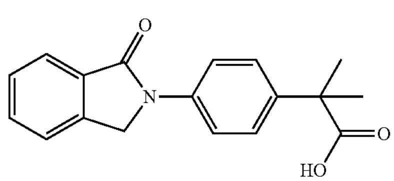 | ALB-111796 | 3.516 | 1.221 |
| 23 | 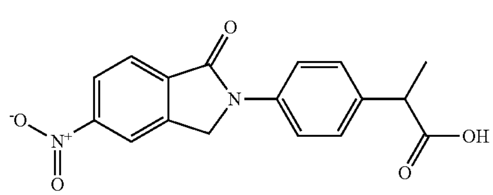 | ALB-111841 | 0.441 | 1.267 |

TABLE 1-continued

| No. | STRUCTURE | Identifier | SMN Splice Reporter Assay (Example 10) Avg EC50 (uM) | Avg MaxFold Increase |
|---|---|---|---|---|
| 24 | 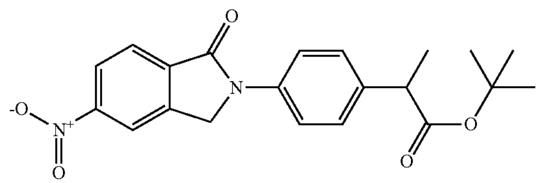 | ALB-111842 | | 1.206 |
| 25 | 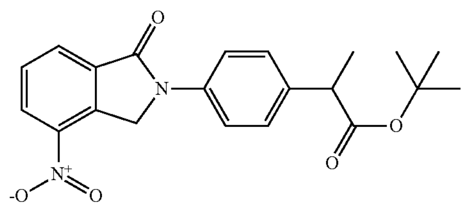 | ALB-111843 | 2.002 | 1.202 |
| 26 | 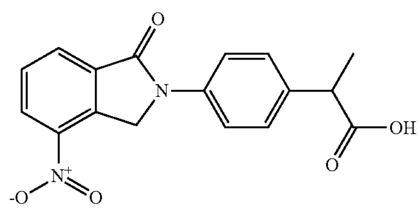 | ALB-111844 | | 1.158 |
| 27 | 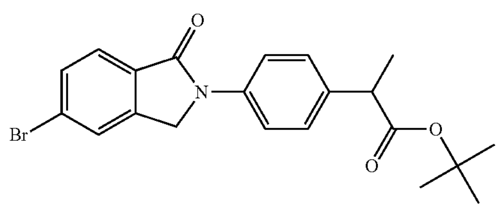 | ALB-111853 | 21.38 | 1.102 |
| 28 | 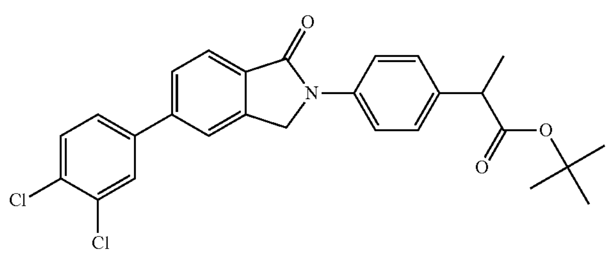 | ALB-111854 | | 1.036 |
| 29 | 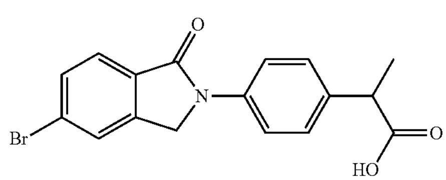 | ALB-111855 | 0.553 | 1.355 |
| 30 | 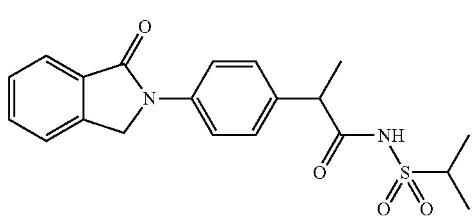 | ALB-111856 | 0.568 | 1.142 |

TABLE 1-continued
| No. | STRUCTURE | Identifier | SMN Splice Reporter Assay (Example 10) Avg EC50 (uM) | Avg MaxFold Increase |
|---|---|---|---|---|
| 31 | 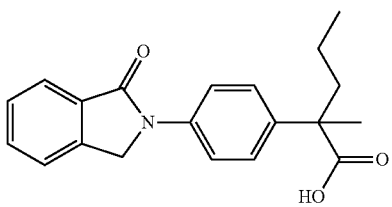 | ALB-111857 | | 1.07 |
| 32 | 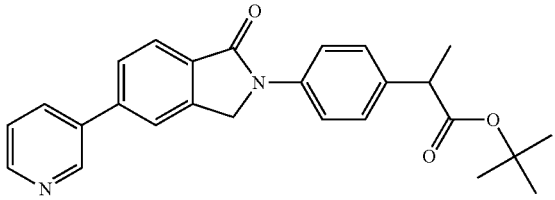 | ALB-111884 | | 1.032 |
| 33 | 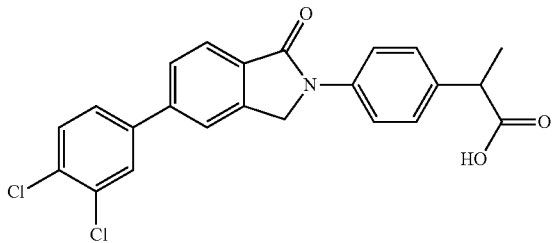 | ALB-111885 | | 1.094 |
| 34 | 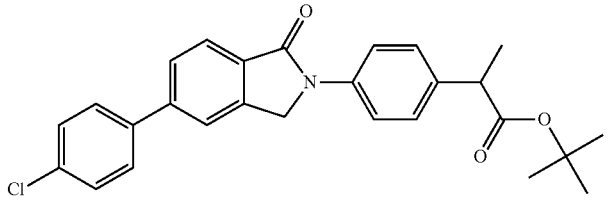 | ALB-111886 | | 1.069 |
| 35 | 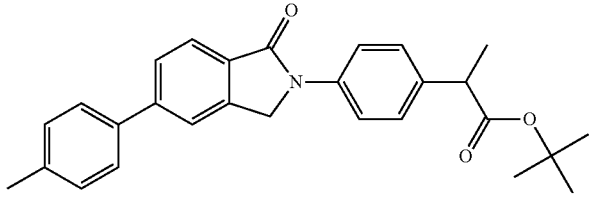 | ALB-111887 | | 1.038 |
| 36 | 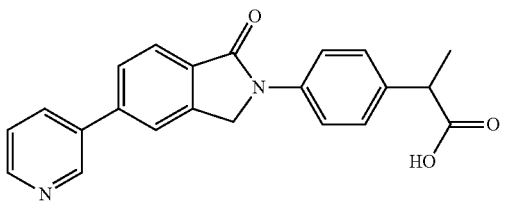 | ALB-111889 | | 1.047 |
| 37 | 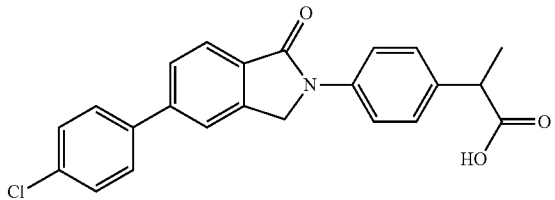 | ALB-111890 | 7.74 | 1.161 |

TABLE 1-continued
| No. | STRUCTURE | Identifier | Avg EC50 (uM) | Avg MaxFold Increase |
|---|---|---|---|---|
| 38 | 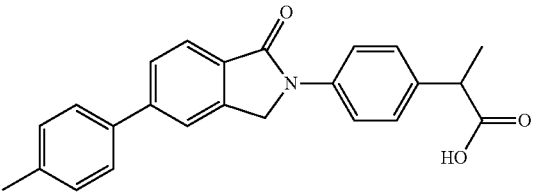 | ALB-111891 | 8.88 | 1.314 |
| 39 | 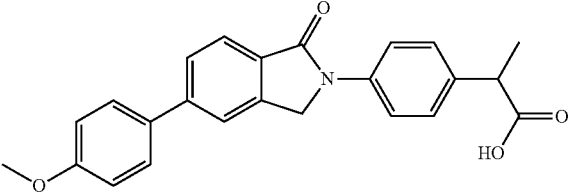 | ALB-111892 | 4.307 | 1.459 |
| 40 | 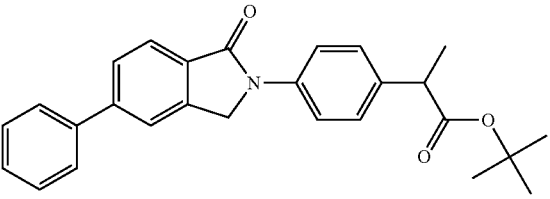 | ALB-111888 | | 1.105 |
| 41 | 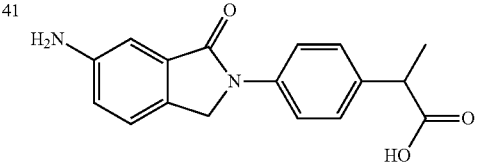 | ALB-111883a | 1.257 | 1.173 |
| 42 | 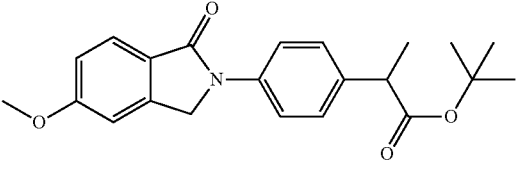 | ALB-111893 | | 1.091 |
| 43 | 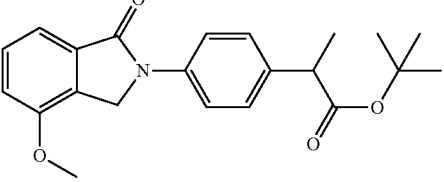 | ALB-111894 | 3.163 | 1.289 |
| 44 | 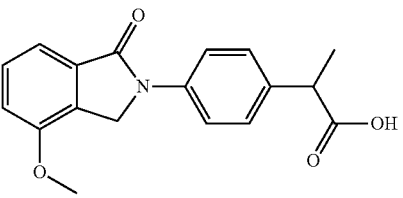 | ALB-111895 | | 1.152 |

TABLE 1-continued

| No. | STRUCTURE | Identifier | SMN Splice Reporter Assay (Example 10) Avg EC50 (uM) | Avg MaxFold Increase |
|---|---|---|---|---|
| 45 | (2-bromophenyl isoindolinone tert-butyl propanoate) | ALB-111882 | 2.831 | 1.235 |
| 46 | (5-amino isoindolinone phenyl tert-butyl propanoate) | ALB-111949 | 5.221 | 1.286 |
| 47 | (5-amino isoindolinone phenyl propanoic acid) | ALB-111950a | | 1.072 |
| 48 | (7-nitro isoindolinone phenyl tert-butyl propanoate) | ALB-111951 | | 1.199 |
| 49 | (4-amino isoindolinone phenyl tert-butyl propanoate) | ALB-111952 | | 1.039 |
| 50 | (7-methoxy isoindolinone phenyl tert-butyl propanoate) | ALB-111955 | 0.396 | 1.076 |
| 51 | (7-methoxy isoindolinone phenyl propanoic acid) | ALB-111957 | | 1.233 |

TABLE 1-continued
| No. | STRUCTURE | Identifier | Avg EC50 (uM) | Avg MaxFold Increase |
|---|---|---|---|---|
| 52 | 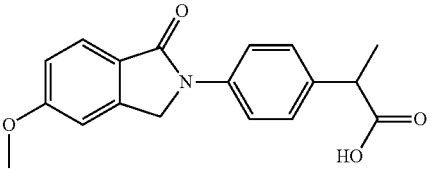 | ALB-111959 | 0.451 | 1.264 |
| 53 | 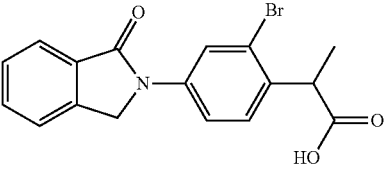 | ALB-111962 |  | 1.084 |
| 54 | 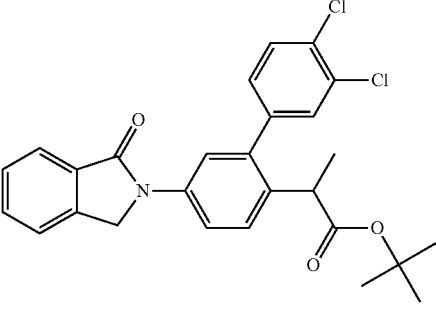 | ALB-111963 |  | 1.025 |
| 55 | 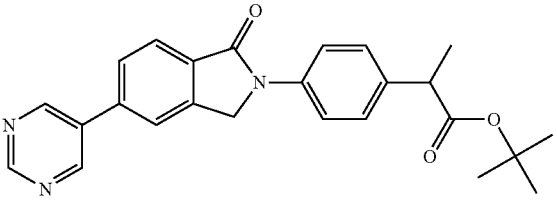 | ALB-111991 |  | 1.087 |
| 56 | 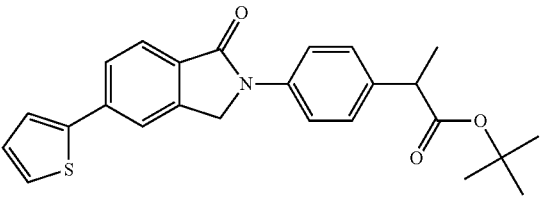 | ALB-111992 |  | 1.012 |
| 57 | 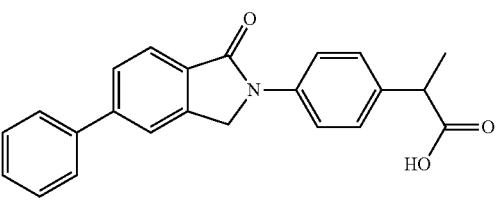 | ALB-111993 | 2.948 | 1.544 |
SMN Splice Reporter Assay (Example 10)

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 58 | 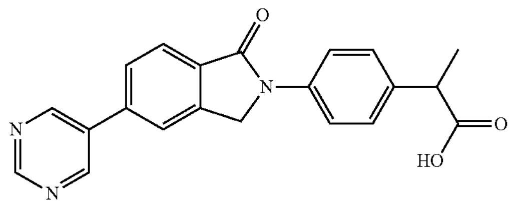 | ALB-111994 | 4.178 | 1.383 |
| 59 | 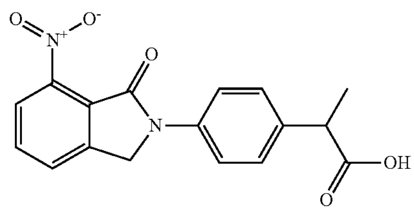 | ALB-111995 | 11.978 | 1.245 |
| 60 | 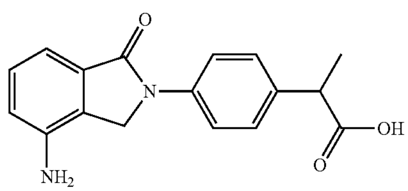 | ALB-111996a | | 1.107 |
| 61 | 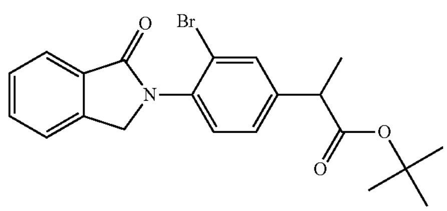 | ALB-111998 | | 1.044 |
| 62 | 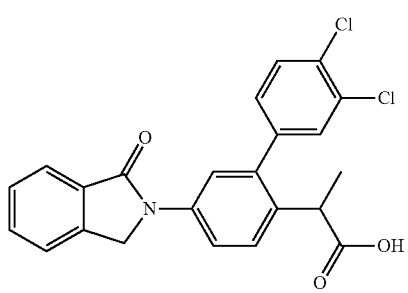 | ALB-111999 | | 1.047 |
| 63 | 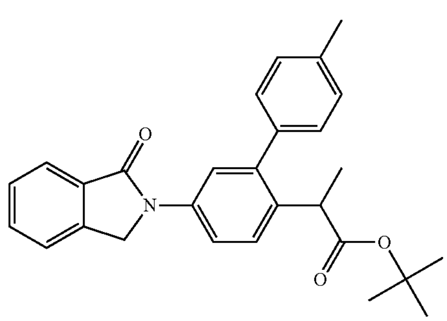 | ALB-112000 | | 1.058 |

TABLE 1-continued
| No. | STRUCTURE | Identifier | SMN Splice Reporter Assay (Example 10) | |
| --- | --- | --- | --- | --- |
| | | | Avg EC50 (uM) | Avg MaxFold Increase |
| 64 | 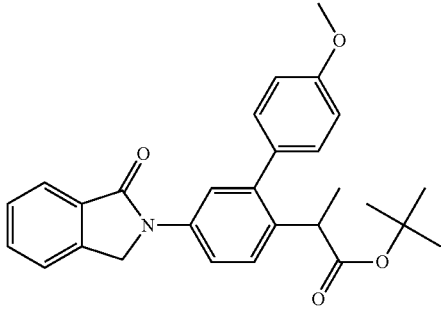 | ALB-112001 | | 1.021 |
| 65 | 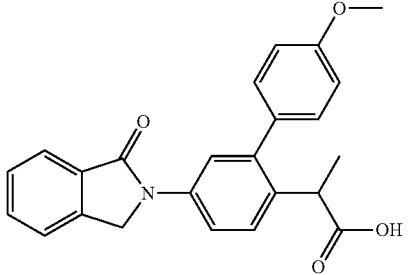 | ALB-112002 | | 1.078 |
| 66 | 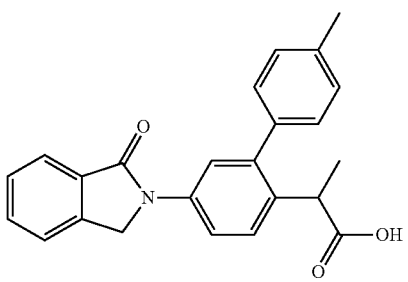 | ALB-112003 | 2.056 | 1.089 |
| 67 | 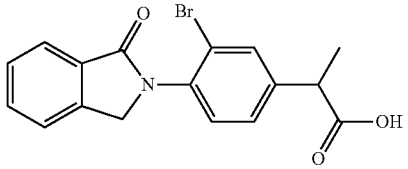 | ALB-112004 | 1.253 | 1.085 |
| 68 | 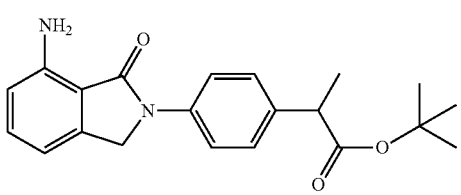 | ALB-112061 | 3.736 | 1.274 |
| 69 | 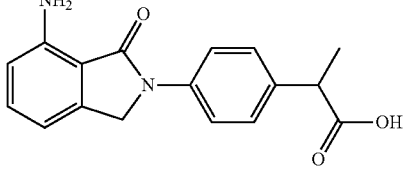 | ALB-112062a | 0.329 | 1.414 |

TABLE 1-continued

| No. | STRUCTURE | Identifier | Avg EC50 (uM) | Avg MaxFold Increase |
|---|---|---|---|---|
| 70 | 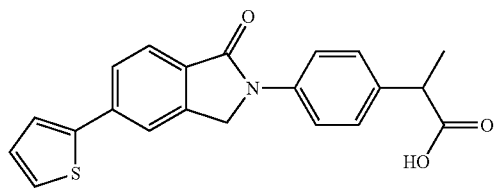 | ALB-112063 | 0.909 | 1.202 |
| 71 | 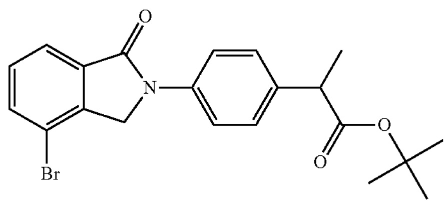 | ALB-112064 | | 1.044 |
| 72 | 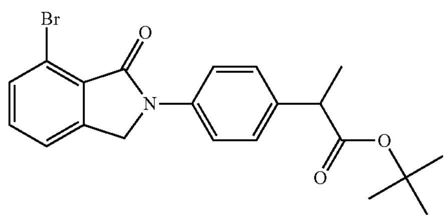 | ALB-112065 | 1.34 | 1.22 |
| 73 | 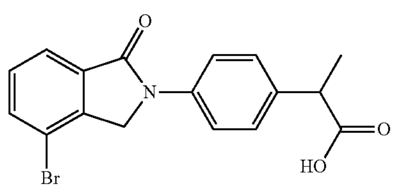 | ALB-112066 | 21.777 | 1.122 |
| 74 | 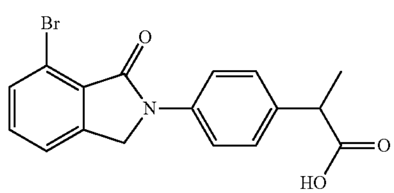 | ALB-112067 | 9.713 | 1.36 |
| 75 | 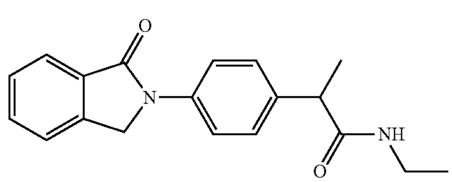 | ALB-112073 | | 1.179 |
| 76 | 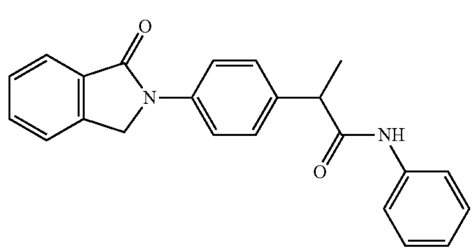 | ALB-112075 | 0.578 | 1.25 |

TABLE 1-continued
| No. | STRUCTURE | Identifier | Avg EC50 (uM) | Avg MaxFold Increase |
|---|---|---|---|---|
| 77 | 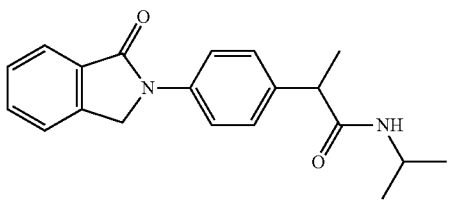 | ALB-112076 | 1.372 | 1.125 |
| 78 | 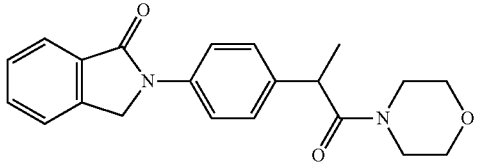 | ALB-112077 | | 1.094 |
| 79 | 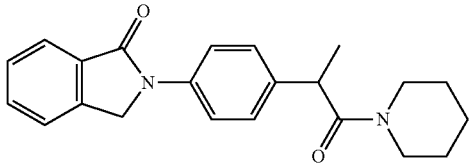 | ALB-112078 | | 1.153 |
| 80 | 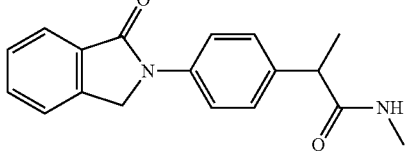 | ALB-112079 | | 1.139 |
| 81 | 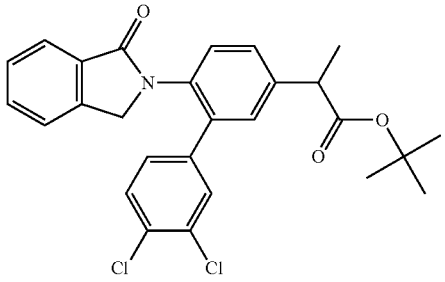 | ALB-112080 | | 1.033 |
| 82 | 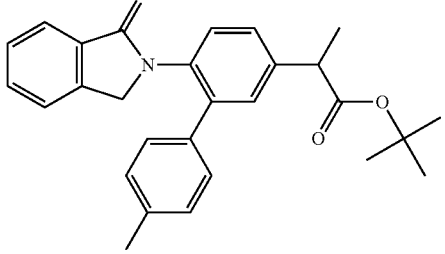 | ALB-112081 | | 1.026 |

TABLE 1-continued

| No. | STRUCTURE | Identifier | SMN Splice Reporter Assay (Example 10) | |
| --- | --- | --- | --- | --- |
| | | | Avg EC50 (uM) | Avg MaxFold Increase |
| 83 | | ALB-112082 | | 1.123 |
| 84 | | ALB-112083 | | 1.095 |
| 85 | | ALB-112084 | | 1.114 |
| 86 | | ALB-112085. | | 1.083 |
| 87 | | ALB-112086 | | 1.081 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 88 | 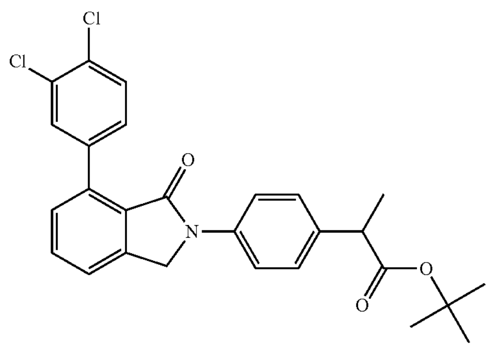 | ALB-112149 | | 1.064 |
| 89 | 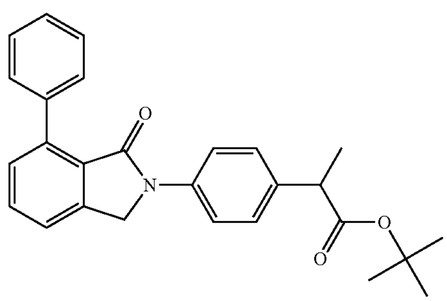 | ALB-112150 | | 1.096 |
| 90 | 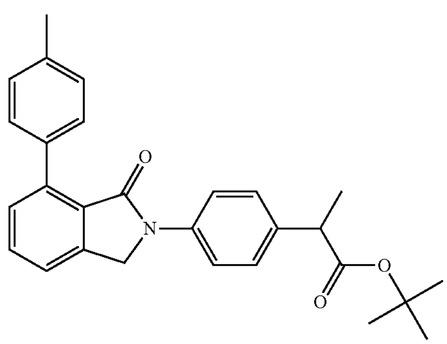 | ALB-112151 | | 1.114 |
| 91 | 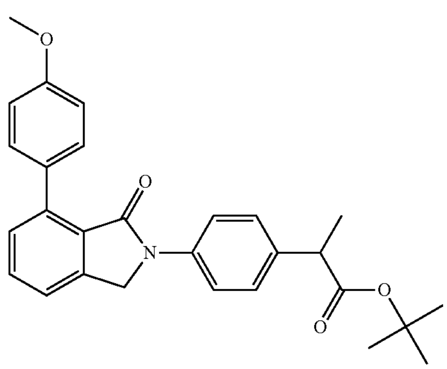 | ALB-112152 | | 1.036 |

TABLE 1-continued

| | | | SMN Splice Reporter Assay (Example 10) | |
|---|---|---|---|---|
| No. | STRUCTURE | Identifier | Avg EC50 (uM) | Avg MaxFold Increase |
| 92 | | ALB-112153 | | 1.022 |
| 93 | | ALB-112154 | | 1.112 |
| 94 | | ALB-112155 | 26.348 | 1.185 |
| 95 | | ALB-112174 | | 1.183 |

TABLE 1-continued
| No. | STRUCTURE | Identifier | SMN Splice Reporter Assay (Example 10) Avg EC50 (uM) | Avg MaxFold Increase |
|---|---|---|---|---|
| 96 | 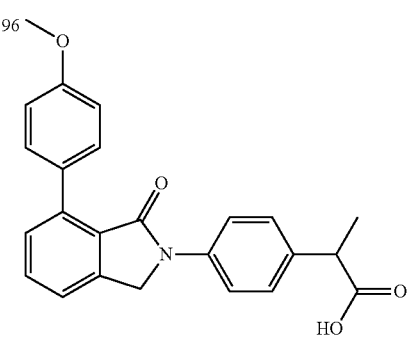 | ALB-112156 |  | 1.27 |
| 97 | 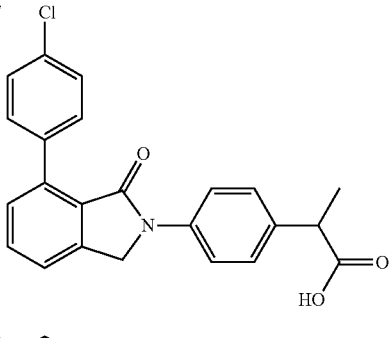 | ALB-112175 | 16.926 | 1.366 |
| 98 | 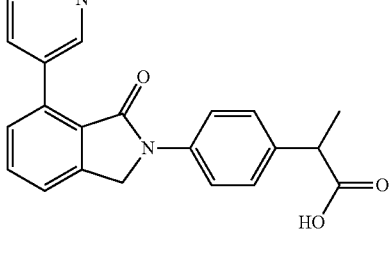 | ALB-112157 | 20.512 | 1.196 |
| 99 | 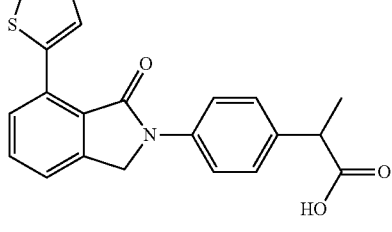 | ALB-112158 | 11.429 | 1.239 |
| 100 | 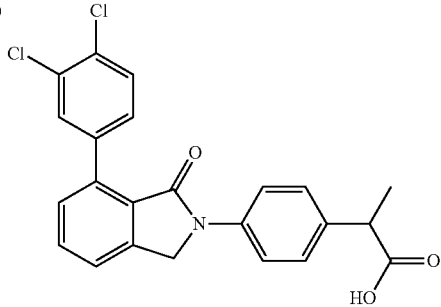 | ALB-112159 |  | 1.477 |

TABLE 1-continued

| No. STRUCTURE | Identifier | SMN Splice Reporter Assay (Example 10) | |
|---|---|---|---|
| | | Avg EC50 (uM) | Avg MaxFold Increase |
| 101 | ALB-112160 | | 1.024 |
| 102 | ALB-112161 | | 1.096 |
| 103 | ALB-112162 | | 1.032 |
| 104 | ALB-112163 | | 1.029 |
| 105 | ALB-112164 | | 1.052 |

TABLE 1-continued

| No. | STRUCTURE | Identifier | SMN Splice Reporter Assay (Example 10) Avg EC50 (uM) | Avg MaxFold Increase |
|---|---|---|---|---|
| 106 | 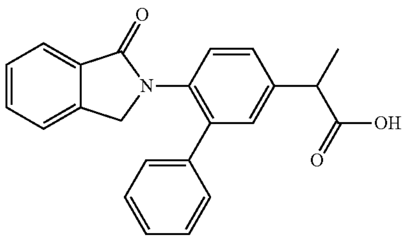 | ALB-112165 | | 1.146 |
| 107 | 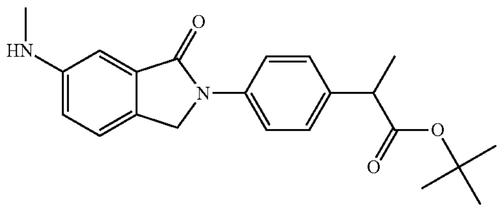 | ALB-112170 | 1.038 | 1.275 |
| 108 | 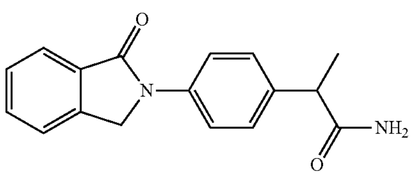 | ALB-112171 | 6.716 | 1.34 |
| 109 | 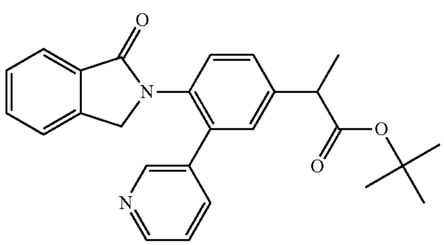 | ALB-112172 | | 1.041 |
| 110 | 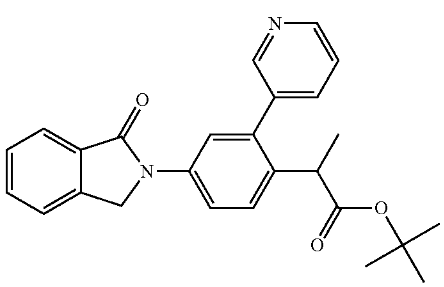 | ALB-112173 | | 1.004 |
| 111 | 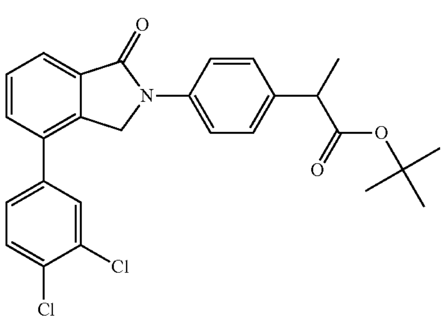 | ALB-112186 | | 1.079 |

TABLE 1-continued

| No. | STRUCTURE | Identifier | SMN Splice Reporter Assay (Example 10) Avg EC50 (uM) | Avg MaxFold Increase |
|---|---|---|---|---|
| 112 | 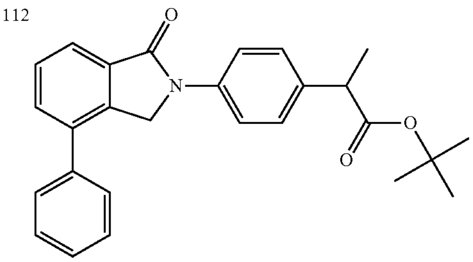 | ALB-112187 | | 1.075 |
| 113 | 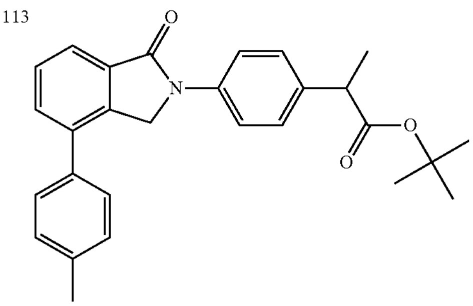 | ALB-112188 | | 1.082 |
| 114 | 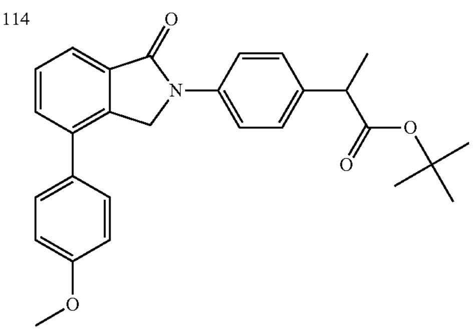 | ALB-112159 | | 1.066 |
| 115 | 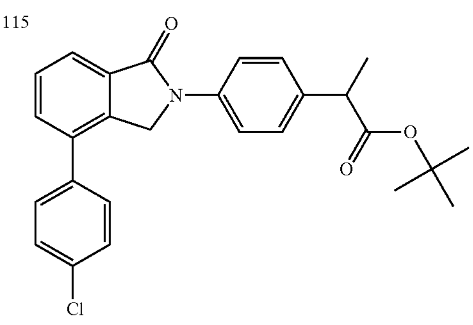 | ALB-112190 | | 1.099 |
| 116 | 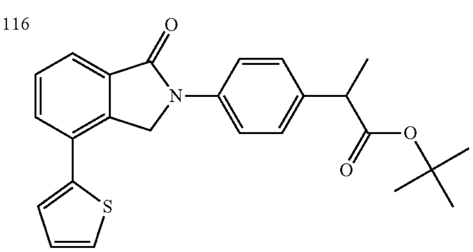 | ALB-112191 | | 1.124 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 117 | 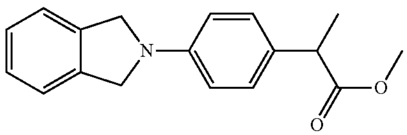 | ALB-112192 | 5.721 | 1.412 |
| 118 | 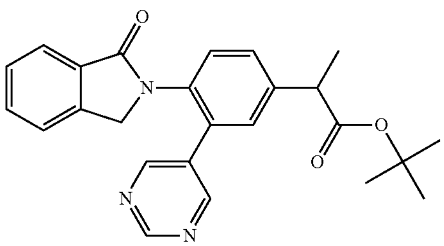 | ALB-112194 | | 1.098 |
| 119 | 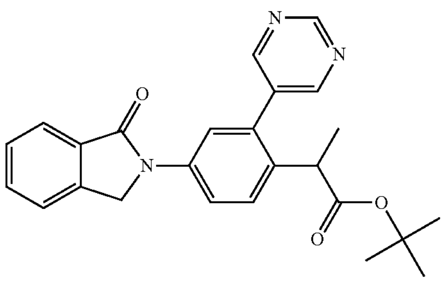 | ALB-112195 | | 1.061 |
| 120 | 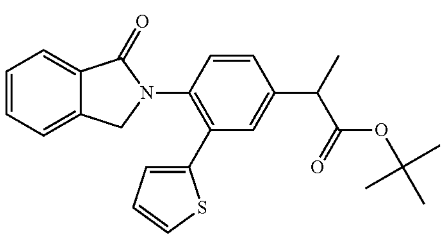 | ALB-112196 | | 1.095 |
| 121 | 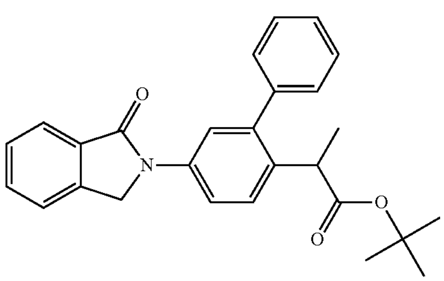 | ALB-112197 | | 1.069 |
| 122 | 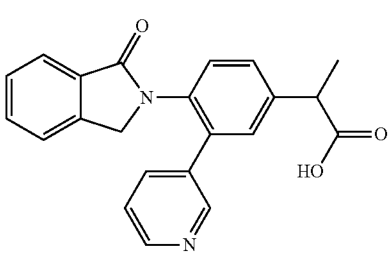 | ALB-112198 | | 1.119 |

TABLE 1-continued
| No. | STRUCTURE | Identifier | SMN Splice Reporter Assay (Example 10) Avg EC50 (uM) | Avg MaxFold Increase |
|---|---|---|---|---|
| 123 | 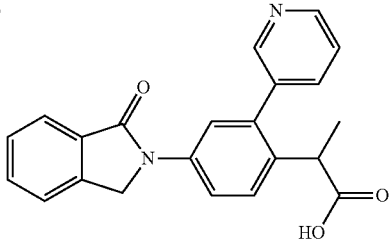 | ALB-112199 | | 1.083 |
| 124 | 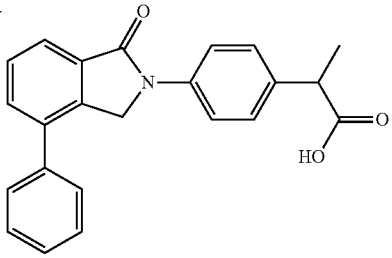 | ALB-112220 | | 1.223 |
| 125 | 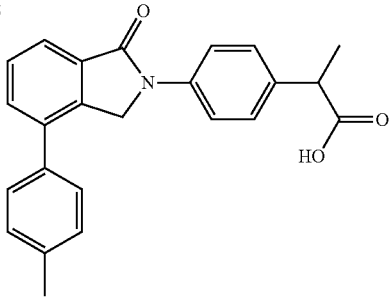 | ALB-112221 | | 1.326 |
| 126 | 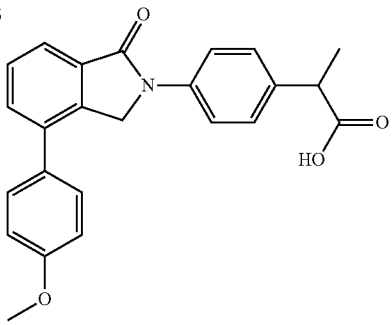 | ALB-112222 | | 1.415 |
| 127 | 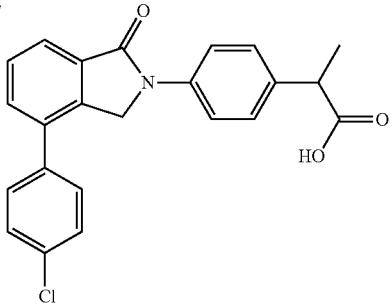 | ALB-112223 | 10.965 | 1.306 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 128 | 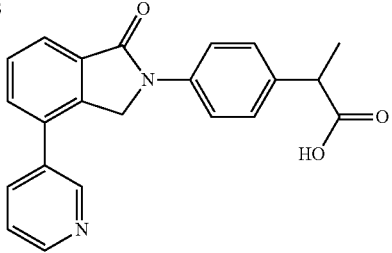 | ALB-112224 | | 1.301 |
| 129 | 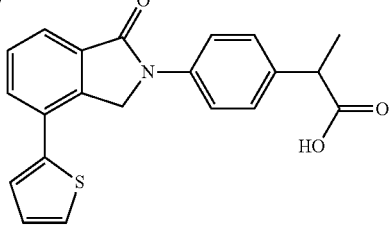 | ALB-112225 | | 1.068 |
| 130 | 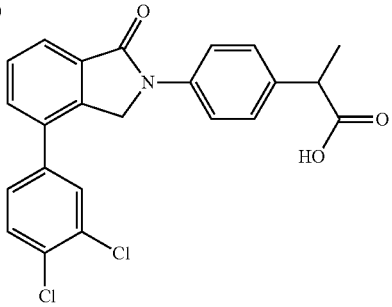 | ALB-112226 | 26.242 | 1.443 |
| 131 | 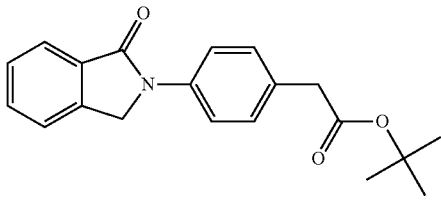 | ALB-112230 | | 1.099 |
| 132 | 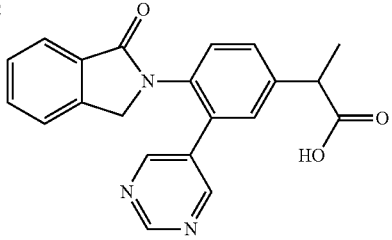 | ALB-112231 | | 1.085 |

TABLE 1-continued
| No. | STRUCTURE | Identifier | Avg EC50 (uM) | Avg MaxFold Increase |
|---|---|---|---|---|
| 133 | 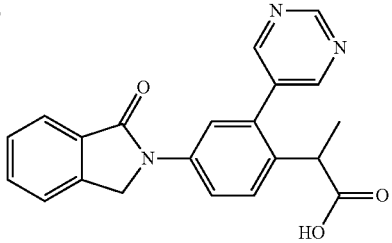 | ALB-112232 | | 1.048 |
| 134 | 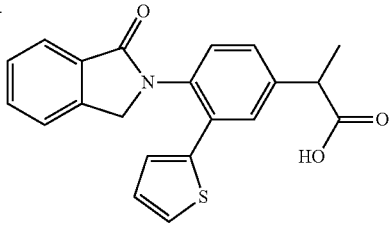 | ALB-112233 | | 1.027 |
| 135 | 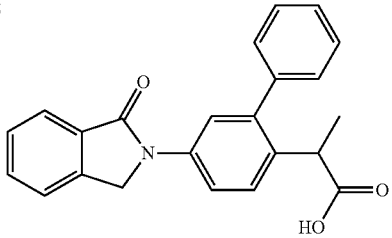 | ALB-112234 | 25.351 | 1.262 |
| 136 | 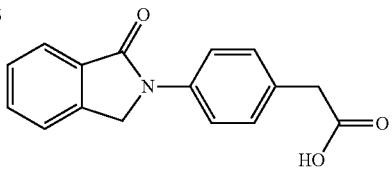 | ALB-112235 | | 0.941 |
| 137 | 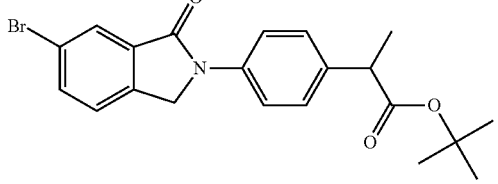 | ALB-112327 | 4.208 | 1.465 |
| 138 | 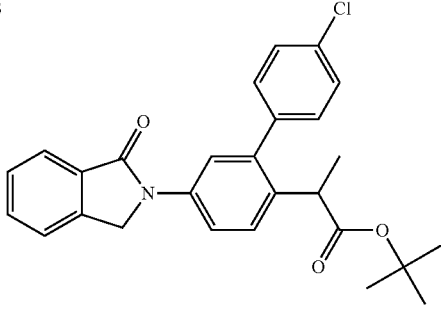 | ALB-112328 | | 1.043 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 139 | 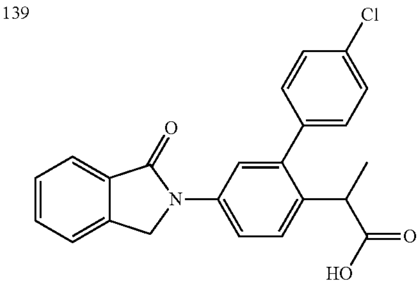 | ALB-112329 | | 1.091 |
| 140 | 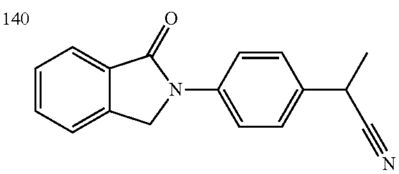 | ALB-112330 | 0.259 | 1.462 |
| 141 | 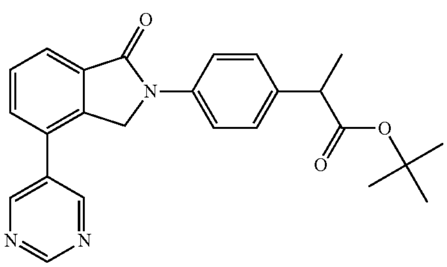 | ALB-112349 | | 1.064 |
| 142 | 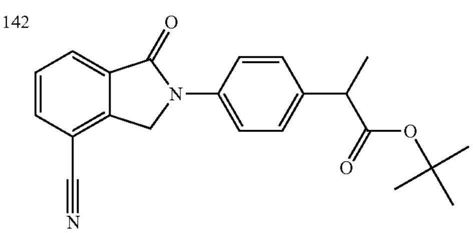 | ALB-112350 | | 1.182 |
| 143 | 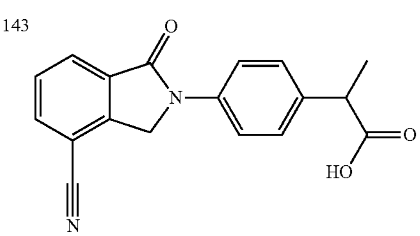 | ALB-112351 | | 1.205 |
| 144 | 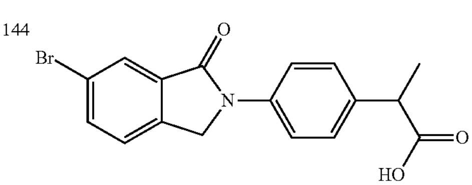 | ALB-112352 | 0.13 | 1118 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 145 | 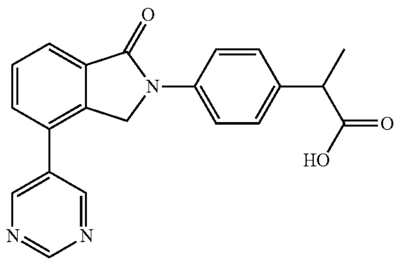 | ALB-112353 | 15.977 | 1.529 |
| 146 | 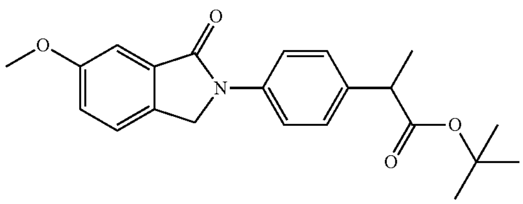 | ALB-112354 | 0.801 | 1.464 |
| 147 | 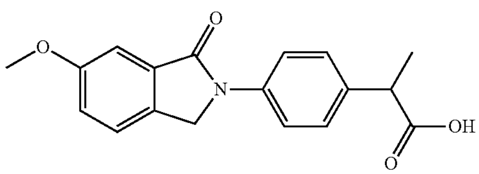 | ALB-112355 | 0.083 | 1.848 |
| 148 | 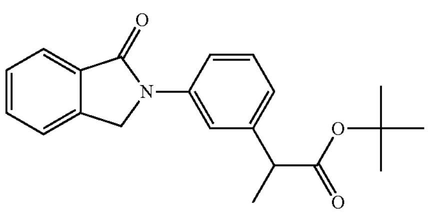 | ALB-112361 | | 1.095 |
| 149 | 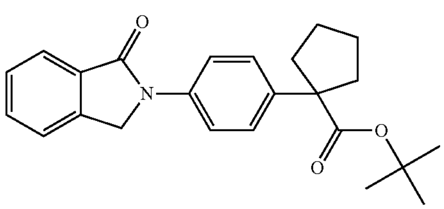 | ALB-112362 | | 1.053 |
| 150 | 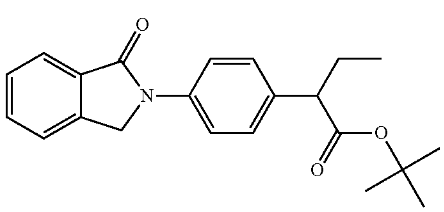 | ALB-112364 | 3.258 | 1.214 |
| 151 | 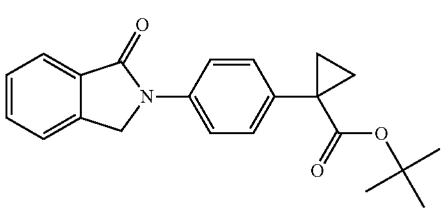 | ALB-112365 | 12.404 | 1.495 |

TABLE 1-continued
| No. | STRUCTURE | Identifier | Avg EC50 (uM) | Avg MaxFold Increase |
|---|---|---|---|---|
| 152 | 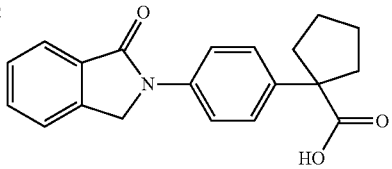 | ALB-112431 | | 1.208 |
| 153 | 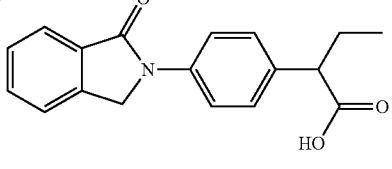 | ALB-112433 | 4.185 | 1.325 |
| 154 | 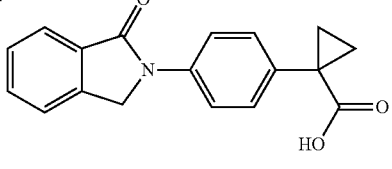 | ALB-112434 | | 1.28 |
| 155 | 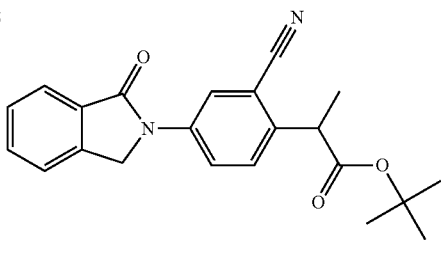 | ALB-112435 | 5.984 | 1.2 |
| 156 | 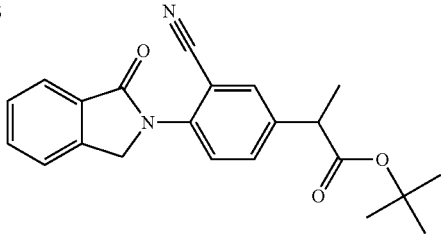 | ALB-112436 | | 1.071 |
| 157 | 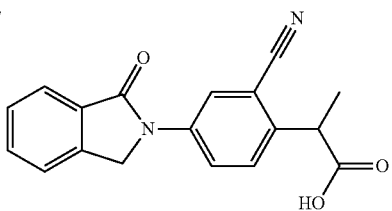 | ALB-112437 | | 1.09 |
| 158 | 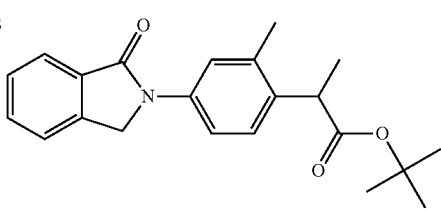 | ALB-112438 | 2.714 | 1.421 |

TABLE 1-continued

| No. | STRUCTURE | Identifier | SMN Splice Reporter Assay (Example 10) | |
| --- | --- | --- | --- | --- |
| | | | Avg EC50 (uM) | Avg MaxFold Increase |
| 159 | 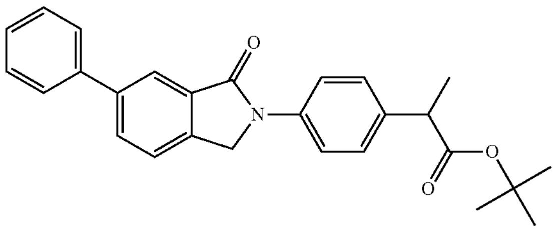 | ALB-112441 | | 1.084 |
| 160 | 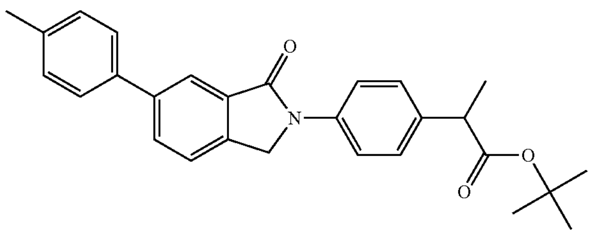 | ALB-112442 | | 1.115 |
| 161 | 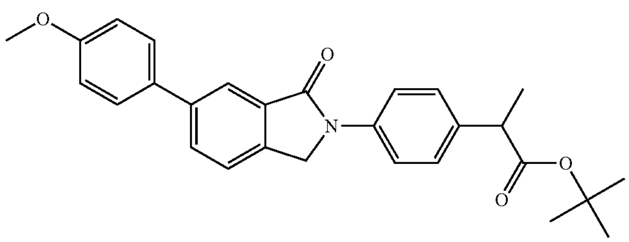 | ALB-112450 | | 1.091 |
| 162 | 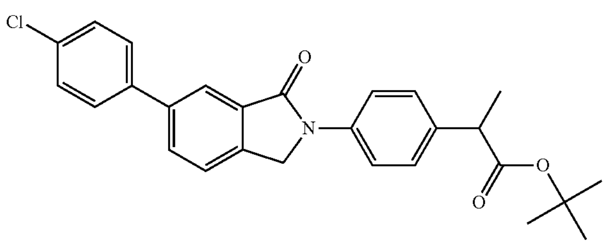 | ALB-112443 | | 1.068 |
| 163 | 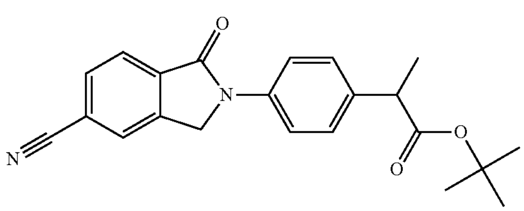 | ALB-112444 | 0.307 | 1.045 |
| 164 | 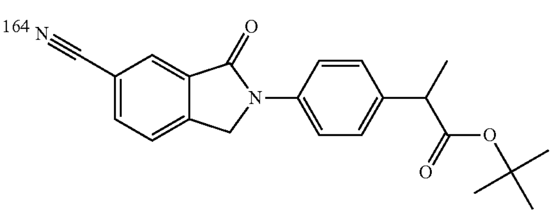 | ALB-112445 | | 1.133 |

TABLE 1-continued

| No. | STRUCTURE | Identifier | SMN Splice Reporter Assay (Example 10) Avg EC50 (uM) | Avg MaxFold Increase |
|---|---|---|---|---|
| 165 | 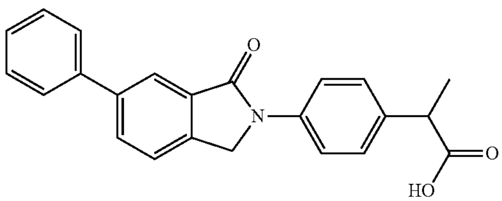 | ALB-112446 | 1.7 | 1.451 |
| 166 | 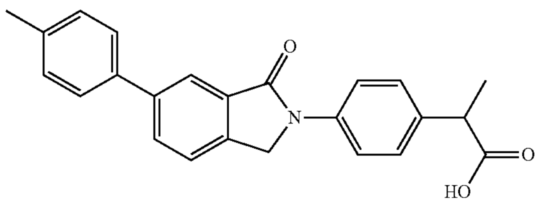 | ALB-112447 | 2.018 | 1.266 |
| 167 | 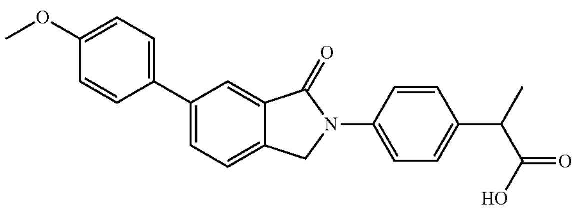 | ALB-112448 | 6.188 | 1.546 |
| 168 | 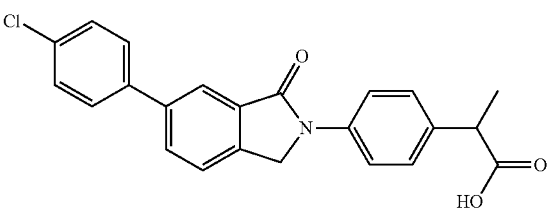 | ALB-112449 | | 1.157 |
| 169 | 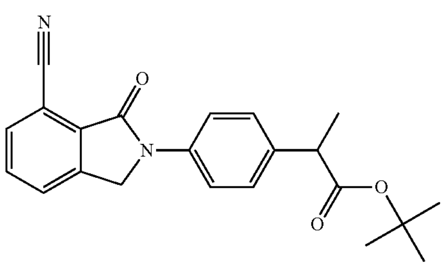 | ALB-112472 | | 1.123 |
| 170 | 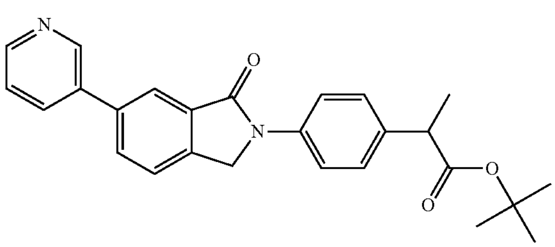 | ALB-112473 | 0.002 | 1.031 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 171 | 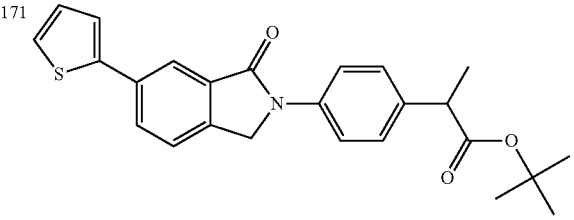 | ALB-112474 | | 1.176 |
| 172 | 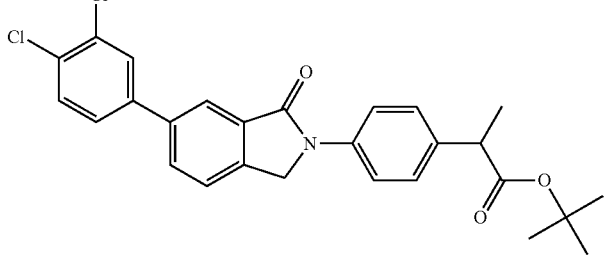 | ALB-112475 | 0.114 | 1.047 |
| 173 | 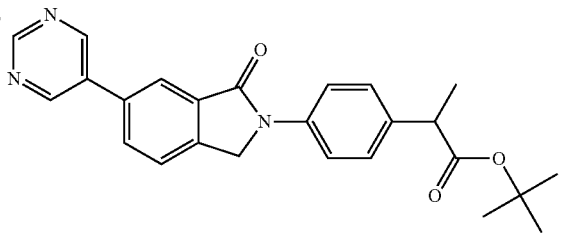 | ALB-112476 | | 1.081 |
| 174 | 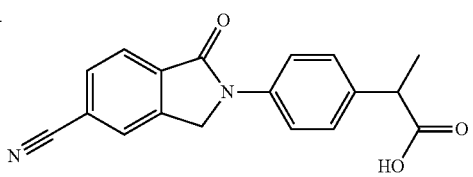 | ALB-112477 | 6.982 | 1.179 |
| 175 | 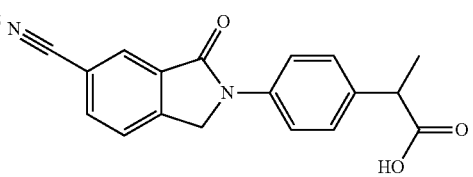 | ALB-112478 | 2.04 | 1.231 |
| 176 | 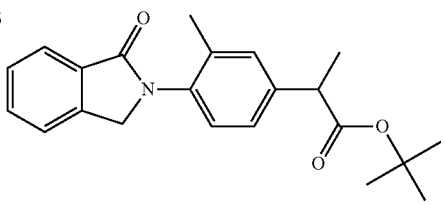 | ALB-112483 | | 1.034 |
| 177 | 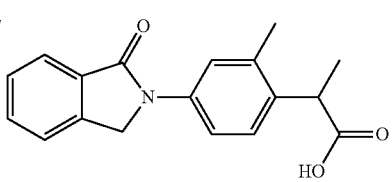 | ALB-112485 | | 1.304 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 178 | 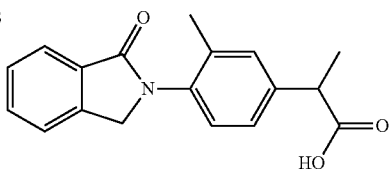 | ALB-112487 | | 1.173 |
| 179 | 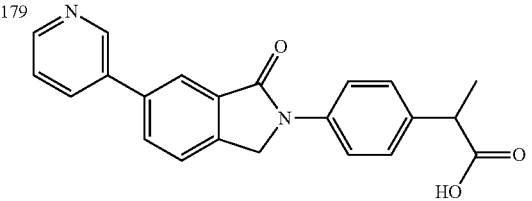 | ALB-112514 | | 1.252 |
| 180 | 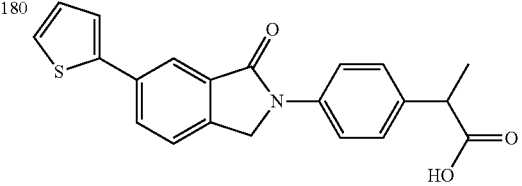 | ALB-112515 | 0.494 | 1.623 |
| 181 | 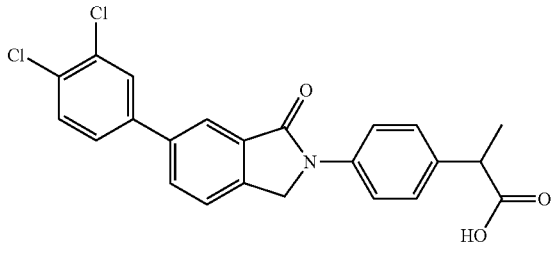 | ALB-112516 | | 1.199 |
| 182 | 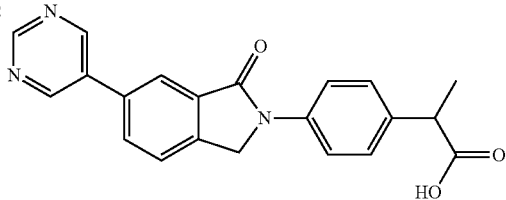 | ALB-112517 | | 1.255 |
| 183 | 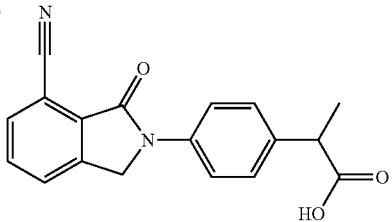 | ALB-112518 | | 1.117 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 184 | | ALB-112554 | | 1.062 |
| 185 | | ALB-112555 | 5.902 | 1.641 |
| 186 | | ALB-112556 | 0.146 | 1.565 |
| 187 | | ALB-112557 | 0.288 | 1.734 |
| 188 | | ALB-112837 | 8.538 | 1.396 |
| 189 | | ALB-112941 | 0.28 | 1.483 |
| 190 | | ALB-112954 | 0.33 | 1.617 |
| 191 | | ALB-113101 | 0.242 | 1.377 |

TABLE 1-continued

| No. | STRUCTURE | Identifier | SMN Splice Reporter Assay (Example 10) Avg EC50 (uM) | Avg MaxFold Increase |
|---|---|---|---|---|
| 192 | 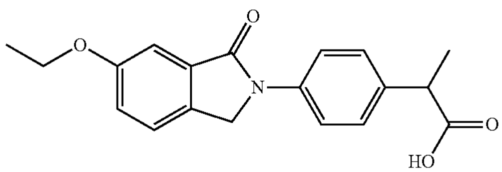 | ALB-113102 | 0.062 | 1.827 |
| 193 | 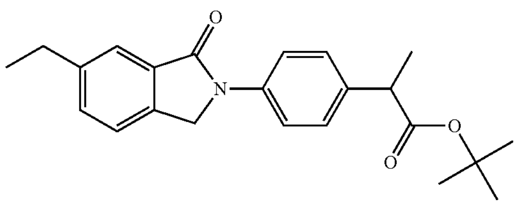 | ALB-113211 | 0.786 | 1.369 |
| 194 | 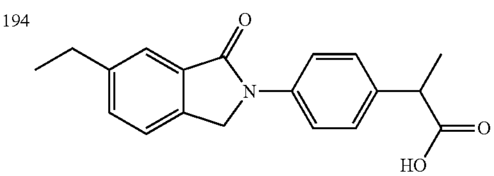 | ALB-113212 | 0.103 | 1.868 |
| 195 | 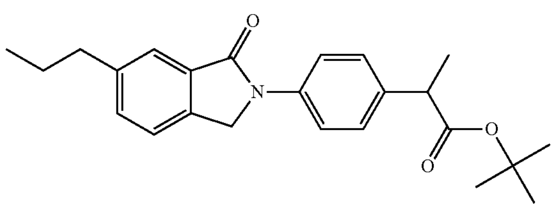 | ALB-113213 | 0.565 | 1.234 |
| 196 | 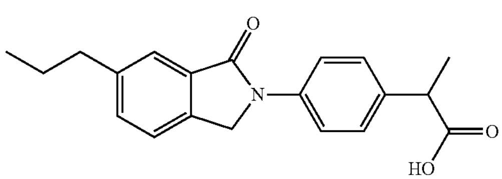 | ALB-113310 | 0.049 | 2.096 |
| 197 | 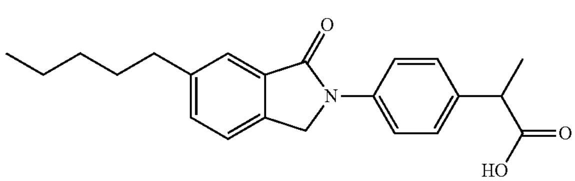 | ALB-113388 | 1.115 | 1.766 |
| 198 | 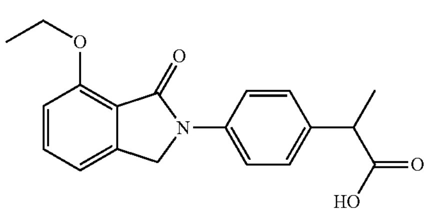 | ALB-113391 | 15.251 | 1.46 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 199 | 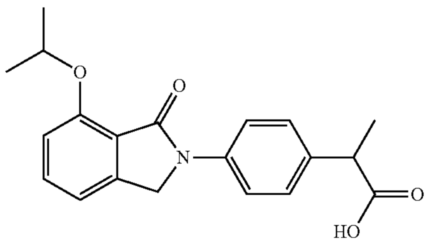 | ALB-113392 | 4.861 | 1.647 |
| 200 | 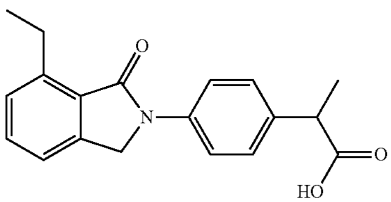 | ALB-113395 | 1.845 | 1.486 |
| 201 | 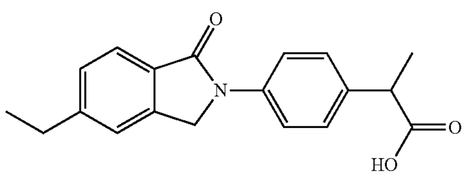 | ALB-113490 | 0.218 | 1.482 |
| 202 | 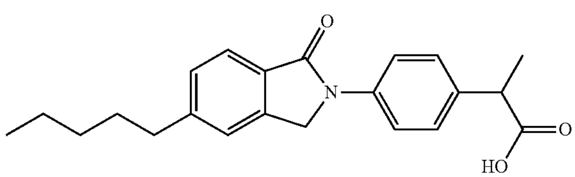 | ALB-113491 | | 1.124 |
| 203 | 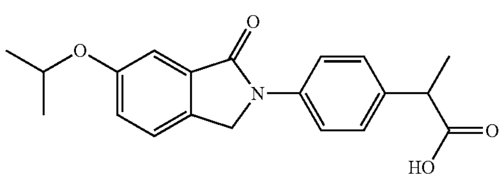 | ALB-113492 | 0.024 | 1.669 |
| 204 | 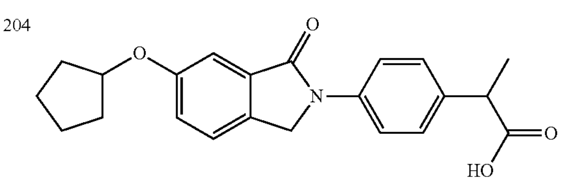 | ALB-113493 | 0.081 | 1.885 |
| 205 | 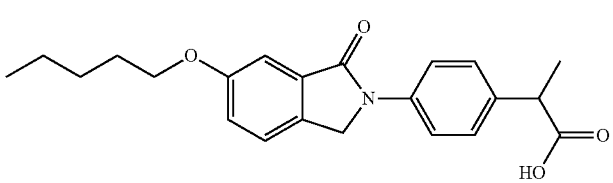 | ALB-113494 | 1.169 | 1.749 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 206 | 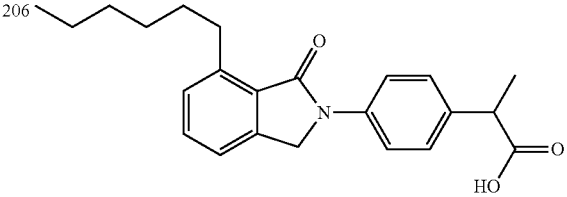 | ALB-113495 | 18.292 | 1.348 |
| 207 | 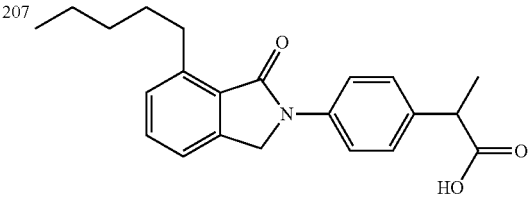 | ALB-113497 | | 1.178 |
| 208 | 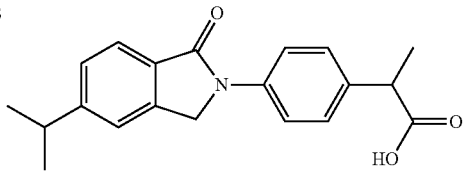 | ALB-113561 | | 1.205 |
| 209 | 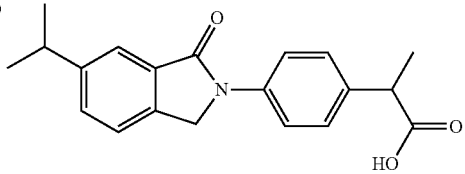 | ALB-113563 | 0.055 | 1.796 |
| 210 | 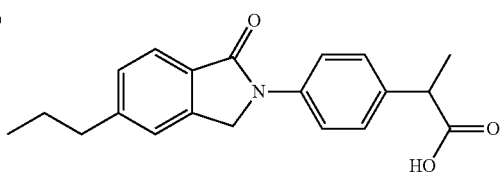 | ALB-113564 | | 1.055 |
| 211 | 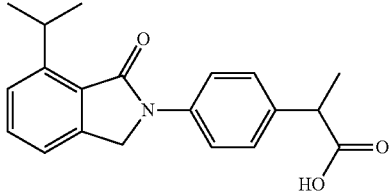 | ALB-113565 | | 1.185 |
| 212 | 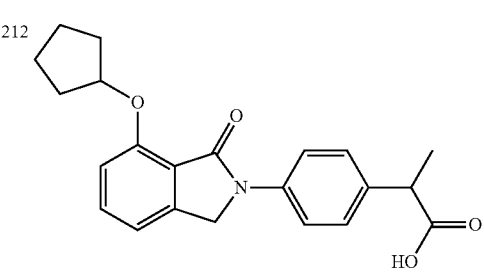 | ALB-113566 | 5.154 | 1.958 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 213 | 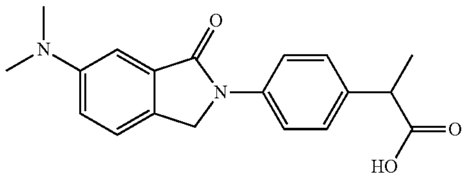 | ALB-113648 | 0.028 | 1.604 |
| 214 | 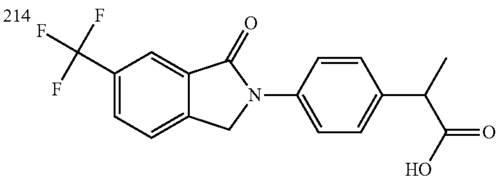 | ALB-113652 | 1.494 | 1.656 |
| 215 | 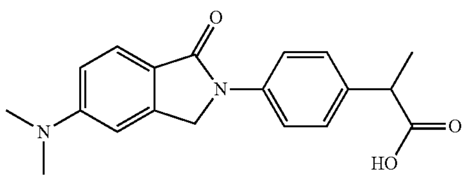 | ALB-113646 | | 1.051 |
| 216 | 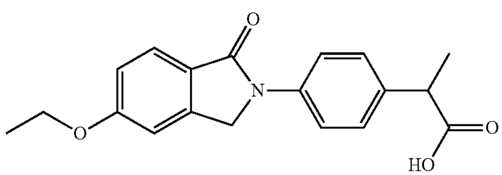 | ALB-113649 | | 1.132 |
| 217 | 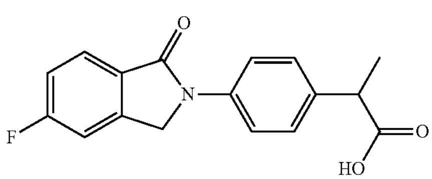 | ALB-113754 | 0.142 | 1.701 |
| 218 | 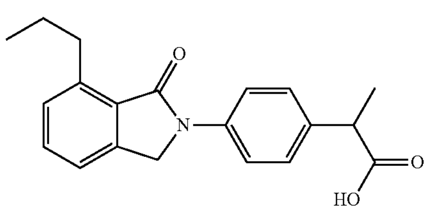 | ALB-113756 | 15.733 | 1.331 |
| 219 | 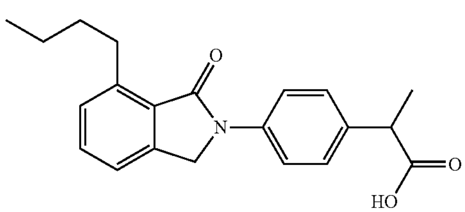 | ALB-113757 | | 1.182 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 220 | 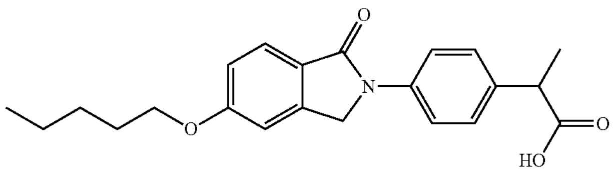 | ALB-113759 | 0.51 | 1.22 |
| 221 | 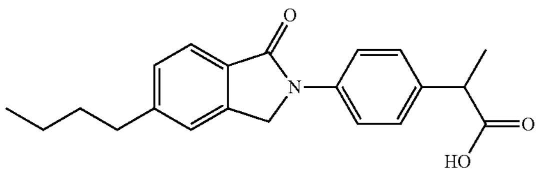 | ALB-113835 | | 1.149 |
| 222 | 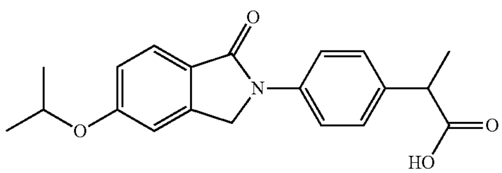 | ALB-113834 | | 1.098 |
| 223 | 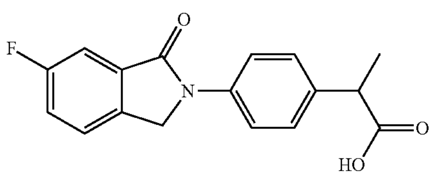 | ALB-113836 | 0.544 | 1.78 |
| 224 | 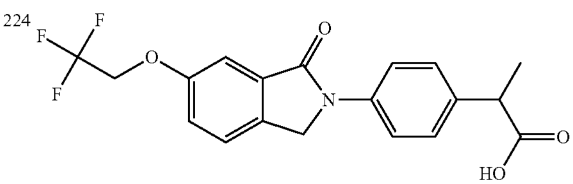 | ALB-113966 | 0.663 | 1.778 |
| 225 | 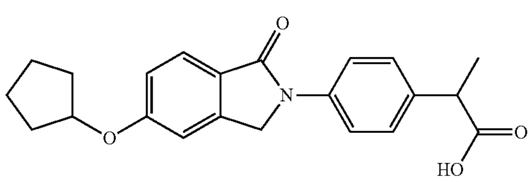 | ALB-113963 | | 1.141 |
| 226 | 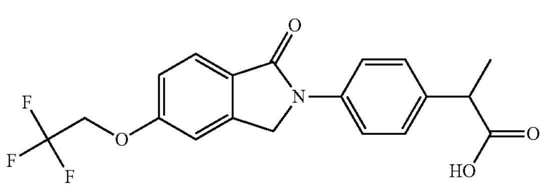 | ALB-113964 | | 1.08 |
| 227 | 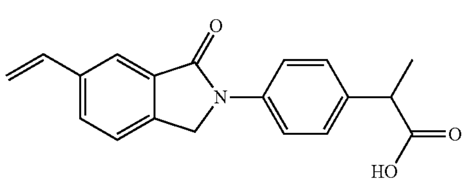 | ALB-113965 | 0.079 | 1.828 |

TABLE 1-continued
| No. | STRUCTURE | Identifier | Avg EC50 (uM) | Avg MaxFold Increase |
|---|---|---|---|---|
| 228 | 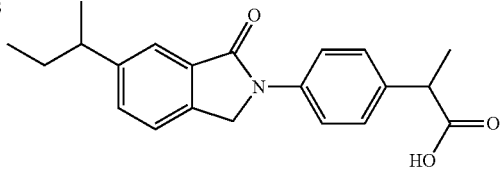 | ALB-114088 | 0.078 | 2.191 |
| 229 | 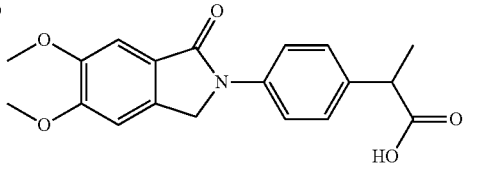 | ALB-114437 | | 1.201 |
| 230 | 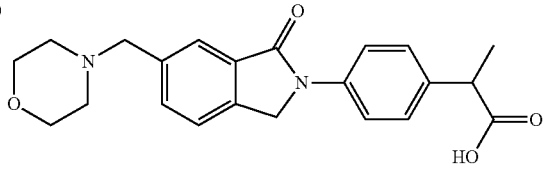 | ALB-114438 | 1.905 | 1.273 |
| 231 | 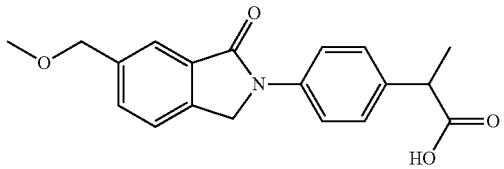 | ALB-114439 | 0.052 | 1.511 |
| 232 | 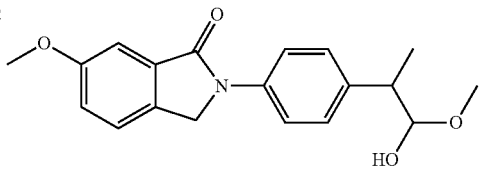 | ALB-114441 | 0.076 | 1.673 |
| 233 | 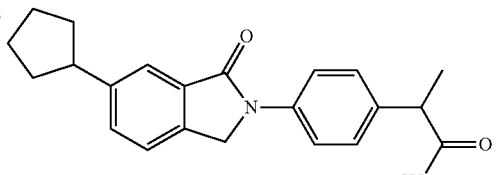 | ALB-114607 | 0.035 | 1.509 |
| 234 | 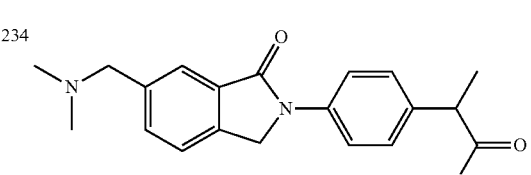 | ALB-114608 | | 1.228 |
| 235 | 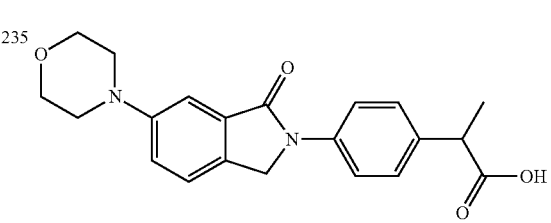 | ALB-114738a | | 1.084 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 236 | 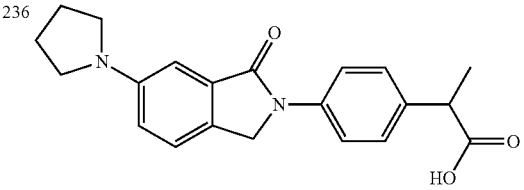 | ALB-114739a | 0.058 | 1.555 |
| 237 | 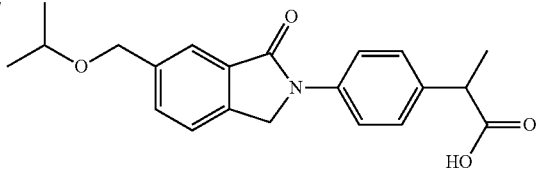 | ALB-114741 | 0:067 | 1.674 |
| 238 | 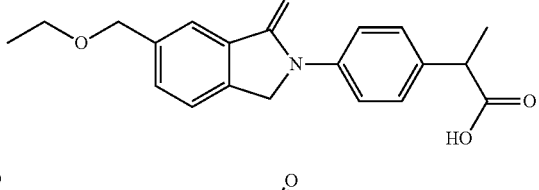 | ALB-114742 | 0.042 | 1.576 |
| 239 | 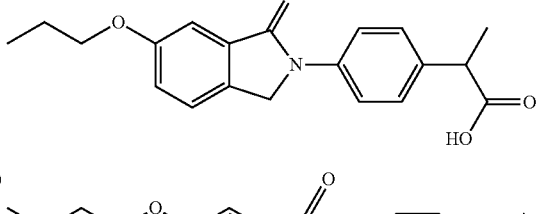 | ALB-114934 | 0.033 | 1.867 |
| 240 | 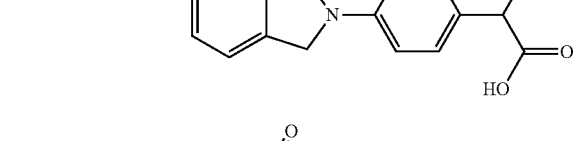 | ALB-115071 | 0.824 | 1.386 |
| 241 | 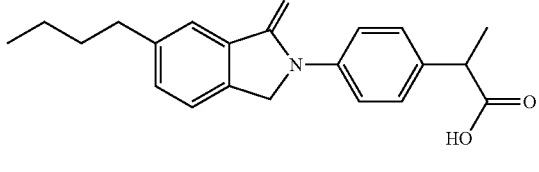 | ALB-115086 | 0.061 | 2.061 |
| 242 | 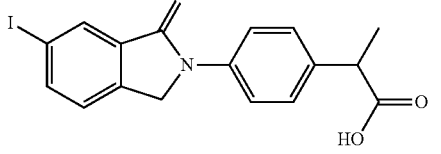 | ALB-115216 | 0.075 | 1.873 |
| 243 | 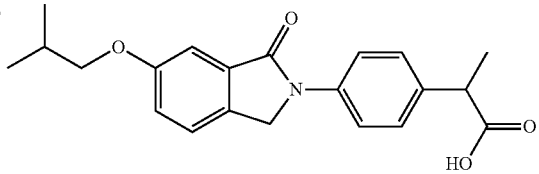 | ALB-115325 | 0.074 | 1.571 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 244 | 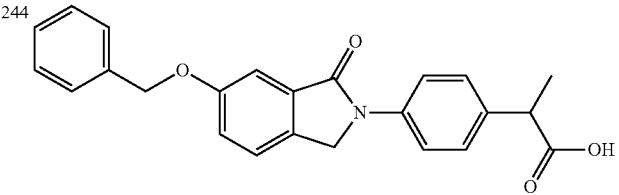 | ALB-115326 | | 1.241 |
| 245 | 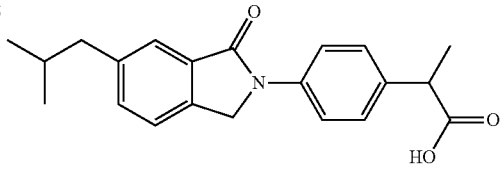 | ALB-115426 | 0.013 | 1.961 |
| 246 | 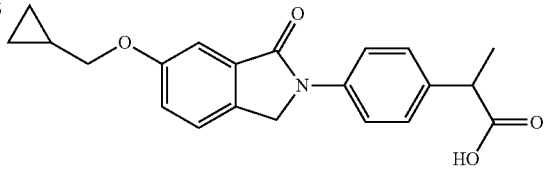 | ALB-115500 | 0.115 | 1.536 |
| 247 | 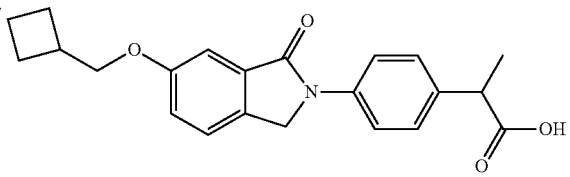 | ALB-115585 | 0.083 | 1.477 |
| 248 | 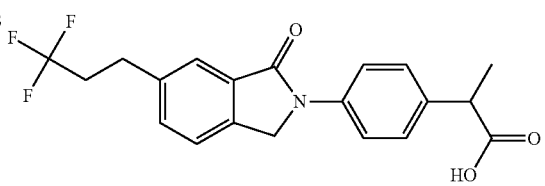 | ALB-115588 | 0.356 | 1.704 |
| 249 | 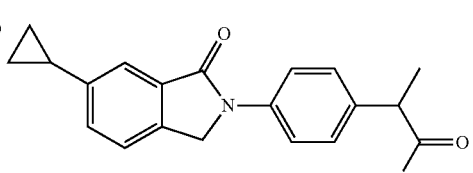 | ALB-115716 | 0.029 | 1.593 |
| 250 | 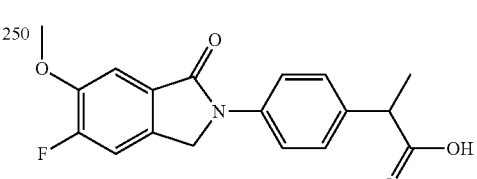 | ALB-119048 | 0.255 | 1.536 |
| 251 | 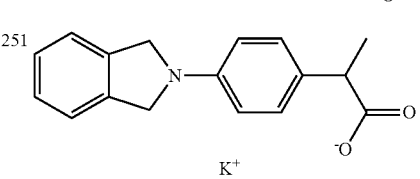 | ALB-112227 | 1.424 | 1.504 |

TABLE 1-continued

| No. | STRUCTURE | Identifier | SMN Splice Reporter Assay (Example 10) | |
| --- | --- | --- | --- | --- |
| | | | Avg EC50 (uM) | Avg MaxFold Increase |
| 252 | 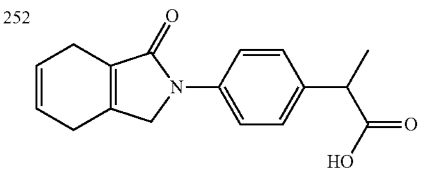 | ALB-112896 | 1.011 | 1.578 |
| 253 | 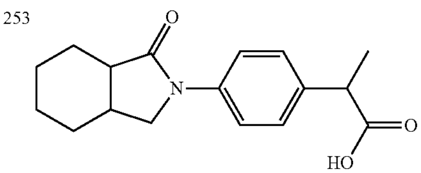 | ALB-112901 | 5.815 | 1.487 |
| 254 | 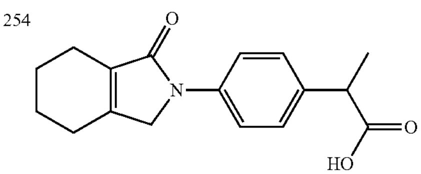 | ALB-112951 | 0.279 | 1.792 |
| 255 | 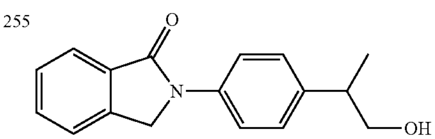 | ALB-113309 | 0.144 | 1.194 |
| 256 | 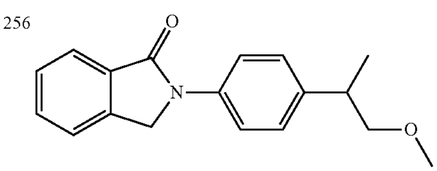 | ALB-113389 | 0.179 | 1.337 |
| 257 | 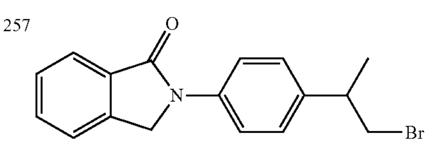 | ALB-113651 | 0.209 | 1.437 |
| 258 | 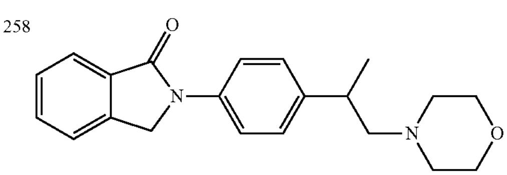 | ALB-113758 | 1.4 | 1.292 |
| 259 | 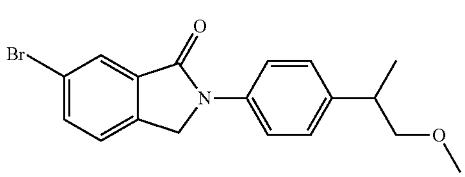 | ALB-113967 | 0.159 | 1.538 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 260 | 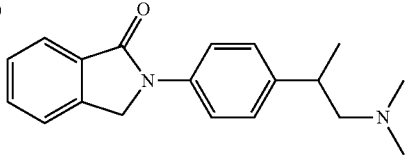 | ALB-113968 | 6.026 | 1.373 |
| 261 | 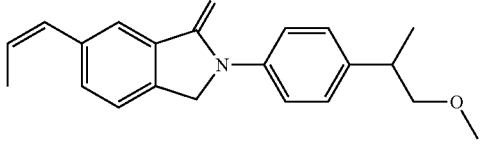 | ALB-114089 | 0.902 | 1.548 |
| 262 | 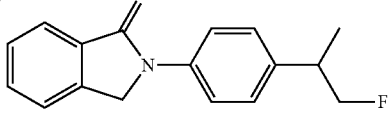 | ALB-114090 | 0.214 | 1.465 |
| 263 | 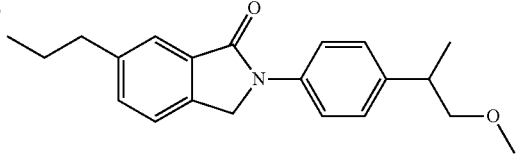 | ALB-114091 | 0.699 | 1.458 |
| 264 | 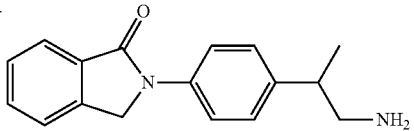 | ALB-114604 | 0.303 | 1.394 |
| 265 | 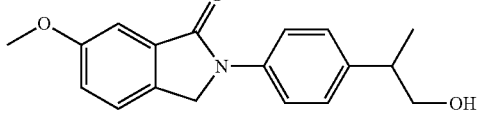 | ALB-114606 | 0.181 | 1.311 |
| 266 | 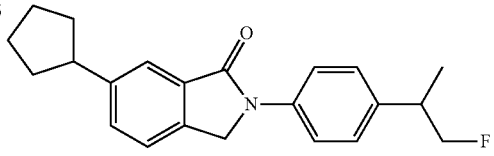 | ALB-114740 | 0.822 | 1.223 |
| 267 | 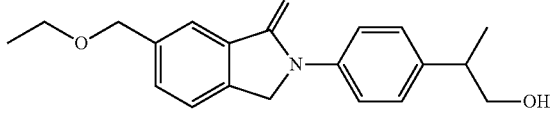 | ALB-114743 | 0.448 | 1.366 |
| 268 | 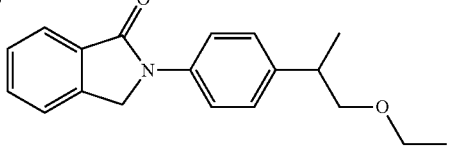 | ALB-114744 | | 1.179 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 269 | 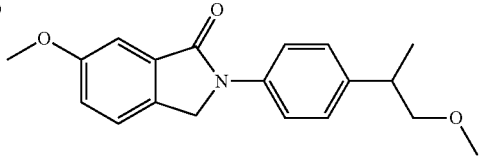 | ALB-114783 | 0.186 | 1.372 |
| 270 | 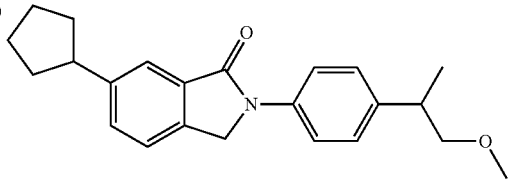 | ALB-114845 | | 1.151 |
| 271 | 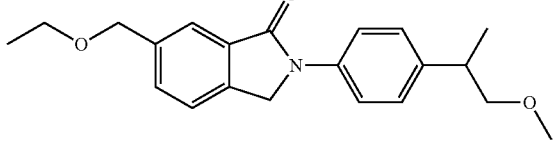 | ALB-114846 | 0.493 | 1.296 |
| 272 | 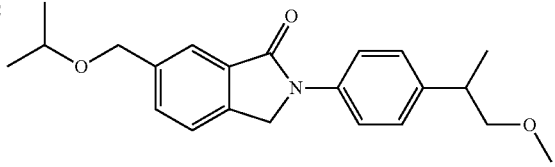 | ALB-114847 | | 1.225 |
| 273 | 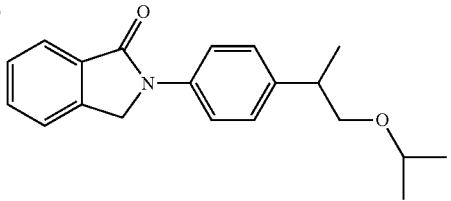 | ALB-114935 | 0.977 | 1.257 |
| 274 | 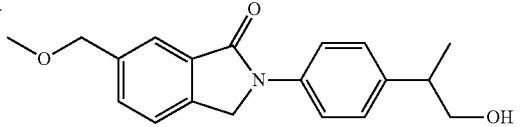 | ALB-114941 | 0.299 | 1.351 |
| 275 | 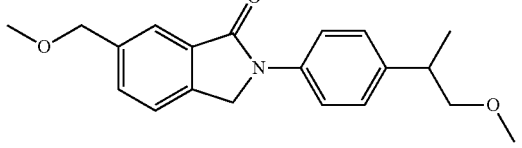 | ALB-114942 | 0.217 | 1.331 |
| 276 | 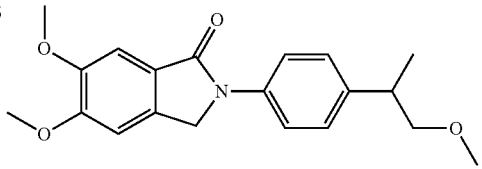 | ALB-114943 | 1.315 | 1.348 |

TABLE 1-continued
| No. | STRUCTURE | Identifier | SMN Splice Reporter Assay (Example 10) | |
| --- | --- | --- | --- | --- |
| | | | Avg EC50 (uM) | Avg MaxFold Increase |
| 277 | 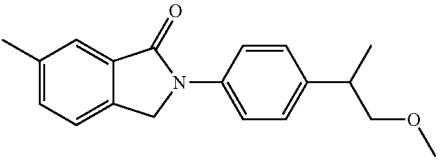 | ALB-115072 | 0.032 | 1.28 |
| 278 | 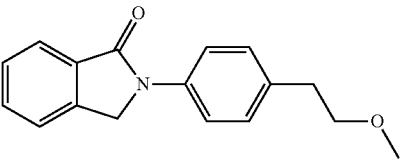 | ALB-115073 | | 1.191 |
| 279 | 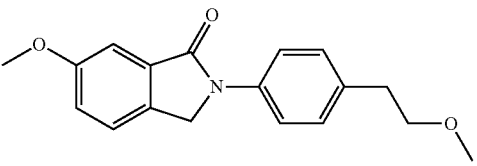 | ALB-115217 | | 1.259 |
| 280 | 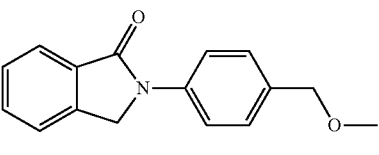 | ALB-115323 | | 1.104 |
| 281 | 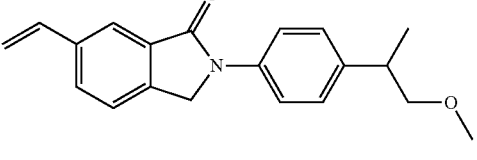 | ALB-115327 | 0.076 | 1.43 |
| 282 | 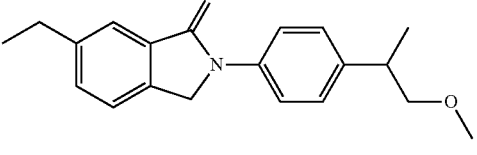 | ALB-115328 | 0.298 | 1.497 |
| 283 | 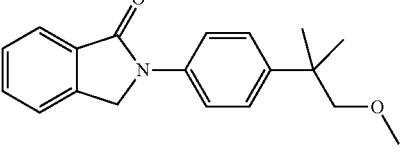 | ALB-115427 | | 1.311 |
| 284 | 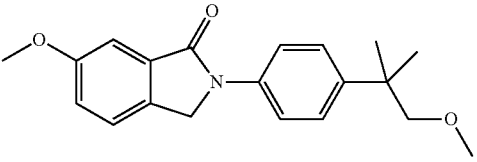 | ALB-115706 | 0.66 | 1.259 |

TABLE 1-continued

| No. | STRUCTURE | Identifier | SMN Splice Reporter Assay (Example 10) Avg EC50 (uM) | Avg MaxFold Increase |
|---|---|---|---|---|
| 285 | 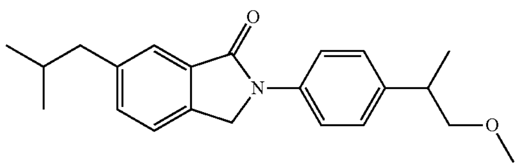 | ALB-115976 | 0.179 | 1.288 |
| 286 | 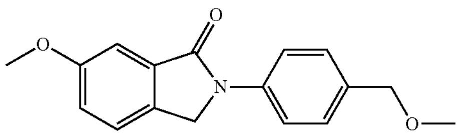 | ALB-116067 | | 1.238 |
| 287 | 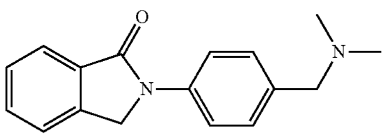 | ALB-116255 | 0.05 | 1.095 |
| 288 | 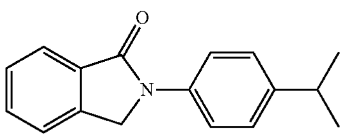 | ALB-114274 | 0.052 | 1.397 |
| 289 | 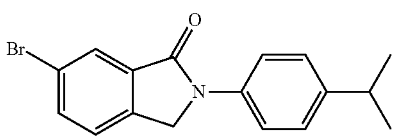 | ALB-114901 | 0.193 | 1.521 |
| 290 | 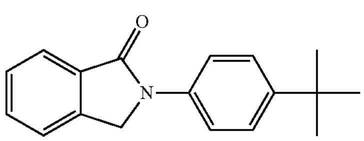 | ALB-114936 | 0.131 | 1.41 |
| 291 | 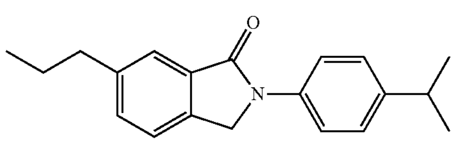 | ALB-114939 | 0.298 | 1.431 |
| 292 | 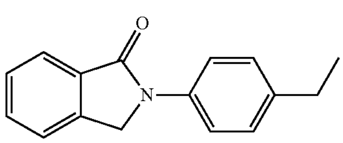 | ALB-114940 | 0.097 | 1.365 |
| 293 | 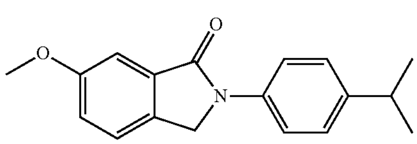 | ALB-115069 | 0.081 | 1.496 |
| 294 | 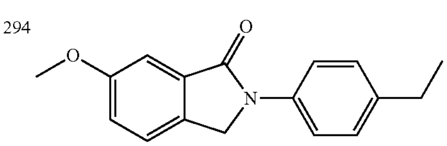 | ALB-115085 | 0.058 | 1.468 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 295 | 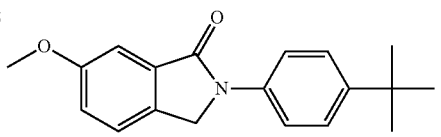 | ALB-115210 | 0.324 | 1.468 |
| 296 | 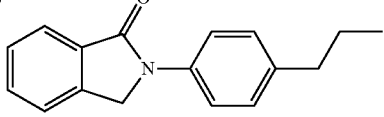 | ALB-115499 | 0.083 | 1.274 |
| 297 | 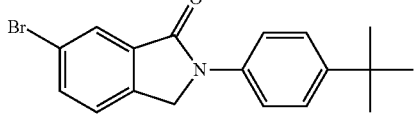 | ALB-115583 | 0.184 | 1.368 |
| 298 | 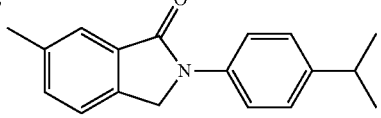 | ALB-115586 | 0.097 | 1.325 |
| 299 | 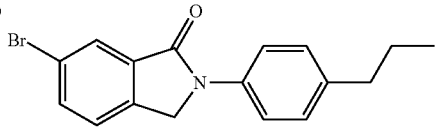 | ALB-115589 | 0.143 | 1.394 |
| 300 | 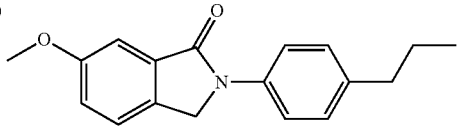 | ALB-115708 | | 1.103 |
| 301 | 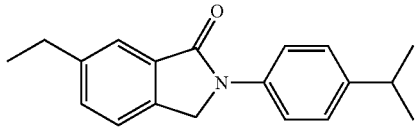 | ALB-115713 | 0.061 | 1.366 |
| 302 | 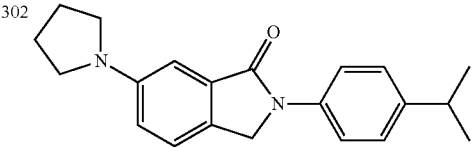 | ALB-115715 | | 1.058 |
| 303 | 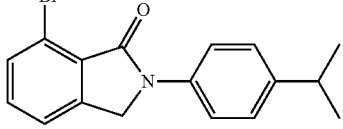 | ALB-115801 | 0.144 | 1.454 |
| 304 | 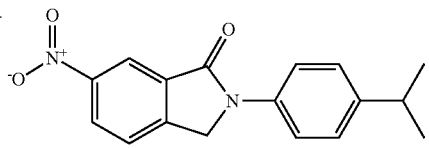 | ALB-115804 | 0.624 | 1.352 |

US 8,110,681 B2
111 112
TABLE 1-continued
| | | | SMN Splice Reporter Assay (Example 10) | |
|---|---|---|---|---|
| No. | STRUCTURE | Identifier | Avg EC50 (uM) | Avg MaxFold Increase |
| 305 | 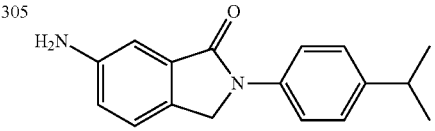 | ALB-115805 | 0.099 | 1.418 |
| 306 | 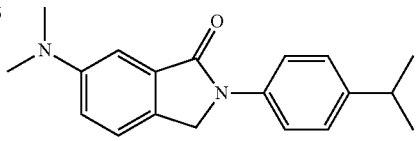 | ALB-115806 | 0.041 | 1.465 |
| 307 | 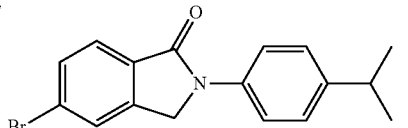 | ALB-115810 | 0.145 | 1.44 |
| 308 | 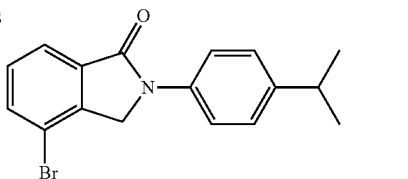 | ALB-115811 | | 1.156 |
| 309 | 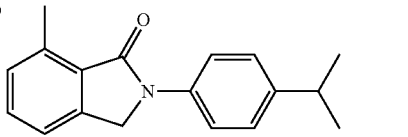 | ALB-115812 | 0.163 | 1.347 |
| 310 | 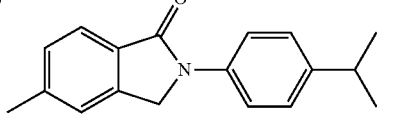 | ALB-115948 | 0.03 | 1.418 |
| 311 | 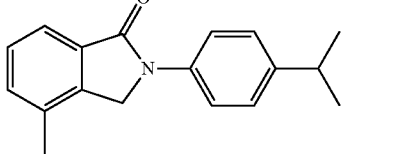 | ALB-115947 | 0.114 | 1.391 |
| 312 | 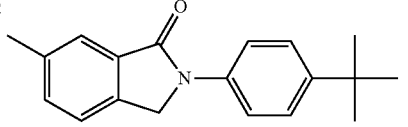 | ALB-116068 | 0.051 | 1.347 |
| 313 | 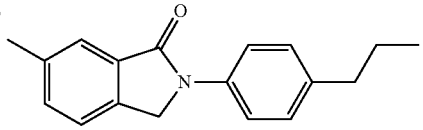 | ALB-116071 | 0.016 | 1.35 |

US 8,110,681 B2
TABLE 1-continued
| No. | STRUCTURE | Identifier | SMN Splice Reporter Assay (Example 10) Avg EC50 (uM) | Avg MaxFold Increase |
|---|---|---|---|---|
| 314 | 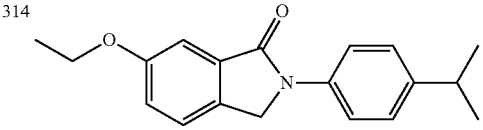 | ALB-116074 | 0.31 | 1.506 |
| 315 | 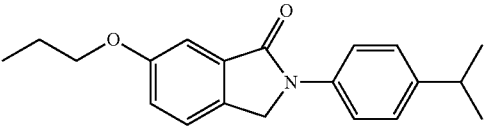 | ALB-116075 | 0.188 | 1.258 |
| 316 | 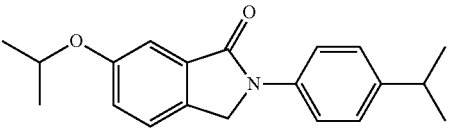 | ALB-116076 | 0.072 | 1.352 |
| 317 | 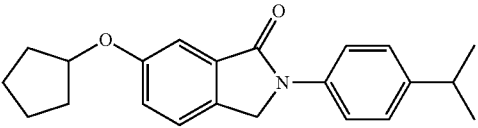 | ALB-116077 | | 1.176 |
| 318 | 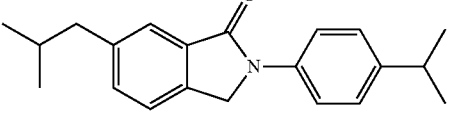 | ALB-116245 | 0.219 | 1.356 |
| 319 | 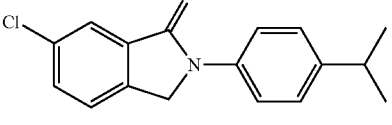 | ALB-116246 | 0.031 | 1.35 |
| 320 | 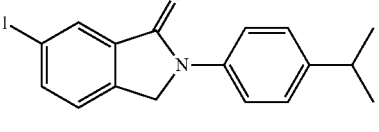 | ALB-116247 | 0.277 | 1.515 |
| 321 | 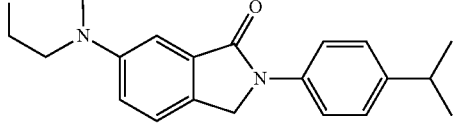 | ALB-116368 | | 1.081 |
| 322 | 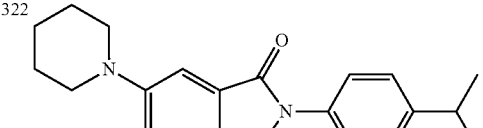 | ALB-116418 | | 1.149 |

TABLE 1-continued
| No. | STRUCTURE | Identifier | Avg EC50 (uM) | Avg MaxFold Increase |
|---|---|---|---|---|
| 323 | 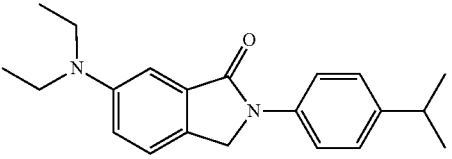 | ALB-116639 | 0.121 | 1.188 |
| 324 | 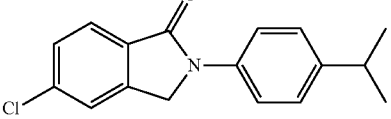 | ALB-116932 | 0.081 | 1.45 |
| 325 | 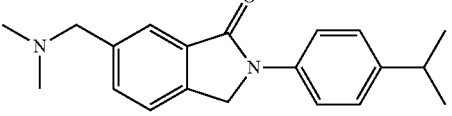 | ALB-116934 |  | 1.053 |
| 326 | 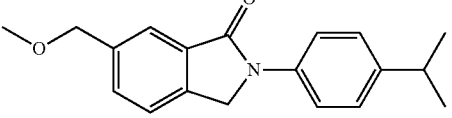 | ALB-116935 | 0.078 | 1.521 |
| 327 | 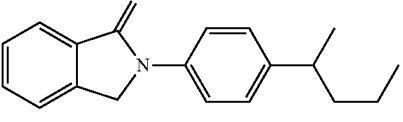 | ALB-117045 | 0.07 | 1.247 |
| 328 | 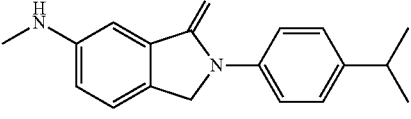 | ALB-117046 | 0.09 | 1.44 |
| 329 | 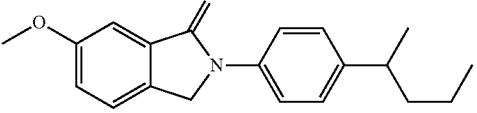 | ALB-117451 | 2.906 | 1.735 |
| 330 | 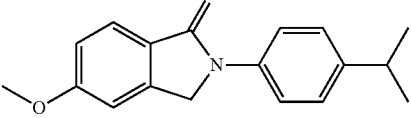 | ALB-117453 | 0.18 | 1.276 |
| 331 | 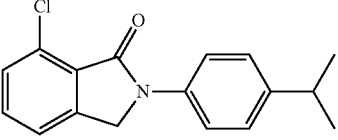 | ALB-117454 | 0.47 | 1.509 |
| 332 | 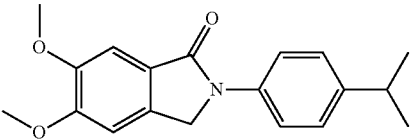 | ALB-117672 | 0.319 | 1.472 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 333 | 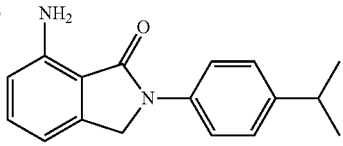 | ALB-117574 | 0.163 | 1.727 |
| 334 | 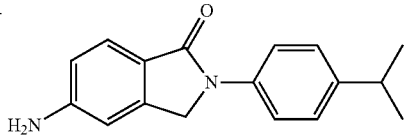 | ALB-117747 | 0.034 | 1.486 |
| 335 | 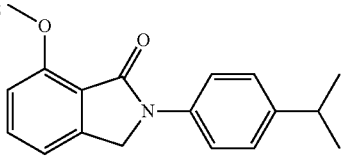 | ALB-117748 | 0.166 | 1.343 |
| 336 | 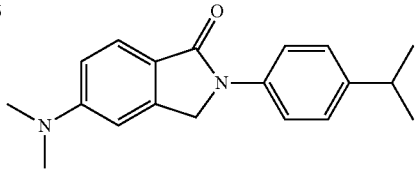 | ALB-117752 | 0.042 | 1.376 |
| 337 | 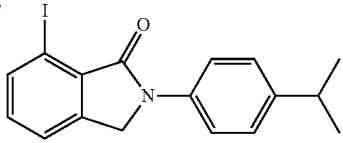 | ALB-117753 | 0.183 | 1.602 |
| 338 | 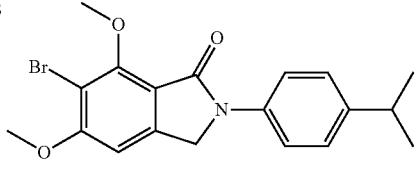 | ALB-117901 | | 1.067 |
| 339 | 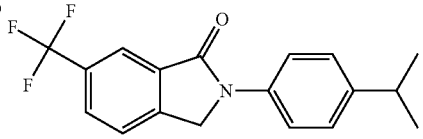 | ALB-117902 | 1.103 | 1.573 |
| 340 | 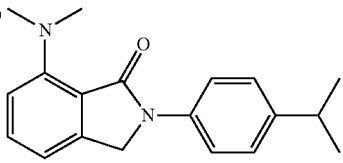 | ALB-117904 | 4.37 | 1.46 |
| 341 | 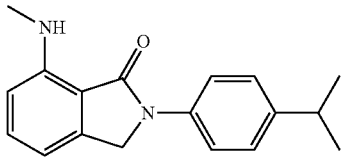 | ALB-117905 | 0.414 | 1.552 |

TABLE 1-continued
| No. | STRUCTURE | Identifier | Avg EC50 (uM) | Avg MaxFold Increase |
|---|---|---|---|---|
| 342 | 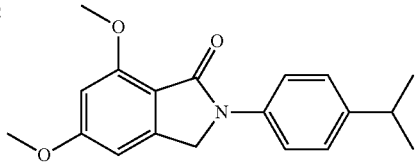 | ALB-118034 | 0.447 | 1.302 |
| 343 | 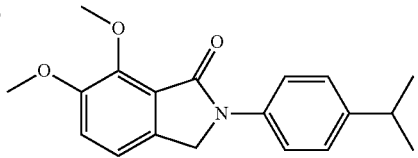 | ALB-118036 | 2.668 | 1.288 |
| 344 | 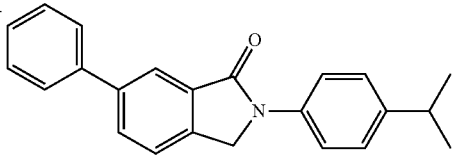 | ALB-118037 | 0.937 | 1.336 |
| 345 | 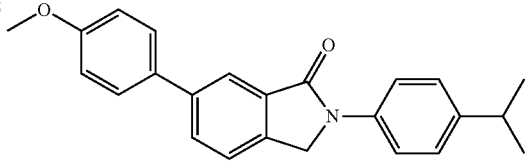 | ALB-118038 | | 1.077 |
| 346 | 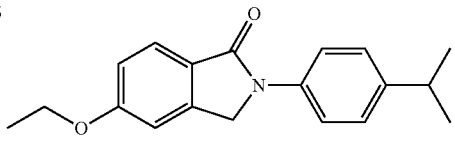 | ALB-118276 | | 1.047 |
| 347 | 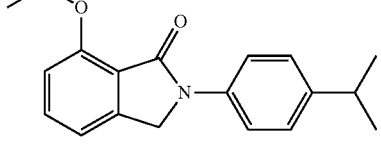 | ALB-118278 | 1.376 | 1.5 |
| 348 | 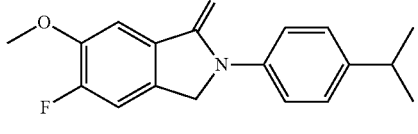 | ALB-118413 | 0.119 | 1.385 |
| 349 | 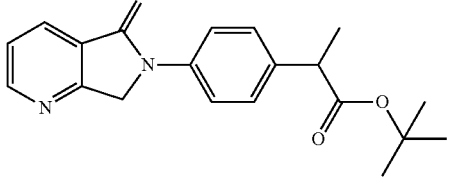 | ALB-112087 | | 1.052 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 350 | 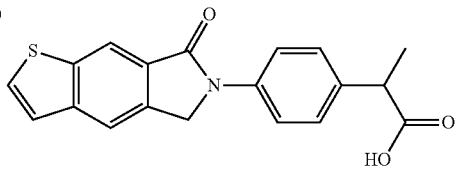 | ALB-112228 | 0.669 | 1.272 |
| 351 | 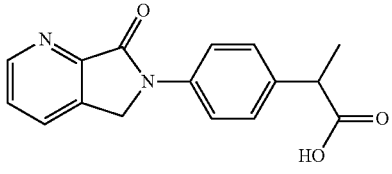 | ALB-112229a | | 1.13 |
| 352 | 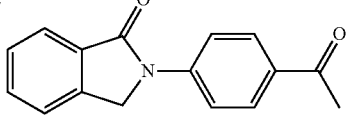 | ALB-112360 | 0.424 | 1.137 |
| 353 | 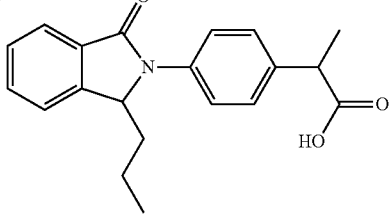 | ALB-111795 | 25.81 | 1.411 |
| 354 | 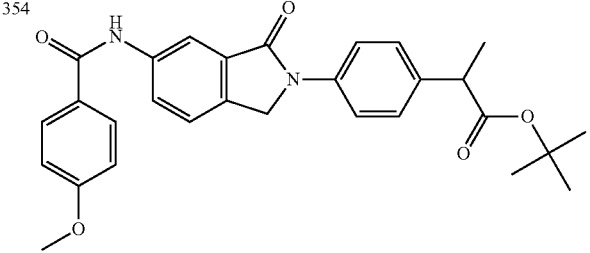 | ALB-111954 | | 1.039 |
| 355 | 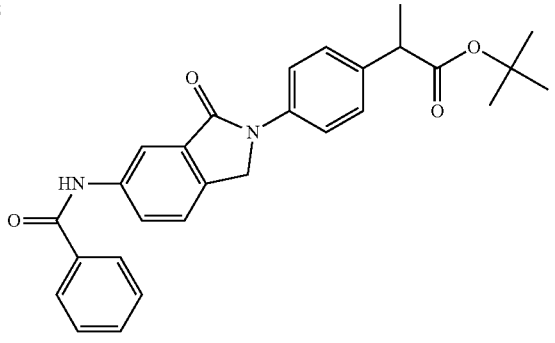 | ALB-111958 | | 1.057 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 356 | 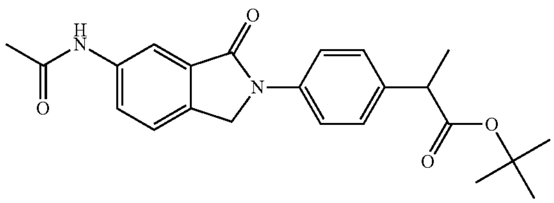 | ALB-111960 | 6.622 | 1.237 |
| 357 | 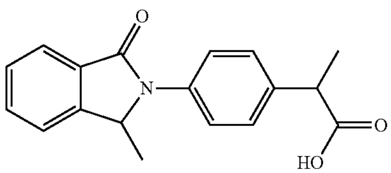 | ALB-111964 | 1.425 | 1.627 |
| 358 | 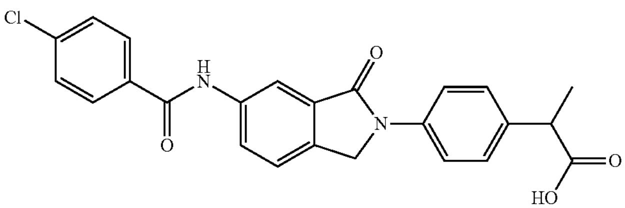 | ALB-111983 | | 1.065 |
| 359 | 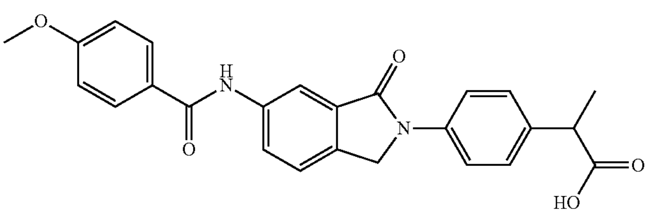 | ALB-111984 | 9.465 | 1.188 |
| 360 | 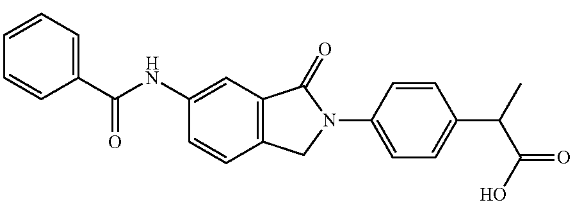 | ALB-111986 | | 1.056 |
| 361 | 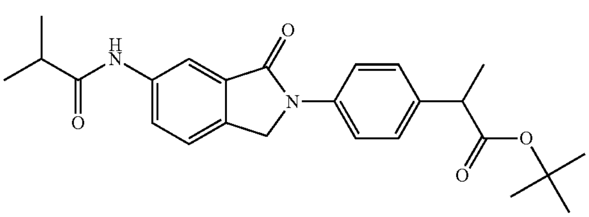 | ALB-111989 | | 1.065 |
| 362 | 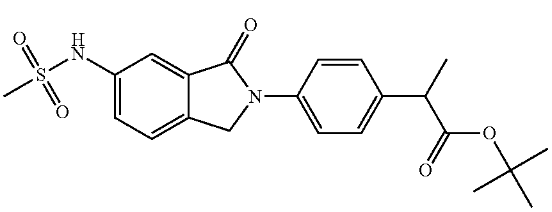 | ALB-111997 | 0.175 | 1,006 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 363 | 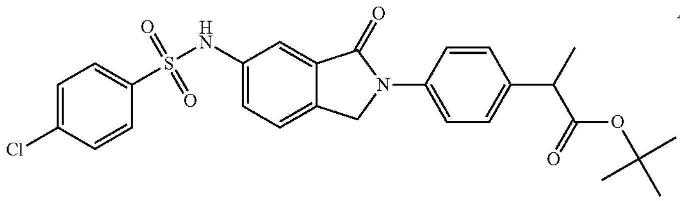 | ALB-112070 | | 1.106 |
| 364 | 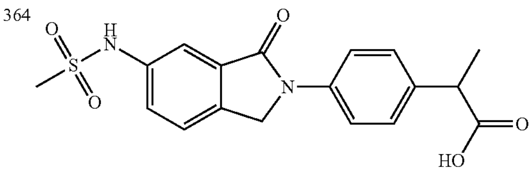 | ALB-112071 | | 1.068 |
| 365 | 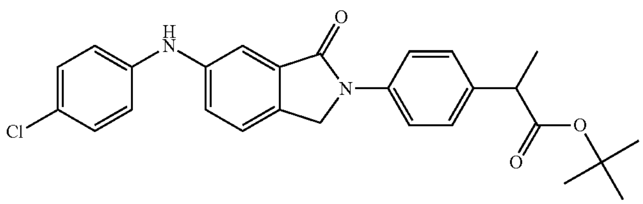 | ALB-112166 | | 1.036 |
| 366 | 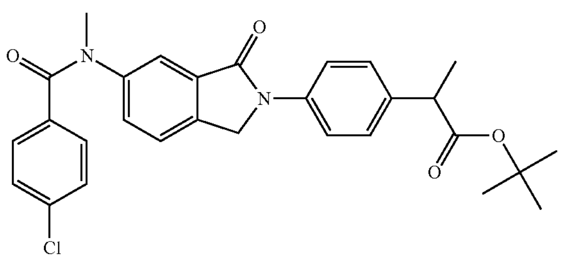 | ALB-112167 | | 1.012 |
| 367 | 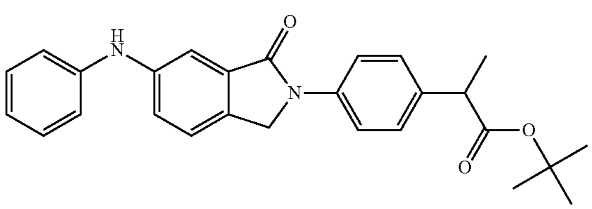 | ALB-112168 | | 1.153 |
| 368 | 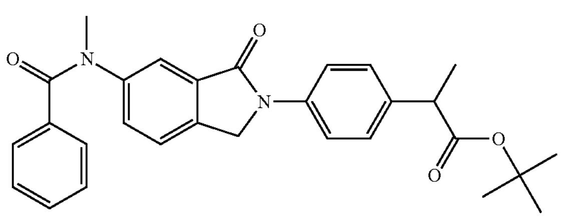 | ALB-112169 | | 1.068 |
| 369 | 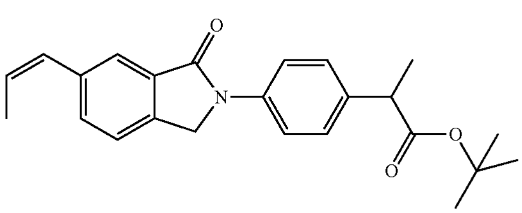 | ALB-113000 | 3.736 | 1.309 |

TABLE 1-continued

| No. | STRUCTURE | Identifier | Avg EC50 (uM) | Avg MaxFold Increase |
|---|---|---|---|---|
| 370 | 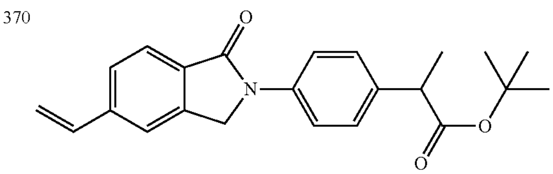 | ALB-113100 | 0.101 | 1.053 |
| 371 | 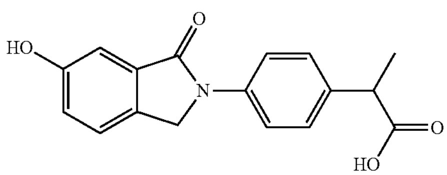 | ALB-113103 | | 1.041 |
| 372 | 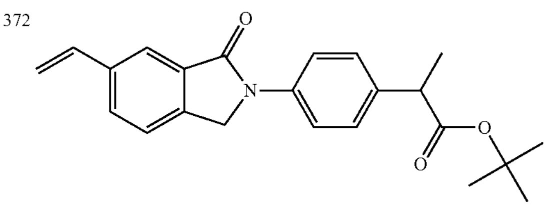 | ALB-113210 | 2.877 | 1.151 |
| 373 | 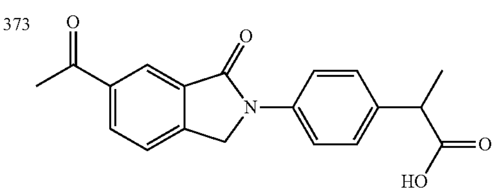 | ALB-113387 | 0.05 | 1.175 |
| 374 | 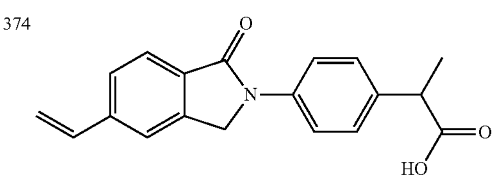 | ALB-113390 | 10.413 | 1.295 |
| 375 | 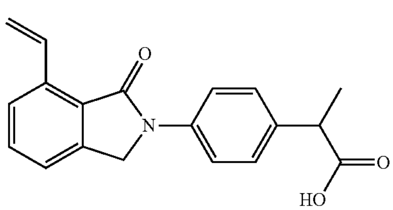 | ALB-113393 | 0.209 | 1.205 |
| 376 | 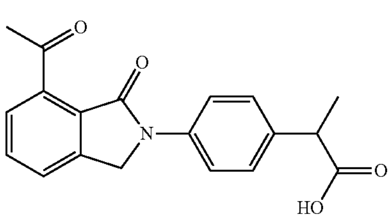 | ALB-113496 | | 1.183 |

TABLE 1-continued
| No. | STRUCTURE | Identifier | Avg EC50 (uM) | Avg MaxFold Increase |
|---|---|---|---|---|
| | | | SMN Splice Reporter Assay (Example 10) | |
| 377 | 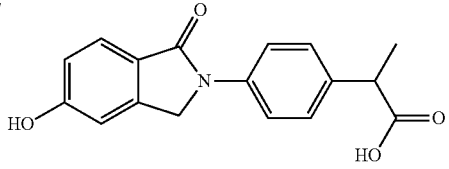 | ALB-113560 | | 1.052 |
| 378 | 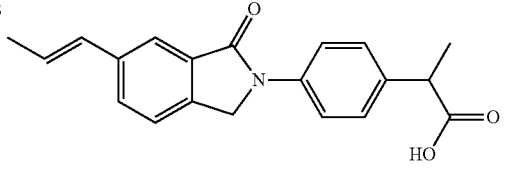 | ALB-114086 | 0.088 | 1.985 |
| 379 | 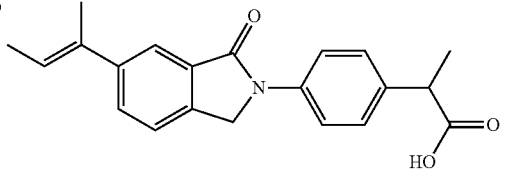 | ALB-114087 | 0.226 | 1.878 |
| 380 | 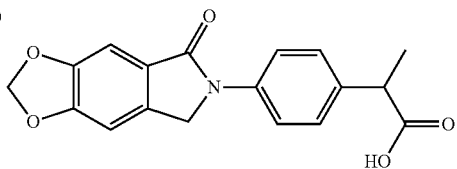 | ALB-114782 | 0.081 | 1.653 |
| 381 | 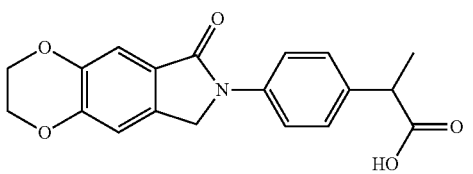 | ALB-114844 | 0.008 | 1.358 |
| 382 | 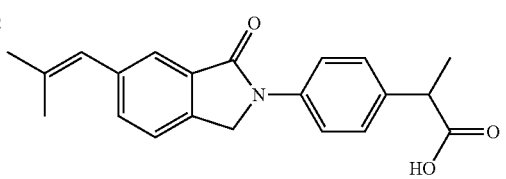 | ALB-115425 | 0.018 | 1.947 |
| 383 | 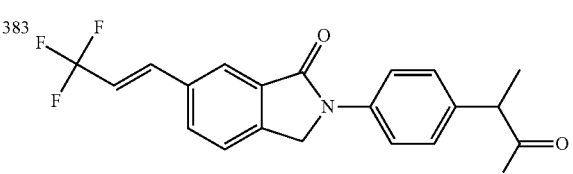 | ALB-115501 | 2.32 | 1.387 |
| 384 | 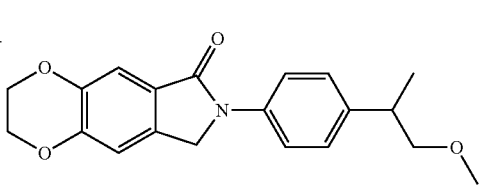 | ALB-116361 | 3.561 | 1.895 |

TABLE 1-continued
| No. | STRUCTURE | Identifier | SMN Splice Reporter Assay (Example 10) | |
| --- | --- | --- | --- | --- |
| | | | Avg EC50 (uM) | Avg MaxFold Increase |
| 385 | 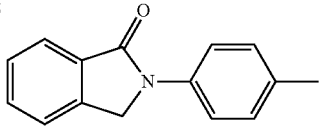 | ALB-114898 | 0.302 | 1.361 |
| 386 | 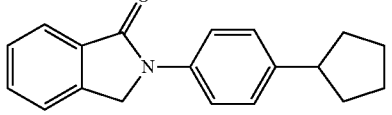 | ALB-115068 | 0.053 | 1.412 |
| 387 | 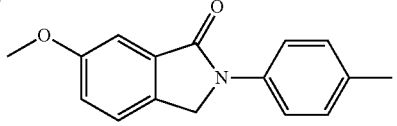 | ALB-115084 | 0.06 | 1.386 |
| 388 | 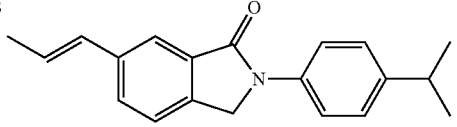 | ALB-115319 | | 1.24 |
| 389 | 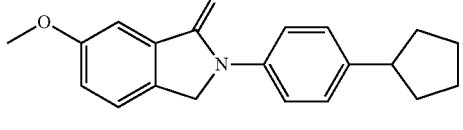 | ALB-115422 | 0.399 | 1.272 |
| 390 | 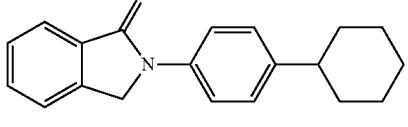 | ALB-115423 | 0.029 | 1.205 |
| 391 | 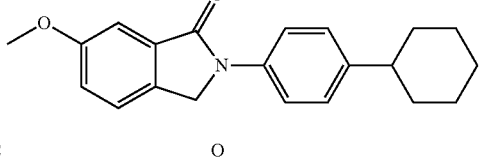 | ALB-115496 | 0.556 | 1.386 |
| 392 | 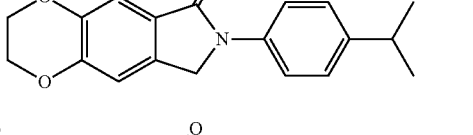 | ALB-115498 | 0.203 | 1.834 |
| 393 | 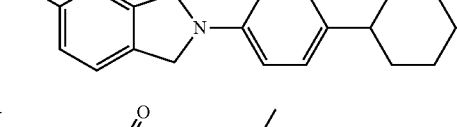 | ALB-115590 | | 1.11 |
| 394 | 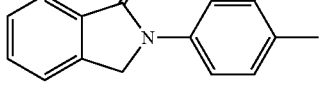 | ALB-115711 | 0.274 | 1.327 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 395 | 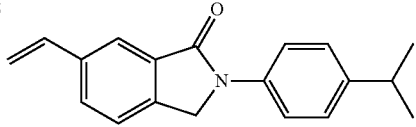 | ALB-115714 | 0.053 | 1.37 |
| 396 | 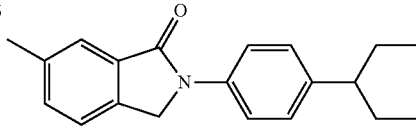 | ALB-115717 | | 1.063 |
| 397 | 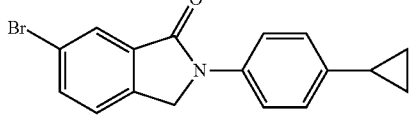 | ALB-115718 | 0.022 | 1.322 |
| 398 | 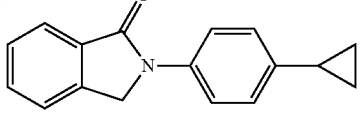 | ALB-115802 | 0.061 | 1.28 |
| 399 | 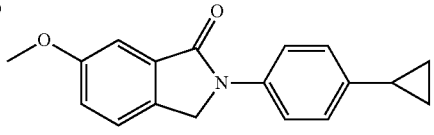 | ALB-115803 | 0.015 | 1.26 |
| 400 | 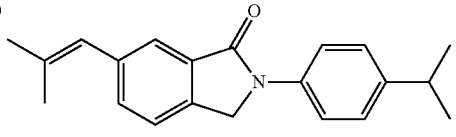 | ALB-115807 | 0.155 | 1.305 |
| 401 | 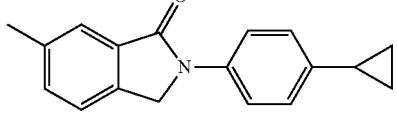 | ALB-115949 | 0.006 | 1.366 |
| 402 | 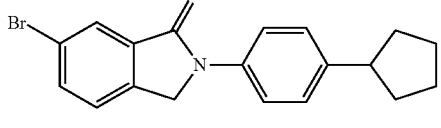 | ALB-116072 | 0.068 | 1.36 |
| 403 | 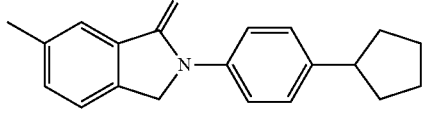 | ALB-116073 | | 1.076 |
| 404 | 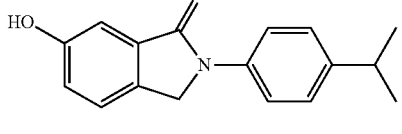 | ALB-116078 | 0.267 | 1.644 |

TABLE 1-continued
| No. | STRUCTURE | Identifier | SMN Splice Reporter Assay (Example 10) Avg EC50 (uM) | Avg MaxFold Increase |
|---|---|---|---|---|
| 405 | 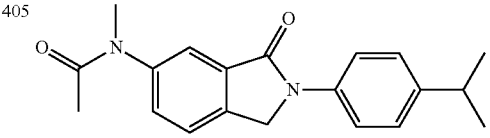 | ALB-117047 | 0.269 | 1.387 |
| 406 | 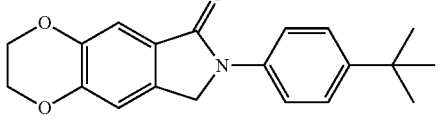 | ALB-117452 | 0.289 | 1.397 |
| 407 | 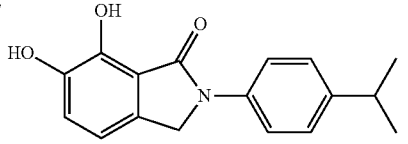 | ALB-117903 | | 1.069 |
| 408 | 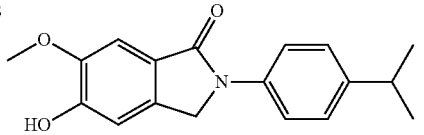 | ALB-118035 | | 1.131 |
| 409 | 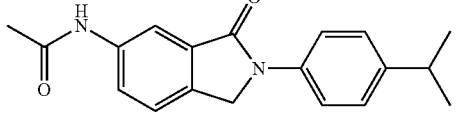 | ALB-118157 | 0.203 | 1.511 |
| 410 | 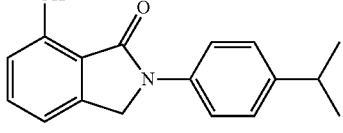 | ALB-118158 | 0.733 | 1.544 |
| 411 | 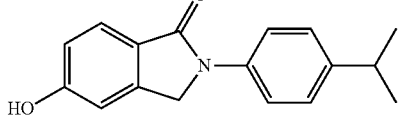 | ALB-118277 | 0.027 | 1.153 |
| 412 | 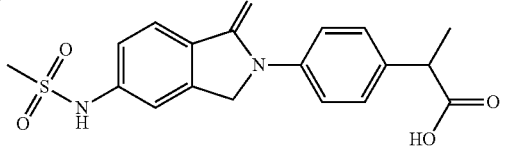 | ALB-113647 | | 1.106 |
| 413 | 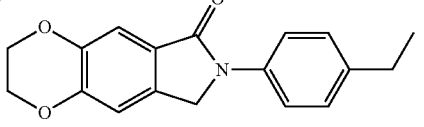 | ALB-116240 | 0.033 | 1.623 |

TABLE 1-continued
| No. | STRUCTURE | Identifier | SMN Splice Reporter Assay (Example 10) | |
|---|---|---|---|---|
| | | | Avg EC50 (uM) | Avg MaxFold Increase |
| 414 | 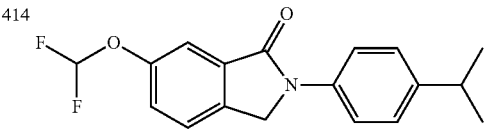 | ALB-116244 | 0.599 | 1.568 |
| 415 | 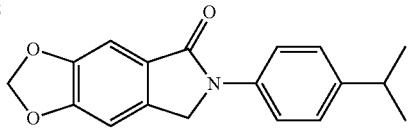 | ALB-116362 | 0.123 | 1.521 |
| 416 | 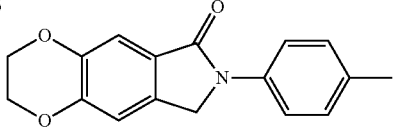 | ALB-116363 | 0.024 | 1.536 |
| 417 | 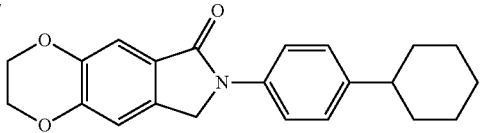 | ALB-116417 | | 1.112 |
| 418 | 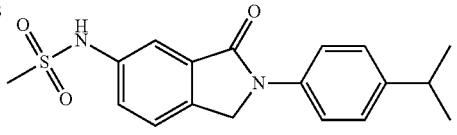 | ALB-116486 | 0.757 | 1.492 |
| 419 | 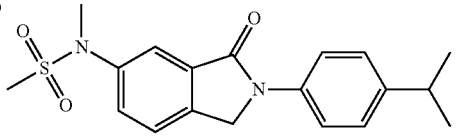 | ALB-116638 | 0.166 | 1.515 |
| 420 | 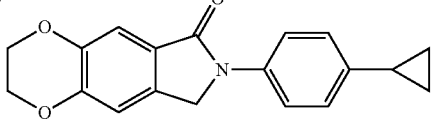 | ALB-117043 | 0.068 | 1.566 |
| 421 | 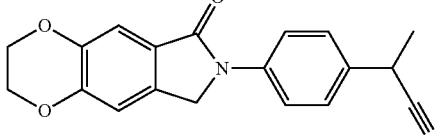 | ALB-117571 | 0.401 | 1.297 |
| 422 | 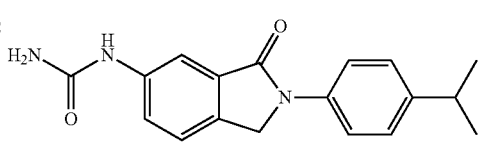 | ALB-117573 | 0.345 | 1.671 |

TABLE 1-continued
| No. | STRUCTURE | Identifier | SMN Splice Reporter Assay (Example 10) Avg EC50 (uM) | Avg MaxFold Increase |
|---|---|---|---|---|
| 423 | 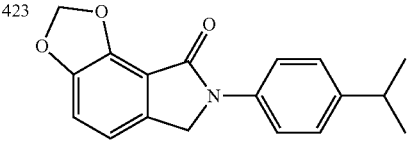 | ALB-117751 | 0.027 | 1.34 |
| 424 | 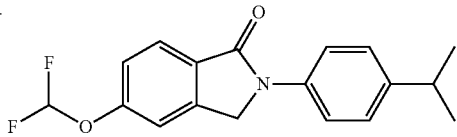 | ALB-118159 | 2.086 | 1.317 |
| 425 | 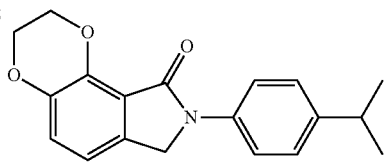 | ALB-118160 | 0.046 | 1.428 |
| 426 | 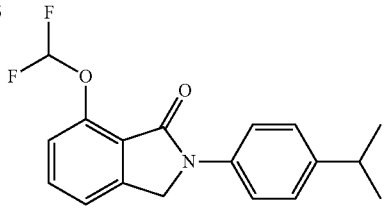 | ALB-118279 | 0.22 | 1.553 |
| 427 | 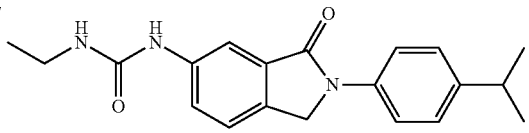 | ALB-118414 | 3.526 | 1.355 |
| 428 | 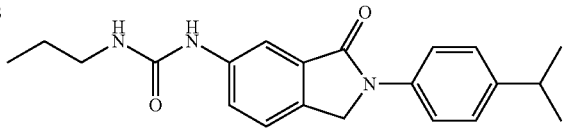 | ALB-118415 | 13.188 | 1.4 |
| 429 | 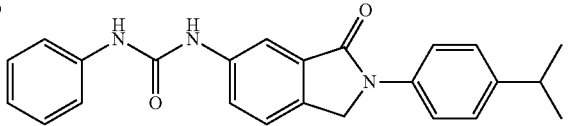 | ALB-118416 |  | 1.17 |
| 430 | 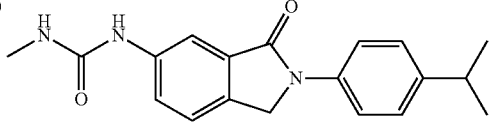 | ALB-118558 | 0.865 | 1.584 |
| 431 | 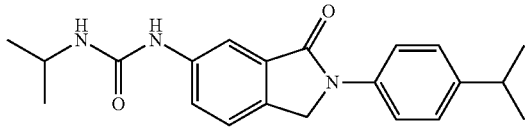 | ALB-118559 |  | 1.098 |

TABLE 1-continued
| No. | STRUCTURE | Identifier | Avg EC50 (uM) | Avg MaxFold Increase |
|---|---|---|---|---|
| 432 | 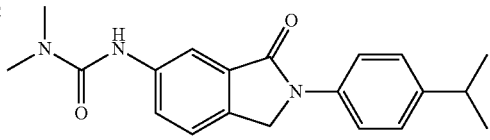 | ALB-118731 | 0.854 | 1.197 |
| 433 | 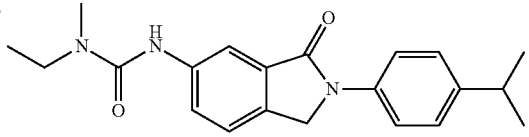 | ALB-118732 |  | 1.153 |
| 434 | 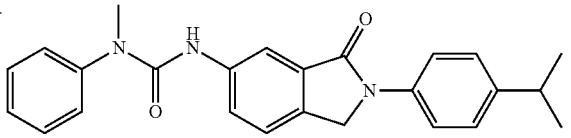 | ALB-118733 |  | 1.118 |
| 435 | 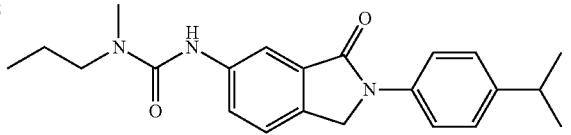 | ALB-118898 |  | 1.063 |
| 436 | 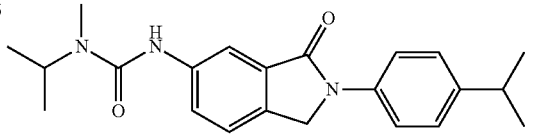 | ALB-118899 |  | 1.076 |
| 437 | 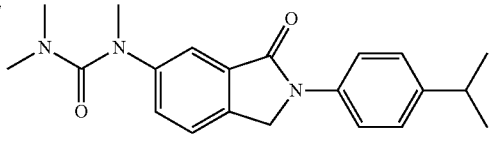 | ALB-118901 | 0.493 | 1.311 |
| 438 | 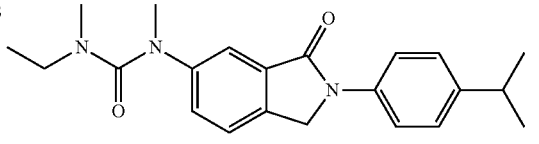 | ALB-119049 |  | 1.085 |
| 439 | 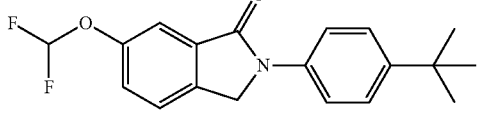 | ALB-119043 | 0.992 | 1.386 |
| 440 | 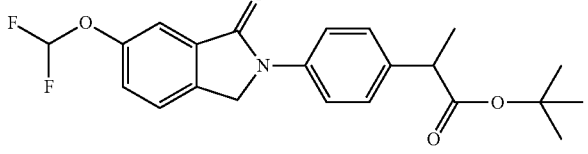 | ALB-119336 | 0.718 | 1.213 |

TABLE 1-continued

| No. | STRUCTURE | Identifier | SMN Splice Reporter Assay (Example 10) | |
|---|---|---|---|---|
| | | | Avg EC50 (uM) | Avg MaxFold Increase |
| 441 | ![structure] | ALB-119335 | 0.051 | 1.537 |
| 442 | ![structure] | ALB-119515 | 0.146 | 1.456 |
| 443 | ![structure] | ALB-112072 | | 1.073 |

The following examples further illustrate the invention but, of course, should not be construed as in any way limiting its scope. Some compounds are referenced in the Examples by identifier codes starting with "ALB." These codes are correlated with the structure of the molecule in Table 1.

EXAMPLE 1

This example illustrates the preparation of 2-(4-(6-chloro-1-oxoisoindolin-2-yl)phenyl) propanoic acid.

Step A: Synthesis of tert-butyl 2-(4-nitrophenyl)propanoate as an Intermediate

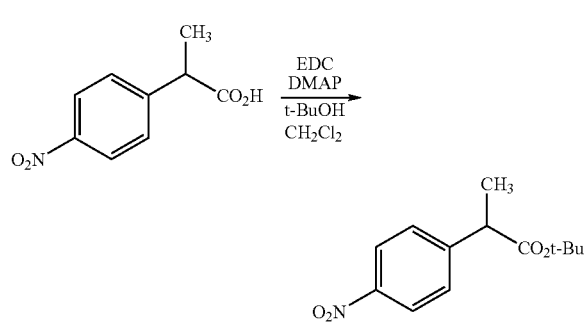

A mixture of 2-(4-nitrophenyl)propanoic acid (15.0 g, 76.9 mmol), dimethylaminopyridine (4.70 g, 38.4 mmol) and tert-butanol (8.10 mL, 84.6 mmol) in methylene chloride (300 mL) was stirred at 0° C. for 2 h. After this time, 1-ethyl-3-(3-dimethylaminopropyl) carbodiimide hydrochloride (17.0 g, 84.6 mmol) was added and the reaction stirred for a further 2 h. The ice bath was then removed and the reaction left to stir at room temperature overnight. After this time, the solvents were concentrated under reduced pressure and the solids redissolved in ethyl acetate (200 mL). The organic layer was then washed with saturated sodium bicarbonate (200 mL), 1 M citric acid (200 mL) and brine (200 mL), dried over magnesium sulfate, filtered, and concentrated under reduced pressure. Purification by flash chromatography (silica, 1:20 ethyl acetate/hexanes) afforded tert-butyl 2-(4-nitrophenyl)propanoate (14.4 g, 75%) as a yellow oil: $^1$H NMR (500 MHz, CDCl$_3$) δ 8.19 (d, J=9.2 Hz, 2H), 7.46 (d, J=9.2 Hz, 2H), 3.73 (q, J=7.1 Hz, 1i), 1.49 (d, J=7.1 Hz, 3H), 1.40 (s, 9H).

Step B: Synthesis of tert-butyl 2-(4-aminophenyl)propanoate as an Intermediate

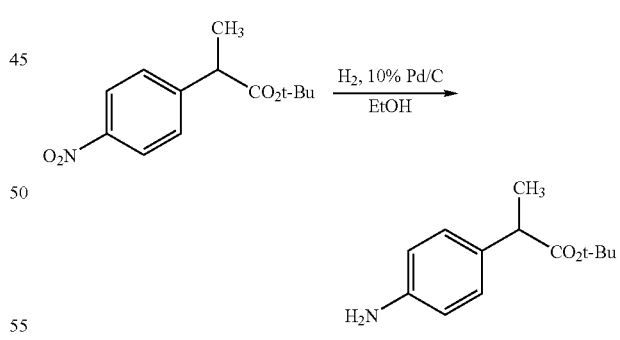

A mixture of tert-butyl 2-(4-nitrophenyl)propanoate (14.4 g, 57.3 mmol) and 10% palladium on carbon (1.44 g, 10% by weight) in ethanol (150 mL) was shaken under an atmosphere of hydrogen at 40 psi for 2 h. After this time, the reaction was filtered through diatomaceous earth, and concentrated under reduced pressure to afford tert-butyl 2-(4-aminophenyl)propanoate (12.5 g, 99%) as an orange oil: 1H NNR (300 MHz, CDCl3) δ 7.07 (d, J=9.1 Hz, 2H), 6.63 (d, J=9.1 Hz, 2H), 3.60 (s, 2H), 3.49 (q, J=7.1 Hz, 1H), 1.40 (d, 3H), 1.38 (s, 9H); ESI MS m/z 222 [M+H]+.

Step C: Synthesis of ethyl 5-chloro-2-methylbenzoate as an Intermediate

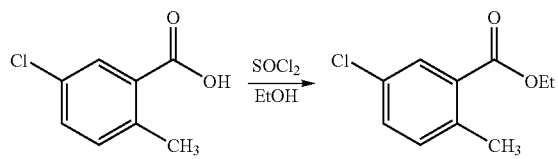

A mixture of 5-chloro-2-methylbenzoic acid (3.00 g, 17.5 mmol) in ethanol (30 mL) was cooled to 0° C. with an ice bath and thionyl chloride (12.5 mL, 105.5 mmol) was added dropwise, over 30 minutes. After this time, the mixture was warmed to room temperature for 1 h, then transferred to an oil bath, and heated to 70° C. overnight. The mixture was then cooled to room temperature and concentrated under reduced pressure. The solids obtained were then redissolved in diethyl ether (50 mL) and washed with 1 N sodium hydroxide (50 mL), brine (50 mL), dried over magnesium sulfate, and concentrated under reduced pressure to afford ethyl 5-chloro-2-methylbenzoate as a clear oil: 1H NMR (500 MHz, $CDC_{13}$) δ 7.88 (d, J=2.5 Hz, 1H), 7.34 (dd, J=8.5, 2.5 Hz, 1H), 7.17 (d, J=8.5 Hz, 1H), 4.36 (q, J=7.5 Hz, 2H), 2.56 (s, 3H), 1.39 (t, J=7.5 Hz, 3H); ESI MS m/z 199 [M+H]+.

Step D: Synthesis of ethyl 2-(bromomethyl)-5-chlorobenzoate as an Intermediate

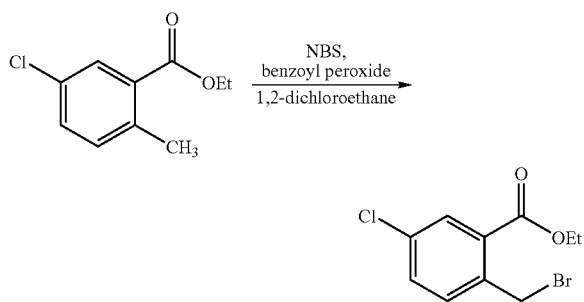

A mixture of ethyl 5-chloro-2-methylbenzoate (3.20 g, 16.1 mmol), N-bromosuccinimide (3.15 g, 17.7 mmol) and benzoyl peroxide (0.39 g, 1.61 mmol) in 1,2-dichloroethane (90 mL) was heated to 75° C. in an oil bath for 4 h. After this time, the mixture was cooled to room temperature and the organic layer was washed with water (45 mL) and brine (45 mL). The organic layer was then dried over magnesium sulfate and concentrated under reduced pressure. Purification by flash chromatography (silica, 1:20 ethyl acetate/hexanes) afforded ethyl 2-(bromomethyl)-5-chlorobenzoate (3.09 g, 68%) as a clear oil: 1H NMR (500 MHz, $CDC_{13}$) 7.94 (d, J=2.5 Hz, 1H), 7.46 (dd, J=8.5, 2.5 Hz, 1H), 7.40 (d, J=8.0 Hz, 1H), 4.91 (s, 2H), 4.42 (q, J=7.0 Hz, 2H), 1.43 (t, J=7.0 Hz, 3H); ESI MS m/z 279 [(M+2)+H]+.

Step E: Synthesis of tert-butyl 2-(4-(6-chloro-1-oxoisoindolin-2-yl)phenyl)propanoate

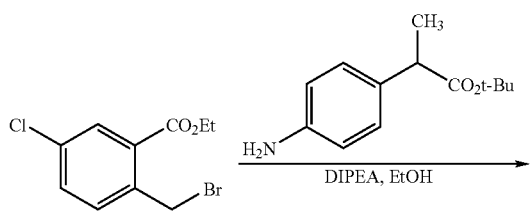

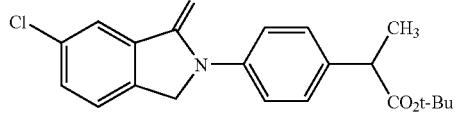

A mixture of tert-butyl 2-(4-aminophenyl)propanoate (0.24 g, 1.08 mmol), ethyl 2-(bromomethyl)-5-chlorobenzoate (0.25 g, 0.901 mmol) and N,N-diisopropylethylamine (0.14 g, 1.08 mmol) in ethanol (5 mL) was heated in a sealed tube at 100° C. overnight. After this time, the mixture was cooled with an ice bath and the solids collected by filtration to afford tert-butyl 2-(4-(6-chloro-1-oxoisoindolin-2-yl)phenyl)propanoate (0.18 g, 55%) as a white solid: mp 169-171° C.; 1H NMR (500 MHz, CDCl3) δ 7.89 (d, J=2.5 Hz, 1H), 7.79 (d, J=8.5 Hz, 2H), 7.56 (dd, J=8.0, 2.0 Hz, 1H), 7.45 (d, J=8.0 Hz, 1H), 7.36 (d, J=8.5 Hz, 2H), 4.84 (s, 2H), 3.63 (m, 1H), 1.45 (d, J=7.5 Hz, 3H), 1.41 (s, 9H); ESI MS m/z 404 [M+H+CH3OH]+.

Step F: Synthesis of 2-(4-(6-chloro-1-oxoisoindolin-2-yl)phenyl)propanoic acid

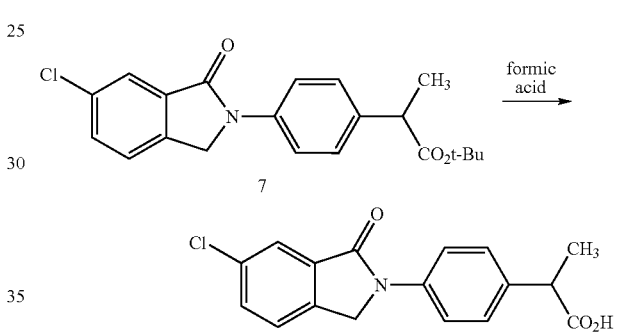

A mixture of tert-butyl 2-(4-(6-chloro-1-oxoisoindolin-2-yl)phenyl)propanoate (0.157 g, 0.422 mmol) and formic acid (15.7 mL) was stirred overnight at room temperature. The mixture was then concentrated under reduced pressure, suspended in hexanes (5 mL), sonicated, and the solids collected by filtration to afford 2-(4-(6-chloro-1-oxoisoindolin-2-yl)phenyl)propanoic acid (0.118 g, 89%) as a white solid: mp 235-248° C. (dec); $^1$H NMR (500 MHz, DMSO-$d_6$) δ 12.35 (br s, 1H), 7.83 (d, J=8.5 Hz, 2H), 8.44 (s, 1H), 7.78 (m, 2H), 7.51 (m, 2H), 5.02 (s, 2H), 3.69 (q, J=7.0 Hz, 1H), 1.38 (d, J=7.0 Hz, 3H); ESI MS m/z 348 [M+H+CH$_3$OH]$^+$.

EXAMPLE 2

This example illustrates the preparation of 2-(4-(1-oxo-6-propylisoindolin-2-yl)phenyl)propanoic acid Step A: Synthesis of ethyl 2-methyl-5-nitrobenzoate as an Intermediate

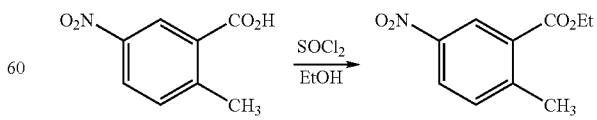

A mixture of 2-methyl-5-nitrobenzoic acid (10.0 g, 55.2 mmol) in ethanol (200 ml) was cooled to 0° C. with an ice bath and thionyl chloride (16.0 mL, 220 mmol) was added dropwise over 10 min. After this time, the mixture was warmed to room temperature for 1 h, then transferred to an oil bath and heated to reflux overnight. The mixture was then cooled to room temperature and concentrated under reduced pressure. Purification by flash chromatography (silica, 9:1 hexanes/ethyl acetate) afforded ethyl 2-methyl-5-nitrobenzoate (12.4 g, quant.) as a pale yellow oil: $^1$H NMR (300 MHz, CDCl$_3$) δ 8.76 (d, J=2.5 Hz, 1H), 8.24 (dd, J=8.5, 2.5 Hz, 1H), 7.43 (d, J=8.4 Hz, 1H), 4.42 (q, J=7.2 Hz, 2H), 2.72 (s, 3H), 1.44 (t, J=7.1 Hz, 3H).

Step B: Synthesis of ethyl 5-amino-2-methylbenzoate as an Intermediate

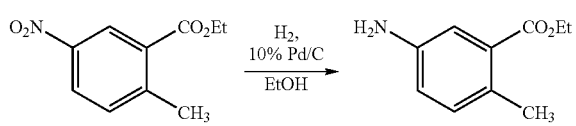

A mixture of ethyl 2-methyl-5-nitrobenzoate (11.5 g, 54 mmol) and 10% Pd/C (1.2 g) in ethanol (200 mL) was shaken under an atmosphere of hydrogen at 40 psi for 18 h. After this time, the mixture was filtered through diatomaceous earth and concentrated under reduced pressure to provide ethyl 5-amino-2-methylbenzoate (9.77 g, 98%) as an off-white solid: $^1$H NMR (300 MHz, CDCl$_3$) δ 7.25 (d, J=2.6 Hz, 1H), 7.02 (d, J=8.1 Hz, 1H), 6.74 (d, J=8.1 Hz, 1H), 4.33 (q, J=7.2 Hz, 2H), 2.46 (s, 3H), 1.38 (t, J=7.1 Hz, 3H).

Step C: Synthesis of ethyl 5-bromo-2-methylbenzoate as an Intermediate

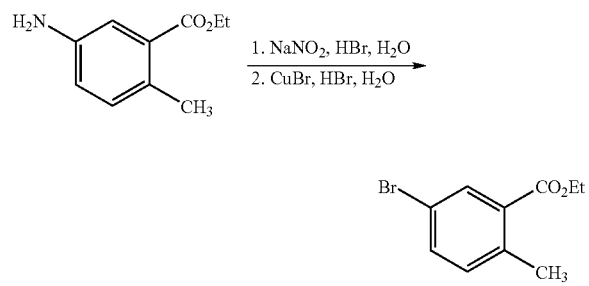

A mixture of ethyl 5-amino-2-methylbenzoate (1.50 g, 8.3 mmol) in 48% HBr (12 mL) and water (24 mL) was cooled with an ice-bath for 15 min. Sodium nitrite (0.59 g, 8.6 mmol) was then added dropwise as a solution in water (2 mL), and the resulting mixture stirred for 5 min. After this time, the mixture was added to an ice-cold mixture of copper (I) bromide (1.40 g, 9.90 mmol) in 48% HBr (5 mL) and water (12 mL). The resulting mixture was heated to 70° C. for 1 h. After this time, the reaction mixture was cooled to room temperature and diluted with diethyl ether (150 mL). The organic layer was washed with 1 N hydrochloric acid (50 mL), water (50 mL), and brine (50 mL) then dried over sodium sulfate, filtered and concentrated under reduced pressure. Purification by flash chromatography (silica, gradient 1-10%, hexanes/ethyl acetate) afforded 1.4 g (69%) of ethyl 5-bromo-2-methylbenzoate as a colorless oil: $^1$H NMR (500 MHz, CDCl$_3$) δ 8.03 (d, J=2.2 Hz, 1H), 7.50 (dd, J=8.2, 2.2 Hz, 1H), 7.12 (dd, J=8.2 Hz, 1H), 4.36 (q, J=7.1 Hz, 2H), 2.54 (s, 3H), 1.40 (t, J=7.2 Hz, 3H); ESI MS m/z 404 [M+H]$^+$.

Step D: Synthesis of ethyl 5-bromo-2-(bromomethyl)benzoate as an Intermediate

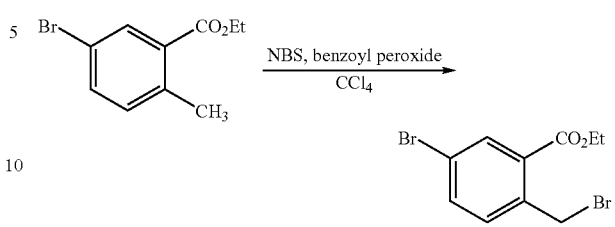

A mixture of ethyl 5-bromo-2-methylbenzoate (7.52 g, 30.9 mmol), N-bromosuccinimide (6.05 g, 34.0 mmol) and benzoyl peroxide (0.75 g, 3.10 mmol) in carbon tetrachloride (150 ml) was heated to 70° C. in an oil bath for 18 h. After this time, the mixture was cooled to room temperature and the solids removed by filtration. The filtrate was then concentrated under reduced pressure and purified by flash chromatography (silica, gradient 1-10%, ethyl acetate/hexanes) afforded ethyl 5-bromo-2-(bromomethyl)benzoate (7.57 g, 76%) as a clear oil: $^1$H NMR (300 MHz, CDCl$_3$) 8.09 (d, J=2.2 Hz, 1H), 7.61 (dd, J=8.3, 2.2 Hz, 1H), 7.33 (d, J=8.2 Hz, 1H), 4.90 (s, 2H), 4.42 (q, J=7.2 Hz, 2H), 1.43 (t, J=7.1 Hz, 3H).

Step E: Synthesis of tert-butyl 2-(4-(6-bromo-1-oxoisoindolin-2-yl)phenyl)propanoate

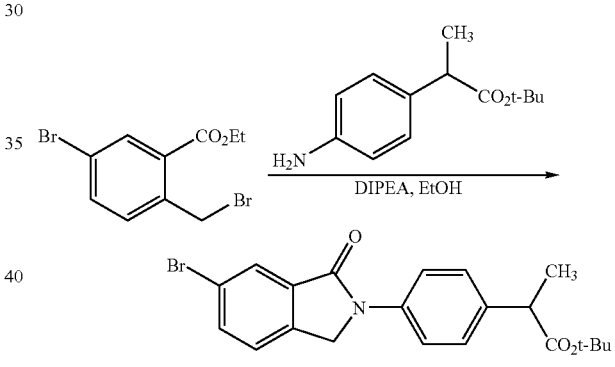

A mixture of ethyl 5-bromo-2-(bromomethyl)benzoate (4.00 g, 12.4 mmol), tert-butyl 2-(4-aminophenyl)propanoate (3.4 g, 15.4 mmol) and N,N-diisopropylethylamine (1.98 g, 15.4 mmol) in ethanol (120 mL) was heated in a sealed tube at 100° C. overnight. After this time, the mixture was cooled with an ice bath and the solids collected by filtration to afford tert-butyl 2-(4-(6-bromo-1-oxoisoindolin-2-yl)phenyl)propanoate (2.00 g, 39%) as a white solid: mp 164-165° C.: $^1$H NMR (300 MHz, CDCl$_3$) δ 8.06 (d, J=1.7 Hz, 1H), 7.81-7.77 (m, 2H), 7.71 (dd, J=8.0, 1.8 Hz, 1H), 7.40 (d, J=8.4 Hz, 1H), 7.38-7.34 (m, 2H), 4.81 (s, 2H), 3.63 (q, J=7.1 Hz, 1H), 1.46 (d, J=7.2 Hz, 3H), 1.41 (s, 9H); ESI MS m/z 448 [M+H+CH$_3$OH]$^+$.

Step F: Synthesis of tert-butyl 2-(4-(1-oxo-6-(prop-1-enyl)isoindolin-2-yl)phenyl)propanoate

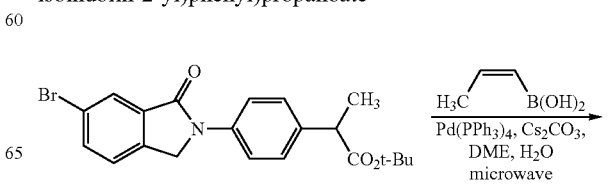

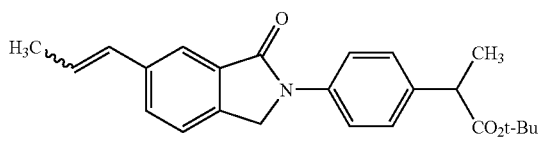

A mixture of tert-butyl 2-(4-(6-bromo-1-oxoisoindolin-2-yl)phenyl)propanoate (0.200 g, 0.48 mmol), cis-1-propene-1-boronic acid (0.413 g, 4.8 mmol), tetrakis(triphenylphosphine)palladium(0) (0.554 g, 0.48 mmol), and cesium carbonate (0.470 g, 1.44 mmol) in 5:2 DME/water (7 mL) was heated in a microwave reactor for 20 min at 120° C. The mixture was cooled to room temperature, then diluted with ethyl acetate (8 mL). The reaction mixture was concentrated and purified by flash chromatography (silica, gradient 1-20%, ethyl acetate/hexanes) afforded tert-butyl 2-(4-(1-oxo-6-(prop-1-enyl)isoindolin-2-yl)phenyl)propanoate (0.144 g, 77%) as a yellow solid: mp 125-130° C.; $^1$H NMR (500 MHz, CDCl$_3$) δ 7.96-7.80 (m, 2H), 7.75-7.65 (m, 1H), 7.54-7.34 (m, 4H), 6.53-6.33 (m, 1H), 5.93-5.87 (m, 1H), 4.84-4.80 (m, 2H), 3.66-3.60 (m, 1H), 1.94-1.91 (m, 3H), 1.47-1.45 (m, 3H), 1.41 (s, 9H) [6:4 mixture of olefin isomers determined by NMR]; ESI MS m/z 378 [M+H]$^+$.

Step G: Synthesis of tert-butyl 2-(4-(1-oxo-6-propylisoindolin-2-yl)phenyl)propanoate

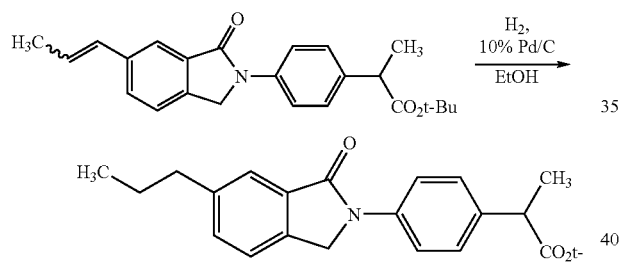

A mixture of tert-butyl 2-(4-(1-oxo-6-prop-1-enyl)isoindolin-2-yl)phenyl)propanoate (0.140 g, 0.37 mmol) and 10% Pd/C (140 mg) in ethanol (5 mL) was shaken under an atmosphere of hydrogen at 35 psi for 2 h. After this time, the mixture was filtered through diatomaceous earth and concentrated under reduced pressure. Purification by flash column chromatography (silica, gradient 1-20%, ethyl acetate/hexanes) provided tert-butyl 2-(4-(1-oxo-6-propylisoindolin-2-yl)phenyl)propanoate (0.099 g, 71%) as a white solid: mp 110-115° C.; $^1$H NMR (300 MHz, CDCl$_3$) δ 7.83 (d, J=8.6 Hz, 2H), 7.74 (s, 1H), 7.41-7.37 (m, 4H), 4.81 (s, 2H), 3.77 (q, J=7.1 Hz, 1H), 2.70 (t, J=7.4 Hz, 2H), 1.73-1.65 (m, 2H), 1.54 (d, J=7.2 Hz, 3H), 0.95 (t, J=7.3 Hz, 3H); ESI MS m/z 380 [M+H]$^+$.

Step H: Synthesis of 2-(4-(1-oxo-6-propylisoindolin-2-yl)phenyl)propanoic acid

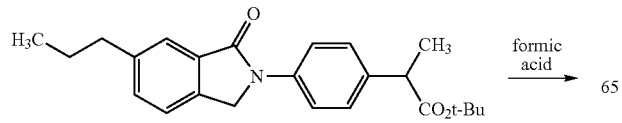

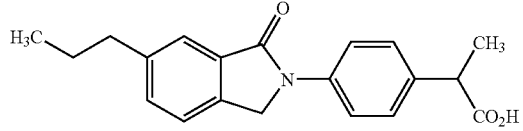

A mixture of tert-butyl 2-(4-(1-oxo-6-propylisoindolin-2-yl)phenyl)propanoate (0.084 g, 0.22 mmol) and formic acid (15 mL) was stirred overnight at room temperature. The mixture was then concentrated under reduced pressure, suspended in hexanes (5 mL), sonicated, and the solid collected by filtration to afford 2-(4-(1-oxo-6-propylisoindolin-2-yl)phenyl)propanoic acid (0.041 g, 57%) as a white solid: mp 175-177° C.; $^1$H NMR (300 MHz, CDCl$_3$) δ 7.83 (d, J=8.6 Hz, 2H), 7.74 (s, 1H), 7.41-7.37 (m, 4H), 4.81 (s, 2H), 3.77 (q, J=7.1 Hz, 1H), 2.70 (t, J=7.4 Hz, 2H), 1.73-1.65 (m, 2H), 1.54 (d, J=7.2 Hz, 3H), 0.95 (t, J=7.3 Hz, 3H); ESI MS m/z 324 [M+H]$^+$.

EXAMPLE 3

This example illustrates the preparation of tert-butyl 2-(3-bromo-4-(1-oxoisoindolin-2-yl)phenyl)propanoate Step A: Synthesis of tert-butyl 2-(4-amino-3-bromophenyl)propanoate as an Intermediate

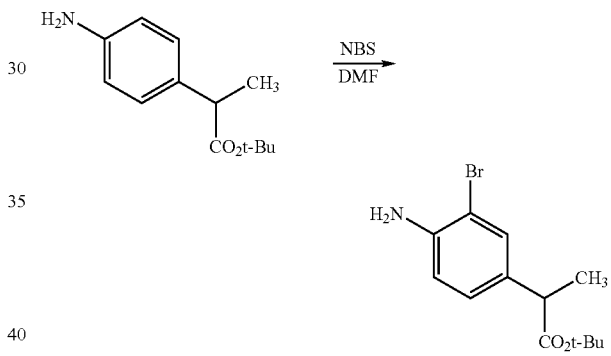

To a solution of tert-butyl 2-(4-aminophenyl)propanoate (5.00 g, 22.6 mmol) in DMF (15 mL) was added a solution of N-bromosuccinimide (4.22 g, 23.7 mmol) in DMF (15 ML) at room temperature which was maintained by water bath. The mixture was stirred overnight, poured into water and extracted with ethyl acetate. The organic layer was separated, washed with water, then brine, dried over sodium sulfate, and filtered. After concentration, the residue was purified by flash chromatography (9:1 hexanes/ethyl acetate) to give tert-butyl 2-(4-amino-3-bromophenyl)propanoate (6.00 g, 85%) as a brown oil: $^1$H NMR (500 MHz, CDCl$_3$) δ 7.34 (d, J=1.6 Hz, 1H), 7.04 (dd, J=8.1, 1.7 Hz, 1H), 6.71 (d, J=8.2 Hz, 1H), 4.01 (br s, 2H), 3.46 (q, J=7.1 Hz, 1H), 1.39 (m, 12H).

Step B: Synthesis of methyl 2-((2-bromo-4-(1-tert-butoxy-1-oxopropan-2-yl)phenylamino)methyl)benzoate as an Intermediate

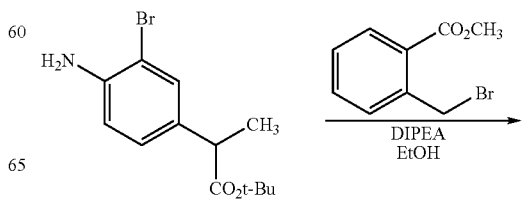

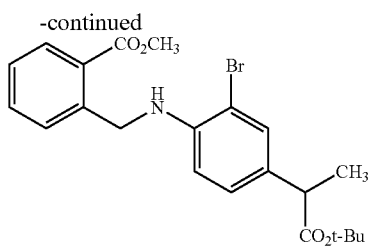

A mixture of tert-butyl 2-(4-amino-3-bromophenyl)propanoate (6.50 g, 21.7 mmol), methyl 2-(bromomethyl)benzoate (4.97 g, 21.7 mmol), diisopropylethylamine (2.80 g, 21.7 mmol), and ethanol (180 mL) was heated at 120° C. in a sealed vial overnight. After cooling to room temperature, the mixture was concentrated and the residue purified by flash chromatography (92:8 hexanes/ethyl acetate) to afford methyl 2-((2-bromo-4-(1-tert-butoxy-1-oxopropan-2-yl)phenylamino)methyl)benzoate (4.72 g, 48%) as thick oil: $^1$H NMR (500 MHz, CDCl$_3$) δ 7.98 (m, 1H), 7.47 (m, 2H), 7.37-7.31 (m, 2H), 7.01 (dd, J=8.4, 2.0 Hz, 1H), 6.50 (d, J=8.4 Hz, 1H), 5.03 (br t, J=6.1 Hz, 1H), 4.75 (d, J=6.2 Hz, 2H), 3.92 (s, 3H), 3.43 (q, J=7.2 Hz, 1H), 1.38 (s, 9H), 1.37 (d, J=7.2 Hz, 3H); ESI MS m/z 450 [(M+2)+H]$^+$.

Step C: Synthesis of 2-((2-bromo-4-(1-tert-butoxy-1-oxopropan-2-yl)phenylamino)methyl)benzoic acid as an Intermediate

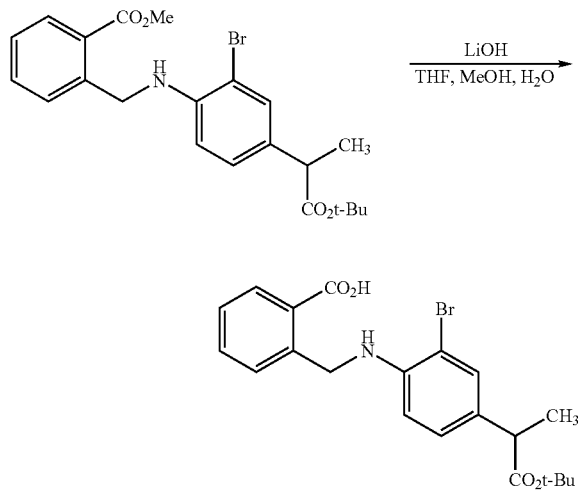

A mixture of methyl 2-((2-bromo-4-(1-tert-butoxy-1-oxopropan-2-yl)phenylamino)methyl)benzoate (4.57 g, 10.2 mmol), lithium hydroxide (0.733 g, 30.6 mmol), tetrahydrofuran (100 mL), methanol (20 mL), and water (30 mL) was stirred overnight. The mixture was poured into water (200 mL) and the whole was acidified with 2 N HCl. The mixture was then extracted with ethyl acetate (150 mL) and the organic layer was washed with brine (100 mL), dried over sodium sulfate, and filtered. Evaporation of the solvents and drying under reduced pressure gave 2-((2-bromo-4-(1-tert-butoxy-1-oxopropan-2-yl)phenylamino)methyl)benzoic acid (4.40 g, 99%) as a thick oil: $^1$H NMR (500 MHz, CDCl$_3$) δ 8.14 (d, J=7.6 Hz, 1H), 7.53 (m, 2H), 7.38 (m, 2H), 7.03 (dd, J=8.4, 2.0 Hz, 1H), 6.53 (d, J=8.0 Hz, 1H), 4.80 (s, 2H), 3.44 (q, J=7.1 Hz, 1H), 1.39 (s, 9H), 1.38 (d, J=7.2 Hz, 3H).

Step D: Synthesis of tert-butyl 2-(3-bromo-4-(1-oxoisoindolin-2-yl)phenyl)propanoate

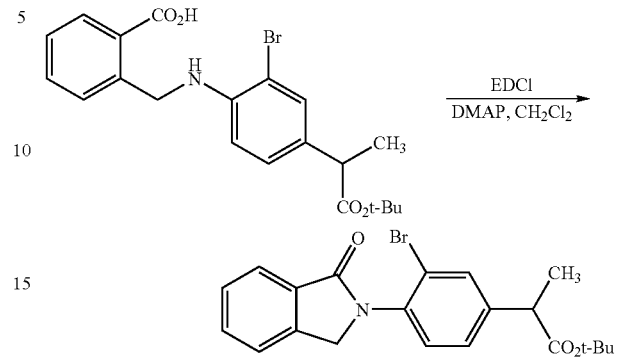

A mixture of 2-((2-bromo-4-(1-tert-butoxy-1-oxopropan-2-yl)phenylamino)methyl)benzoic acid (4.40 g, 10.1 mmol), 1-(3-(dimethylamino)propyl)-3-ethylcarbodiimide hydrochloride (2.13 g, 11.1 mmol) and 4-dimethylaminopyridine (0.617 g, 5.05 mmol) in methylene chloride (80 mL) was stirred at 0° C. and was allowed to warm to room temperature overnight. The mixture was then concentrated and the residue was purified by flash chromatography (silica, 4:1 hexanes/ethyl acetate) to afford tert-butyl 2-(3-bromo-4-(1-oxoisoindolin-2-yl)phenyl)propanoate (3.55 g, 85%) as white foam: $^1$H NMR (500 MHz, CDCl$_3$) δ 7.96 (d, J=7.6 Hz, 1H), 7.64-7.50 (m, 4H), 7.35 (d, J=1.0 Hz, 2H), 4.79 (s, 2H), 3.63 (q, J=7.2 Hz, 1H), 1.47 (d, J=7.2 Hz, 3H), 1.44 (s, 9H); ESI MS m/z 418 [(M+2)+H]$^+$.

Following the procedure of Example 1 (Step F), but substituting the appropriate t-butyl ester, the compounds of Table 2 were prepared.

TABLE 2

| $R_4$ | $R_5$ | $R_6$ | $R_7$ | mp ° C. | m/z |
|---|---|---|---|---|---|
| H | H | H | Cl | 236-238 | 316 [M + H]$^+$ |
| H | H | H | OCH$_3$ | 275 | 310 [M − H]$^-$ |
| H | H | H | NO$_2$ | 234-236 | 327 [M + H]$^+$ |
| H | H | H | Br | 245-249 | 360 [M + H]$^+$ |
| H | H | H | phenyl | 202-207 | 358 [M + H]$^+$ |
| H | H | H | CH$_3$ | 179-182 | 296 [M + H]$^+$ |
| H | H | H | O-i-Pr | 168-172 | 340 [M + H]$^+$ |
| H | H | OCH$_3$ | H | 196-198 | 312 [M + H]$^+$ |
| H | H | phenyl | H | 255-263 | 358 [M + H]$^+$ |
| H | H | CN | H | 225-233 | 307 [M + H]$^+$ |
| H | H | OEt | H | 172-175 | 326 [M + H]$^+$ |
| H | H | OCHF$_2$ | H | 202-204 | 380 [M + H + CH$_3$OH]$^+$ |
| H | OCH$_3$ | OCH$_3$ | H | 227-232 | 340 [M − H]$^-$ |
| H | F | OCH$_3$ | H | 250-252 | 330 [M + H]$^+$ |
| H | Cl | H | H | 238-242 | 316 [M + H]$^+$ |
| H | Br | H | H | 253-256 | 360 [M + H]$^+$ |
| H | NH$_2$ | H | H | 237-240 | 297 [M + H]$^+$ |
| Cl | H | H | H | 171-174 | 316 [M + H]$^+$ |
| OCH$_3$ | H | H | H | 174-178 | 310 [M − H]$^-$ |

EXAMPLE 4

This example illustrates the preparation of 6-methoxy-2-(4-(1-methoxypropan-2-yl)phenyl)isoindolin-1-one Step A: Synthesis of 2-(4-(1-hydroxypropan-2-yl)phenyl)-6-methoxyisoindolin-1-one as an Intermediate

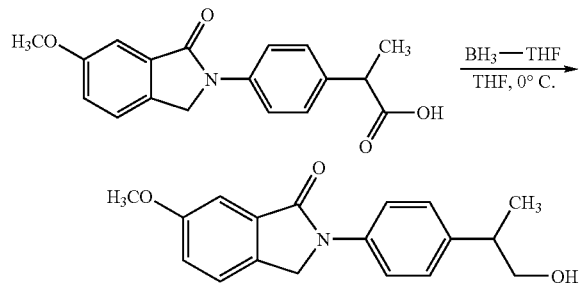

A mixture of 2-(4-(6-methoxy-1-oxoisoindolin-2-yl)phenyl)propanoic acid (0.102 g, 0.33 mmol) and borane-tetrahydrofuran complex (0.83 mL, 1 M in tetrahydrofuran, 0.83 mmol) in tetrahydrofuran (2 mL) at 0° C. was stirred for 3 h. After this time, the reaction mixture was diluted with water (5 mL) and ethyl acetate (5 mL) and the mixture stirred vigorously for 18 h at room temperature. The aqueous layer was separated and extracted with ethyl acetate (25 mL), and the combined organic layers dried over sodium sulfate, filtered, and concentrated under reduced pressure to afford an off-white solid. Purification by flash chromatography (silica, 1:1 ethyl acetate/hexanes) afforded 2-(4-(1-hydroxypropan-2-yl)phenyl)-6-methoxyisoindolin-1-one (0.081 g, 84%) as a white solid: mp 135-138° C.; $^1$H NMR (300 MHz, CDCl$_3$) δ 7.81 (dd, J=8.6, 19 Hz, 2H), 7.41-7.39 (m, 2H), 7.31 (d, J=8.6 Hz, 2H), 7.16 (dd, J=8.4, 2.4 Hz, 1H), 4.79 (s, 2H), 3.89 (s, 3H), 3.72 (d, J=6.8 Hz, 2H), 2.98 (q, J=6.9 Hz, 1H), 1.30 (d, J=7.0 Hz, 3H); ESI MS m/z 298 [M+H]$^+$.

Step B: Synthesis of 6-methoxy-2-(4-(1-methoxypropan-2-yl)phenyl)isoindolin-1-one

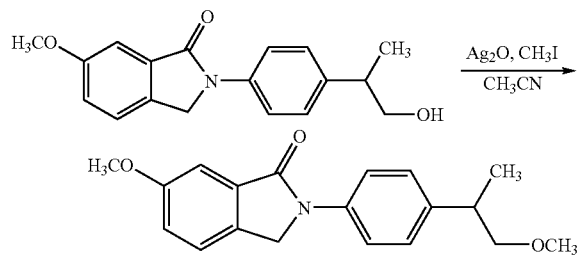

A mixture of 2-(4-(1-hydroxypropan-2-yl)phenyl)-6-methoxyisoindolin-1-one (0.042 g, 0.14 mmol), silver oxide (0.196 g, 0.42 mmol), iodomethane (0.070 mL) and 4 Å molecular sieves (0.050 g) in acetonitrile (2 mL) was stirred for 96 h at room temperature. After this time, the mixture was diluted with water (10 mL) and ethyl acetate (10 mL). The organic layer was separated, dried over sodium sulfate, filtered, and concentrated under reduced pressure to afford an off-white solid Purification by flash chromatography (silica, 1:1 ethyl acetate/hexanes) afforded 6-methoxy-2-(4-(1-methoxypropan-2-yl)phenyl)isoindolin-1-one (0.031 g, 72%) as a white solid: mp 116-118° C.; $^1$H NMR (300 MHz, CDCl$_3$) δ 7.78 (dd, J=8.7, 2.0 Hz, 2H), 7.40-7.38 (m, 2H), 7.29 (dd, J=8.6, 1.9 Hz, 2H), 7.15 (dd, J=8.3, 2.4 Hz, 1H), 4.78 (m, 2H), 3.89 (s, 3H), 3.55-3.41 (m, 2H), 3.34 (s, 3H), 3.04 (q, J=7.0 Hz, 1H), 1.29 (d, J=7.0 Hz, 3H); ESI MS m/z 312 [M+H]$^+$.

EXAMPLE 5

This example illustrates the preparation of 6-chloro-2-(4-isopropylphenyl)isoindolin-1-one.

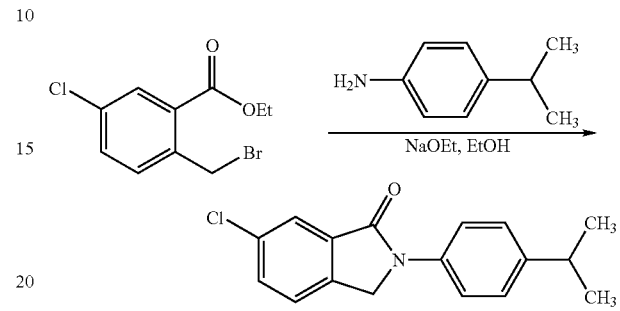

A mixture of ethyl 2-(bromomethyl)-5-chlorobenzoate (0.553 g, 1.99 mmol), 4-isopropylaniline (0.269 g, 1.99 mmol) and sodium ethoxide (0.406 g, 5.97 mmol) in ethanol (40 mL) was heated at reflux overnight. After this time, the mixture was cooled to room temperature and concentrated under vacuum. The mixture was partitioned between 1 N HCl and ethyl acetate. The organic layer was separated, washed with 1 N HCl, then with 1:1 water/brine solution, dried over sodium sulfate and filtered. Concentration under vacuum and recrystallization from ethyl acetate afforded 6-chloro-2-(4-isopropylphenyl)isoindolin-1-one (0.302 g, 53%) as an off-white solid: m.p. 206-209° C.; $^1$H NMR (500 MHz, CDCl$_3$) δ 7.89 (d, J=1.9 Hz, 1H), 7.73 (dt, J=8.6, 2.7 Hz, 2H), 7.55 (dd, J=8.1, 1.9 Hz, 1H), 7.45 (d, J=8.0 Hz, 1H), 7.30 (dt, J=8.5, 2.5 Hz, 2H), 4.83 (s, 2H), 2.96-2.90 (m, 1H), 1.26 (d, 6H); ESI MS m/z 286 [M+H]$^+$.

EXAMPLE 6

This example illustrates the preparation of 2-(4-isopropylphenyl)-6-nitroisoindolin-1-one.

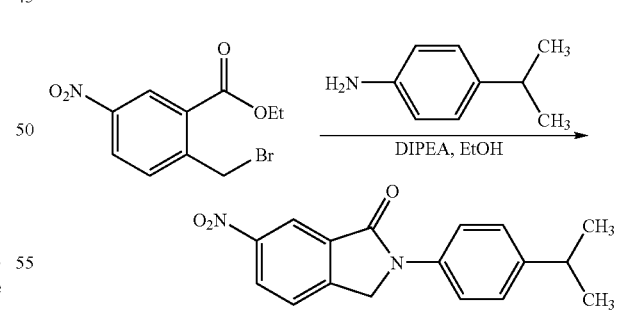

A mixture of ethyl 2-(bromomethyl)-5-nitrobenzoate (1.88 g, 6.52 mmol), 4-isopropylaniline (1.11 mL, 7.83 mmol) and N,N-diisopropylethylamine (1.36 mL, 7.83 mmol) in ethanol (75 mL) was heated in a sealed tube at 110° C. overnight. After this time, the mixture was cooled to room temperature and the solid collected by filtration to afford 2-(4-isopropylphenyl)-6-nitroisoindolin-1-one (1.45 g, 75%) as a yellow solid: mp 225-227° C.; $^1$H NMR (300 MHz, CDCl$_3$) δ 8.77 (d, J=2.0 Hz, 1H) 8.48 (dd, J=8.3, 2.1 Hz, 1H), 7.76-7.69 (m, 3H), 7.32 (d, J=8.6 Hz, 2H), 2.94 (sept, J=6.9 Hz, 1H), 1.28 (d, J=6.9 Hz, 6H); ESI MS m/z 297 [M+H]⁺.

TABLE 3

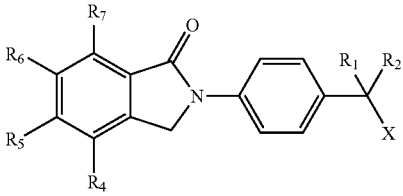

| $R_4$ | $R_5$ | $R_6$ | $R_7$ | $R_1$ | $R_2$ | X | mp °C. | m/z |
|---|---|---|---|---|---|---|---|---|
| H | H | H | OCH₃ | CH₃ | H | CH₃ | 93-96 | 282 [M + H]⁺ |
| H | H | Br | H | CH₃ | H | CH₃ | 205-208 | 331 [M + H]⁺ |
| H | H | OCH₃ | H | CH₃ | H | CH₃ | 152-160 | 282 [M + H]⁺ |
| H | H | OCHF₂ | H | CH₃ | H | CH₃ | 155-157 | 318 [M + H]⁺ |
| H | H | NO₂ | H | CH₃ | H | CH₃ | 225-227 | 297 [M + H]⁺ |
| H | H | CF₃ | H | CH₃ | H | CH₃ | 176-179 | 320 [M + H]⁺ |
| H | Cl | H | H | CH₃ | H | CH₃ | 197-200 | 286 [M + H] |
| H | H | CH₃ | H | CH₃ | CH₃ | CH₃ | 175-182 | 280 [M + H] |
| H | H | H | H | CH₃ | CH₃ | CH₃ | 148-163 | 266 [M + H] |
| H | H | OCH₃ | H | CH₃ | CH₃ | CH₃ | 146-150 | 296 [M + H] |
| H | H | Br | H | CH₃ | CH₃ | CH₃ | 225-228 | 345 [M +H] |
| H | H | Br | H | H | H | Et | 192-196 | 330 [M + H] |
| H | H | OCH₃ | H | CH₃ | H | n-Pr | 103-106 | 310 [M + H] |
| H | H | OCHF₂ | H | CH₃ | CH₃ | CH₃ | 171-172 | 332 [M + H]⁺ |

Following the procedure of Example 6, but substituting the appropriate aniline or benzyl bromide, the compounds of Table 3 were prepared.

EXAMPLE 7

This example illustrates the preparation of ethyl 5-hydroxy-2-methylbenzoate as an Intermediate

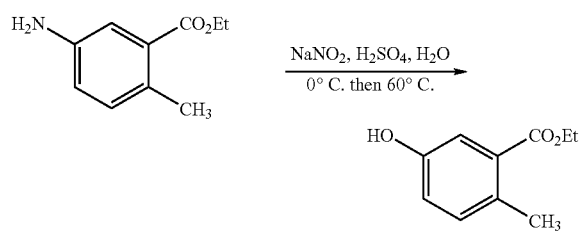

A mixture of ethyl 5-amino-2-methylbenzoate (14.4 g, 80.3 mmol) in aqueous 5% sulfuric acid (300 mL) was cooled with an ice-bath for 15 min. Sodium nitrite (6.09 g, 88.3 mmol) was then added dropwise as a solution in water (50 mL), and the resulting mixture stirred for at 0° C. for 30 min. After this time, the resulting mixture was heated to 60° C. for 18 h. The reaction mixture was then cooled to room temperature and diluted with ethyl acetate (150 mL). The organic layer was separated, dried over sodium sulfate, filtered, and concentrated under reduced pressure. Purification by flash chromatography (silica, gradient 0-40%, hexanes/ethyl acetate) afforded 12.48 g (86%) of ethyl 5-hydroxy-2-methylbenzoate as red-brown solid: ¹H NMR (300 MHz, CDCl₃) δ 7.44 (d, J=2.8 Hz, 1H), 7.10 (d, J=8.3 Hz, 1H), 6.91 (dd, J=8.3, 2.8 Hz, 1H), 5.44 (s, 1H), 4.35 (q, J=7.1 Hz, 2H), 2.50 (s, 3H), 1.38 (t, J=7.1 Hz, 3H); ESI MS m/z 181 [M+H]⁺.

EXAMPLE 8

This example illustrates the preparation of ethyl 5-(difluoromethoxy)-2-methylbenzoate as an Intermediate

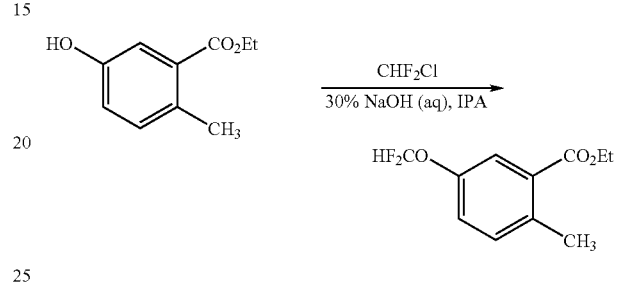

A mixture of ethyl 5-hydroxy-2-methylbenzoate (3.29 g, 18.2 mmol) in aqueous 30% sodium hydroxide (20 mL) and isopropyl alcohol (20 mL) was charged with 20 psi of chlorodifluoromethane in a high pressure flask, and stirred at room temperature for 10 min. After this time, the resulting mixture was heated at 50° C. for 0.5 h. After this time, the reaction mixture was cooled to room temperature and diluted with dichloromethane (50 mL) and water (200 mL). The organic layer was separated, dried over sodium sulfate, filtered, and concentrated under reduced pressure. Purification by flash chromatography (silica, gradient 0-7%, hexanes/ethyl acetate) afforded 2.50 g (59%) of ethyl 5-(difluoromethoxy)-2-methylbenzoate as colorless oil: ¹H NMR (500 MHz, CDCl₃) δ 7.67 (d, J=2.5 Hz, 1H), 7.26-7.22 (m, 1H), 7.18-7.16 (m, 1H), 6.50 (t, J=73.6 Hz, 1H), 4.37 (q, J=7.0 Hz, 2H), 2.57 (s, 3H), 1.40 (t, J=7.0 Hz, 3H); ESI MS m/z 231 [M+H]⁺.

EXAMPLE 9

The following example illustrates the preparation of ethyl 7-methyl-2,3-dihydrobenzo[b][1,4]dioxine-6-carboxylate as an intermediate.

Step A: Synthesis of 6-methyl-2,3-dihydrobenzo[b][1,4]dioxine

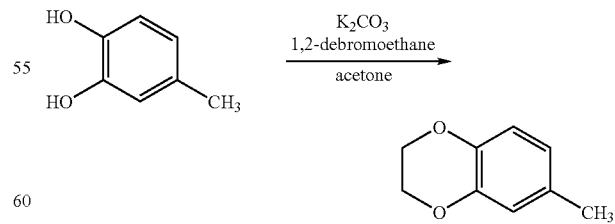

A mixture of 4-methylbenzene-1,2-diol (10.0 g, 80.5 mmol) and potassium carbonate (111.3 g, 805.0 mmol) in acetone (300 mL) was stirred at room temperature for 1 h. After this time, 1,2-dibromoethane (27.7 mL, 322.0 mmol) was added and the reaction stirred at reflux for 5 d. After this time, the solvents were removed under reduced pressure and the solids redissolved in water (500 mL). The aqueous layer was then extracted three times with ethyl acetate (200 mL). The combined organic extracts were then dried over magnesium sulfate, filtered, and concentrated under reduced pressure. Purification by flash chromatography (silica, 1:20 ethyl acetate/hexanes) afforded 6-methyl-2,3-dihydrobenzo[b][1,4]dioxine (6.4 g, 54%) as a green oil: 1H NMR (500 MHz, CDCl3) δ 6.74 (d, J=8.5 Hz, 1H), 6.67 (d, J=2.0 Hz, 1H), 6.63 (dd, J 2.0, 8.0 Hz, 1H), 4.22 (m, 4H), 2.24 (s, 3H).

Step B: Synthesis of 7-methyl-2,3-dihydrobenzo[b][1,4]dioxine-6-carbaldehyde

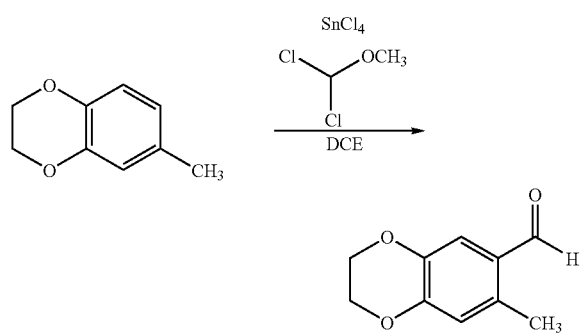

A mixture of 6-methyl-2,3-dihydrobenzo[b][1,4]dioxine (6.4 g, 42.8 mmol) and 1,2-dichloroethane (250 mL) was cooled to 0° C. and then stirred for 1 h. After this time, dichloromethyl methyl ether (11.5 mL, 128.5 mmol) was then added and the reaction stirred for 1 h then, tin (IV) chloride (7.52 mL, 64.3 mmol) was added portion wise to the reaction over 3 h, and the reaction then allowed to warm to room temperature overnight. After this time, the reaction was poured into 3 N hydrochloric acid (150 mL) and the organic layer extracted three times with dichloromethane (100 mL). The combined organic extracts were then dried over magnesium sulfate, filtered, and concentrated under reduced pressure to afford 7-methyl-2,3-dihydrobenzo[b][1,4]dioxine-6-carbaldehyde (4.8 g, 79%) as an off-white solid; 1H NMR (500 MHz, CDCl3) δ 10.07 (s, 1H), 7.33 (s, 1H), 6.72 (s, 1H), 4.28 (m, 4H), 2.55 (s, 3H).

Step C: Synthesis of 7-methyl-2,3-dihydrobenzo[b][1,4]dioxine-6-carboxylic acid

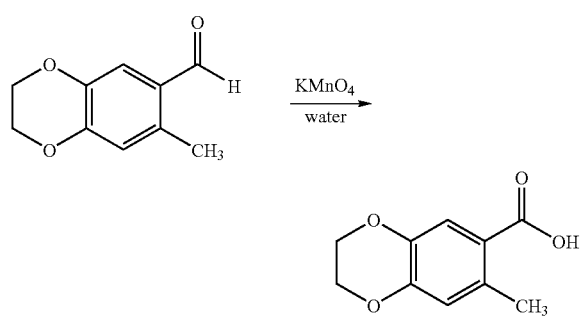

A mixture of 7-methyl-2,3-dihydrobenzo[bb][1,4]dioxine-6-carbaldehyde (2.0 g, 11.2 mmol) in water (100 mL) was heated to 70° C. and stirred for 1 h. Potassium permanganate (2.3 g, 14.6 mmol) in water (50 mL) was then added portion wise over 4 h. After this time, the mixture was cooled to room temperature and 10% potassium hydroxide (50 mL) was then added. The solids were removed by filtration and washed with water (100 mL) and the basic solution then acidified with 2 N hydrochloric acid. The precipitate that formed was collected by filtration, washed with water, and dried in a vacuum oven overnight to afford 7-methyl-2,3-dihydrobenzo[b][1,4]dioxine-6-carboxylic acid (1.7 g, 78%) as a white solid: 1H NMR (500 MHz, DMSO-d6) δ 12.49 (s, 1H), 7.33 (s, 1H), 6.76 (s, 1H), 4.25 (m, 4H), 2.40 (s, 3H).

Step D: Synthesis of ethyl 7-methyl-2,3-dihydrobenzo[b][1,4]dioxine-6-carboxylate

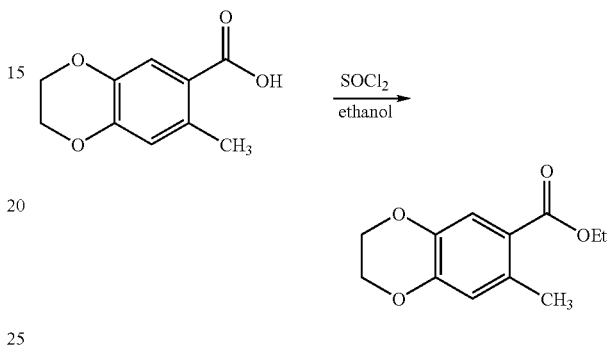

A mixture of 7-methyl-2,3-dihydrobenzo[b][1,4]dioxine-6-carboxylic acid (1.72 g, 8.8 mmol) in ethanol (100 mL) was cooled to 0° C. and stirred for 1 h prior to dropwise addition of thionyl chloride (3.9 mL, 53.2 mmol) over 1 h. After this time, the mixture was warmed to room temperature for 1 h, then transferred to an oil bath, and heated to 70° C. overnight. The mixture was then cooled to room temperature and 2 N hydrochloric acid (50 mL) added slowly followed by diethyl ether (50 mL). The aqueous layer was extracted twice with diethyl ether (50 mL), the combined organic layers washed with brine (100 mL), dried over magnesium sulfate, and concentrated under reduced pressure to afford ethyl 7-methyl-2,3-dihydrobenzo[b][1,4]dioxine-6-carboxylate (1.7 g, 89%) as a white solid: 1H NMR (500 MHz, CDCl3) δ 7.51 (s, 1H), 6.70 (s, 1H), 4.30 (q, J=7.0, 7.5 Hz, 2H), 4.26 (m, 4H), 2.49 (s, 3H), 1.36 (t, J=7.0, 7.5 Hz, 3H).

EXAMPLE 10

This example demonstrates the ability of compounds of the invention to increase SMN expression in cervical carcinoma cell lines.

As previously discussed, SMN1 is the gene deleted in SMA patients; the SMN2 gene remains intact in both SMA and normal patients. Therefore, SMN2 provides a potential means of increasing SMN production in SMA patients and is, thus, a target for developing SMA treatments. SMN2 is identical to SMN1 with the exception of a single base pair change that results in reduced expression of the gene. The reduction is based on the creation of an alternatively spliced RNA that produces an unstable protein carrying a deletion of exon 7. Both full length SMN and exon 7 deleted SMN are produced by the SMN2 gene via alternative RNA splicing, but the major product is the unstable deleted form.

Cervical carcinoma cell lines were transformed with a SMN2-linked luciferase-reporter gene construct. The reporter is designed to detect shifts in the alternative splicing of SMN2 sequences. In particular, the reporter is constructed as a fusion of the alternatively spliced sequences of the SMN2 gene and the luciferase gene. Luciferase sequences are in the correct translational reading frame only when the SMN2 sequences are spliced according to the normal SMN1 mechanism (e.g., splicing to include exon 7), which allows for translation of the stable SMN protein. Compounds were tested in the assay by administering the compound to the cell line and detecting an increase in the luciferase activity. The assay is described in greater detail in Zhang et al., *Gene Ther.*, 8, 1532-8 (2001). Compounds were administered as described in Lunn et al, *Chem. & Biol*, 11, 1489-1493 (2004).

The compounds tested and the results are reported in Table 1. The results are reported as a fold-increase over a baseline reading of transformed cells without any test compound. The EC50 value also is reported in Table I for some compounds.

Indoprofen increases luciferase activity in this assay. Although this assay is designed to detect correction of the SMN2 splicing defect, it is known that indoprofen does not increase luciferase expression in this assay via effects on splicing. Nonetheless, the effects of indoprofen detected in this assay have been shown to extend to an increase in production of SMN from the endogenous SMN2 gene in SMA patient fibroblasts.

Many of the tested compounds increased luciferase activity in the assay, indicating that the compounds of the invention can be used to increase expression of SMN from the endogenous SMN2 gene.

EXAMPLE 11

This example demonstrates the ability of compounds of the invention to increase GEMs in fibroblasts from SMA patients.

SMN protein can be found in punctate nuclear particles called "gems" (Liu and Dreyfuss, *EMBO J.* 15(14): 3555-3565 (1996)). In fibroblast cells derived from SMA patients, the number of gems corresponds to disease severity as follows: severe type 1 patients have approximately 5 gems per 100 nuclei; mild type 3 patients have 20-50 gems per 100 nuclei; normal individuals have approximately 100-150 gems per 100 nuclei (Coovert et al., *Hum Mol Genet* 6(8): 1205-1214 (1997), Young et al., *Exp Cell Res* 265(2): 252-261 (2001)).

Gems are detectable by immunohistochemistry and gem counts in patient fibroblasts have been used to test the ability of compounds to increase SMN protein levels (Mattis et al., *Hum Genet* 120:589-601 (2006)). Following these methods, fibroblast cells from a type 1 SMA patient (3813 cells, Coriell Cell Repositories) were treated for 48 hours with the compounds indicated in Table 2 (reference number—structure correlation is provided in Table 1). The cells were then fixed and incubated with a monoclonal antibody against SMN (4B7, Wolstencroft et al., *Hum Mol Genet* 14:1199-1210 (2005)). A FITC-conjugated anti-mouse secondary antibody was used to visualize the labeled gems. The positive control in these experiments was provided by fibroblasts from the same patient treated with 1000 μM valproic acid. The results are presented in Table 4.

As the results in Table 4 show, treatment of the cells with each of the compounds increased the number of SMN-containing gems in patient fibroblasts.

TABLE 4

| | | Number of gems per 100 nuclei | | |
|---|---|---|---|---|
| Compound | Concentration (μM) | Treated Cells | Untreated Cells | Positive Control |
| ALB-112355 | 0.45 | 5.3 | 2 | 31 |
| ALB-115806 | 0.4 | 8 | 2 | 31 |
| ALB-113310 | 3 | 53.5 | 4.75 | 48.5 |
| ALB-115069 | 1 | 45.25 | 4.75 | 48.5 |

TABLE 4-continued

| | | Number of gems per 100 nuclei | | |
|---|---|---|---|---|
| Compound | Concentration (μM) | Treated Cells | Untreated Cells | Positive Control |
| ALB-115498 | 1 | 14.3 | 2 | 31 |
| ALB-116244 | 0.1 | 44 | 4.67 | 38.7 |

EXAMPLE 12

The following example demonstrates that compounds of the invention can increase activation of the glutamate transporter promoter.

The astroglial glutamate transporter, GLT-1/EAAT-2, is responsible for the majority of glutamate transport in the brain and spinal cord. To identify compounds capable of inducing EAAT-2 expression, we used a cell-based reporter assay consisting of COS-7 cells stably transfected with a plasmid containing at 2.7 Kb fragment of the human GLT-1/EAAT-2 promoter driving expression of the luciferase reporter (Rothstein et al., *Nature* 433:73-77 (2005). The cell isolate used is designated Cos7 pE2P-GL3 (clone 4). Cells were incubated with compound at the indicated concentrations for 48 h prior to measuring luciferase reporter activity using the Bright-Glo Luciferase Assay System (Promega). Luminescence was measured using a Wallac Trilux microplate luminometer. Results from each plate were normalized to the DMSO treated control wells and expressed as fold-induction. $EC_{50}$ values were calculated using GraphPad Prism software. The results are presented in Table 5.

The results show that some tested compounds significantly increased glutamate transporter promoter activity.

TABLE 5

| Compound ID | Max Fold-Induction | EC50 (nM) |
|---|---|---|
| Positive Control | 1.61 | nd |
| ALB-112354 | 1.93 | 221.2 |
| ALB-112171 | 1.9 | 459.8 |
| ALB-113968 | 1.78 | 1266 |
| ALB-116361 | 1.54 | 6.79 |
| ALB-116255 | 1.2 | NA |
| ALB-116486 | 1.17 | NA |
| ALB-115806 | 0.87 | NA |
| ALB-115498 | 0.86 | NA |

EXAMPLE 13

This example demonstrates the use of compounds of the invention to promote translational read-through of a stop condon.

This assay is described in detail in WO 01/44516 A2. This is a cell-based luciferase reporter assay designed to detect translational read-through via insertion of a translational stop codon within the luciferase coding sequence. In the presence of compounds that promote read-through of translational stop codons, active luciferase is produced and detected via chemiluminescence. We have shown that indoprofen analogs are active in two versions of this assay—one containing a UGA stop codon and one containing a UAG stop codon. The data in the table is from the luciferase reporter containing the UAG stop codon. This is the first stop codon downstream of the improper splice junction between exons 6 and 8 in the human SMN2 transcript. The results are reported in Table 6.

TABLE 6

| Compound ID | Conc at Max Fold (uM) | MaxFold Increase |
|---|---|---|
| Positive Control | 1 | 4.7 |
| Indoprofen | 4 | 2.3 |
| ALB-117573 | 100 | 4.4 |
| ALB-113310 | 1 | 3.7 |
| ALB-117572 | 11 | 3.6 |
| ALB-113648 | 1 | 3.3 |
| ALB-116078 | 4 | 3.3 |
| ALB-114441 | 4 | 3.2 |
| ALB-117454 | 4 | 3.1 |
| ALB-115812 | 11 | 3.0 |
| ALB-113652 | 11 | 2.9 |
| ALB-115210 | 4 | 2.9 |
| ALB-116074 | 4 | 2.9 |
| ALB-117046 | 4 | 2.9 |
| ALB-115948 | 1 | 2.8 |
| ALB-116244 | 4 | 2.8 |
| ALB-111743 | 4 | 2.7 |
| ALB-112355 | 1 | 2.7 |
| ALB-116246 | 4 | 2.7 |
| ALB-114274 | 1 | 2.6 |
| ALB-114783 | 11 | 2.6 |
| ALB-113967 | 4 | 2.6 |
| ALB-114901 | 4 | 2.6 |
| ALB-114844 | 0.4 | 2.4 |
| ALB-116486 | 100 | 2.4 |
| ALB-116932 | 4 | 2.4 |
| ALB-115084 | 1 | 2.3 |
| ALB-115586 | 4 | 2.3 |
| ALB-116362 | 0.7 | 2.3 |
| ALB-112171 | 33 | 2.2 |
| ALB-117452 | 4 | 2.2 |
| ALB-117451 | 11 | 2.1 |
| ALB-112354 | 100 | 2.0 |
| ALB-115806 | 1 | 2.0 |
| ALB-117902 | 4 | 2.0 |
| ALB-113213 | 33 | 1.9 |
| ALB-116935 | 4 | 1.9 |

EXAMPLE 14

This example demonstrates the plasma and brain pharmacokinetics of compounds of the invention.

Compounds were formulated in solution using the method of cosolvency as described by Lee et al., Int. J. Pharmaceutics, 253: 111-119 (2003). FVB or CD-1 mice, approximately 5 weeks old, were given a single dose of compound at the indicated concentration. Compounds were administered orally, with the exception of ALB-116638 and ALB-117573, which were administered IV. Three to five mice were euthanized at various times between 15 minutes and 24 hours after dosing and brain and plasma were harvested. Tissues were homogenized in acetonitrile and analyzed on an API 4000 LC/MS/MS system coupled with an Agilent 1100 series liquid chromatograph. All pharmacokinetic analyses were conducted using WinNonlin (Version 4.01; Pharsight, Palo Alto, Calif.) with the exception of brain/plasma ratios, which were calculated using Microsoft Excel 2000. AUC values are the area under the concentration-time curve from time zero to the last measured time point. The half life values are extrapolated from 3-4 time points taken at less than 4 hours after dosing.

TABLE 7

| ALB # | Dose (mg/kg) | Brain AUC (h * ng/g) | Plasma AUC (h * ng/mL) | Brain/Plasma Ratio | Brain T½ (hours) | Plasma T½ (hours) |
|---|---|---|---|---|---|---|
| 112355 | 5 | 570.0 | 21099.0 | 0.03 | 2.6 | 7.6 |
| 113967 | 5 | 170.5 | 595.4 | 0.29 | 1.1 | 1.5 |
| 115210 | 5 | 553.8 | 10.7 | 51.7 | 0.6 | 9.4 |
| 115210 | 25 | 5950.9 | 396.9 | 15 | 2.9 | 1.1 |
| 116935 | 5 | 338.1 | nd | nd | 9.4 | nd |
| 115498 | 5 | 163.8 | 47.8 | 3.43 | 0.5 | 0.6 |
| 116638 | 5 | 537.2 | nd | nd | 7.3 | nd |
| 117573 | 5 | 64.5 | nd | nd | 7.4 | nd |

EXAMPLE 15

Westerns blots were performed using the methods of Mattis et al., Hum Genet 120:589-601(2006)). SMA type I fibroblasts (3813 cells; Coriell Cell Repositories) were treated with compounds for 48 hours. Monoclonal anti-SMN antibody 4B7 (Wolstencroft et al., Hum Mol Genet 14:1199-1210 (2005)) was used to identify SMN. Actin was used as an internal normalization standard and detected with an anti-actin polyclonal rabbit antibody (Sigma-Aldrich). Tobramycin was used for the positive control compound treatment. DMSO is the untreated negative control. The results are presented in Table 8. Values are presented as the ratio of the signals obtained for SMN and Actin.

TABLE 8

| Compound | Concentration (uM) | SMN:Actin Ratio |
|---|---|---|
| DMSO | n/a | 1 |
| Tobramycin | 320 | 1.5 |
| ALB-113310 | 0.1 | 4.8 |
|  | 1 | 6.2 |
| ALB-115069 | 0.1 | 4.3 |
|  | 1 | 5.7 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of Formula I:

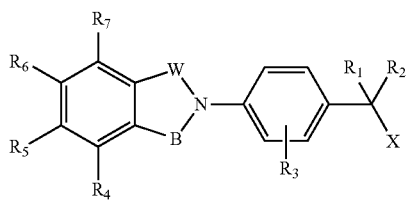

wherein,
W is C(O) or C(S);
B is $CH_2$ or $CH(C_nH_{2n+1})$, wherein n is an integer from 1 to 8;
$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;
$R_3$ is selected from the group consisting of H, halogen, $C_1$-$C_4$ alkyl, $C_1$-$C_4$ alkoxy, $C_1$-$C_4$ haloalkyl, $C_1$-$C_6$ haloalkoxy, $C_2$-$C_6$ alkenyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy;
$R_4$, $R_5$, $R_6$ and $R_7$ are independently selected from the group consisting of H, hydroxyl, halogen, CN, $NO_2$, sulfonamide, $C_1$-$C_8$ alkyl, $C_3$-$C_6$ cycloalkyl, $C_1$-$C_6$ alkoxy, $C_1$-$C_4$ haloalkyl, $C_1$-$C_6$ haloalkoxy, $C_2$-$C_8$ alkenyl, amino, $C_1$-$C_4$ dialkyl amino, $C_1$-$C_4$ alkylamino, $C_3$-$C_6$ cycloalkylamino, morpholinyl, heteroaryl, arylamino, arylalkylamino, phenyl, C(O)R', NR'(COR''), NR'$SO_2$R'' and NR'(CONR''R'''); wherein R', R'' and R''' are independently H, $C_1$-$C_6$ alkyl, phenyl or substituted phenyl; and wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, arylamino, arylalkylamino, and morpholinyl; and the phenyl is optionally substituted with one or more members selected from the group consisting of halogen, $NO_2$, CN, $C_1$-$C_4$ alkyl, $C_1$-$C_4$ haloalkyl, and $C_1$-$C_4$ alkoxy;
wherein at least $R_5$, $R_6$, or both are further selected from the group consisting of hydroxyl, halogen, CN, $NO_2$, sulfonamide, $C_1$-$C_8$ alkyl, $C_3$-$C_6$ cycloalkyl, $C_1$-$C_6$ alkoxy, $C_1$-$C_4$ haloalkyl, $C_1$-$C_6$ haloalkoxy, $C_2$-$C_8$ alkenyl, amino, $C_1$-$C_4$ dialkyl amino, $C_1$-$C_4$ alkylamino, $C_3$-$C_6$ cycloalkylamino, morpholinyl, heteroaryl, arylalkylamino, phenyl, C(O)R', NR'(COR''), NR'$SO_2$R'' and NR'(CONR''R'''); wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, arylamino, arylalkylamino, and morpholinyl; and the phenyl is optionally substituted with one or more members selected from the group consisting of halogen, $NO_2$, CN, $C_1$-$C_4$ alkyl, $C_1$-$C_4$ haloalkyl, and $C_1$-$C_4$ alkoxy;
or $R_4$ and $R_5$, $R_5$ and $R_6$, or $R_6$ and $R_7$ taken together with the carbon atoms to which they are attached form a dioxane or dioxolane ring;
X is selected from the group consisting of
H;
CN;
$C(O)NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached faun a $C_5$-$C_6$ cycloalkyl ring or a heteroring such as morphline;
$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;
$CH_2Z$, wherein Z is halogen;
C(O)NHOH;
C(O)NHCN;
$C(O)N(R_1)SO_2R_{13}$, wherein $R_{13}$ is $C_1$-$C_4$ alkyl, phenyl, or substituted phenyl;
$C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; and
$C_2$-$C_8$ alkenyl optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino.
2. The compound of claim 1, wherein:
B is $CH_2$;
$R_4$, $R_5$, $R_6$ and $R_7$ are independently selected from the group consisting of H, halogen, CN, $NO_2$, sulfonamide, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, morpholinyl, heteroaryl, and phenyl, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl, and the phenyl is optionally substituted with one or more members selected from the group consisting of halogen, $NO_2$, CN, $C_1$-$C_4$ alkyl, $C_1$-$C_4$ haloalkyl, and $C_1$-$C_4$ alkoxy;
wherein at least $R_5$, $R_6$, or both are further selected from the group consisting of halogen, $C_1$-$C_8$ alkyl, $C_3$-$C_6$ cycloalkyl, $C_1$-$C_6$ alkoxy, $C_1$-$C_4$ haloalkyl, $C_1$-$C_4$ dialkyl amino, $C_1$ $C_4$ alkylamino, $C_3$-$C_6$ cycloalkyl amino, and morpholinyl, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;
X is selected from the group consisting of
CN;
$C(O)NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heteroring such as morphline;

$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;

$CH_2Z$, wherein Z is halogen;

C(O)NHOH;

C(O)NHCN;

$C(O)N(R_1)SO_2R_{13}$, wherein $R_{13}$ is $C_1$-$C_4$ alkyl, phenyl, or substituted phenyl;

$C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; and $C_2$-$C_8$ alkenyl optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino.

3. The compound of claim 1, wherein X is selected from the group consisting of

CN;

$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;

$C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino.

4. The compound of claim 1, wherein $R_1$ and $R_2$ are independently selected from the group consisting of H and $C_1$-$C_3$ alkyl.

5. The compound of claim 1, wherein $R_5$ and $R_6$ are independently selected from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, and morpholinyl, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl.

6. The compound of claim 1, wherein $R_7$ is selected from the group consisting of halogen, $C_1$-$C_8$ alkyl, $C_3$-$C_6$ cycloalkyl, $C_1$-$C_6$ alkoxy, $C_1$-$C_4$ haloalkyl, amino, $C_1$-$C_4$ dialkyl amino, $C_1$-$C_4$ alkylamino, $C_3$-$C_6$ cycloalkyl amino, and morpholinyl, wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl.

7. The compound of claim 1, wherein X is selected from the group consisting of

CN;

$C(O)NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heteroring such as morphline;

$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;

$CH_2NR_9R_{10}$, wherein $R_9$ and $R_{10}$ are as defined above, $CH_2Z$, wherein Z is halogen;

C(O)NHOH;

C(O)NHCN; and $C(O)N(R_1)SO_2R_{13}$, wherein $R_{13}$ is $C_1$-$C_4$ alkyl, phenyl, or substituted phenyl.

8. The compound of claim 7, wherein X is selected from the group consisting of

CN;

$CH_2OR_{11}$, wherein $R_{11}$ is H, $C_1$-$C_8$ alkyl, or $C_3$-$C_6$ cycloalkyl, wherein the $C_1$-$C_8$ alkyl is optionally substituted one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;

$CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heteroring such as morphline; and $CH_2Z$, wherein Z is halogen.

9. The compound of claim 1, wherein X is selected from the group consisting of $C_1$-$C_8$ alkyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino; and $C_1$-$C_8$ alkenyl, optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino.

10. A compound according to claim 1, wherein the compound is:

167
-continued
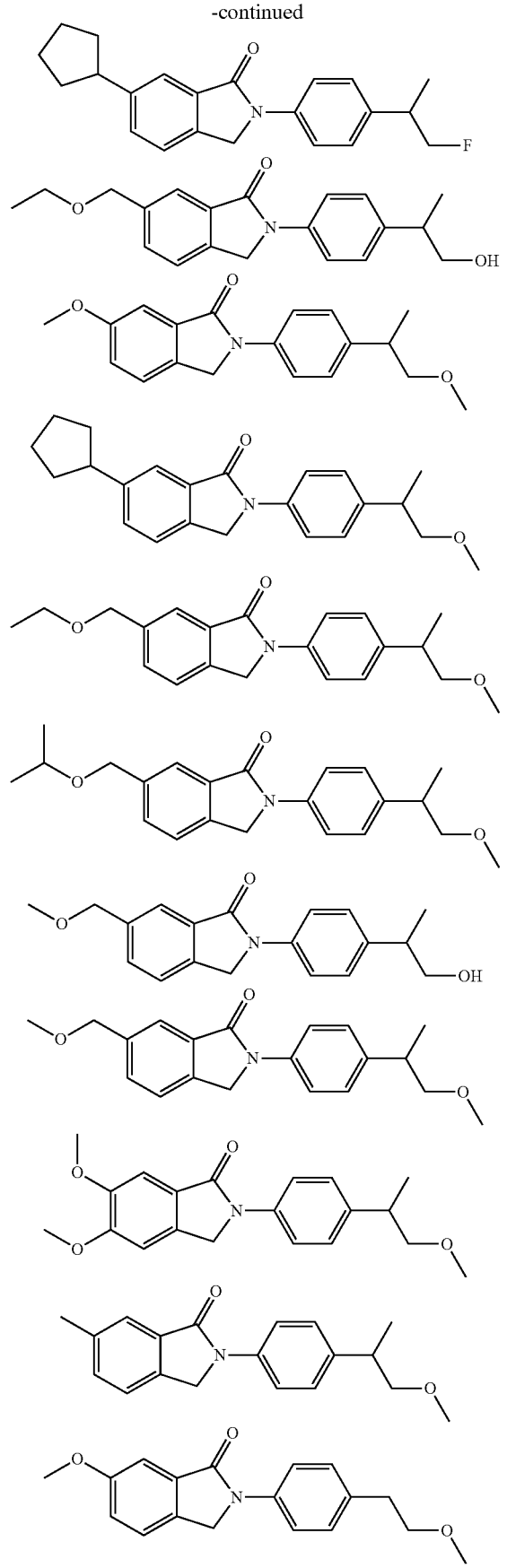
168
-continued
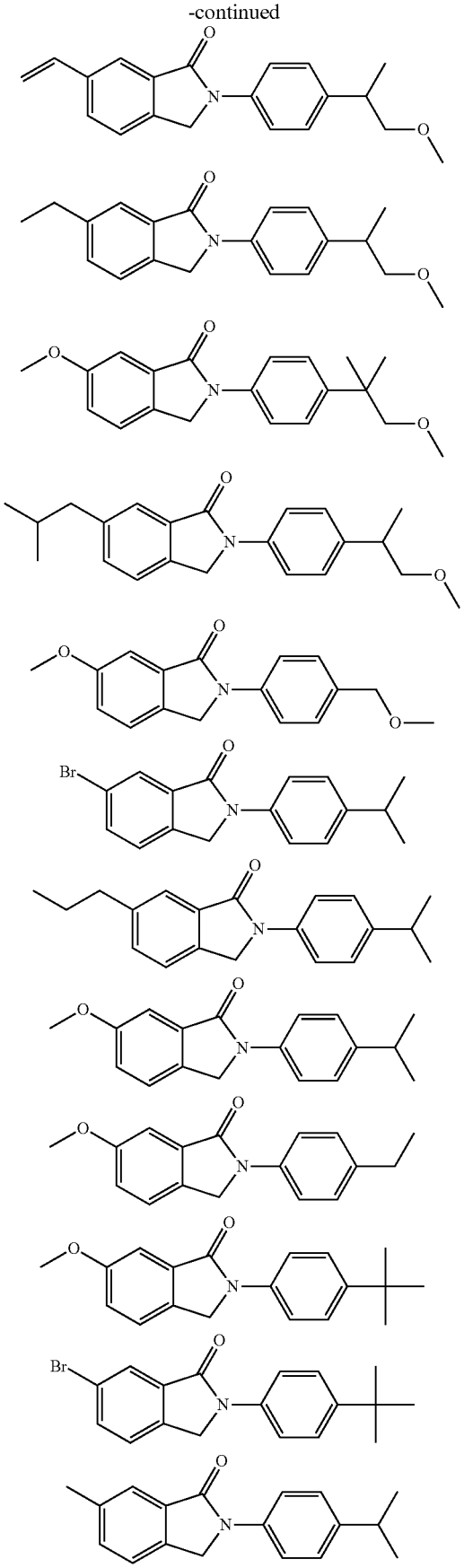

| 169 -continued | 170 -continued |
|---|---|
| 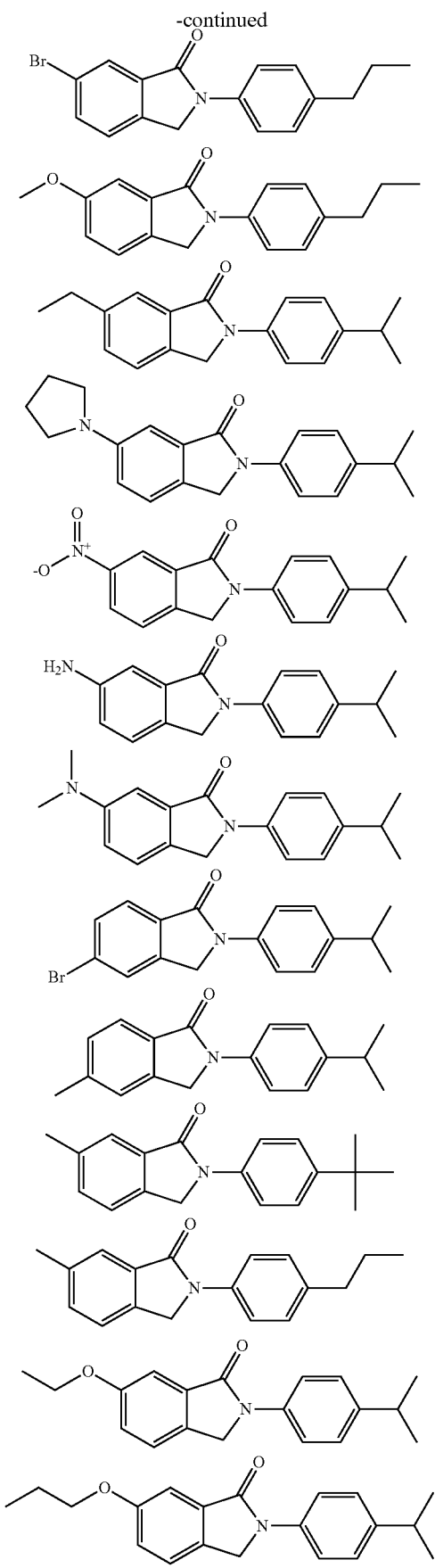 | 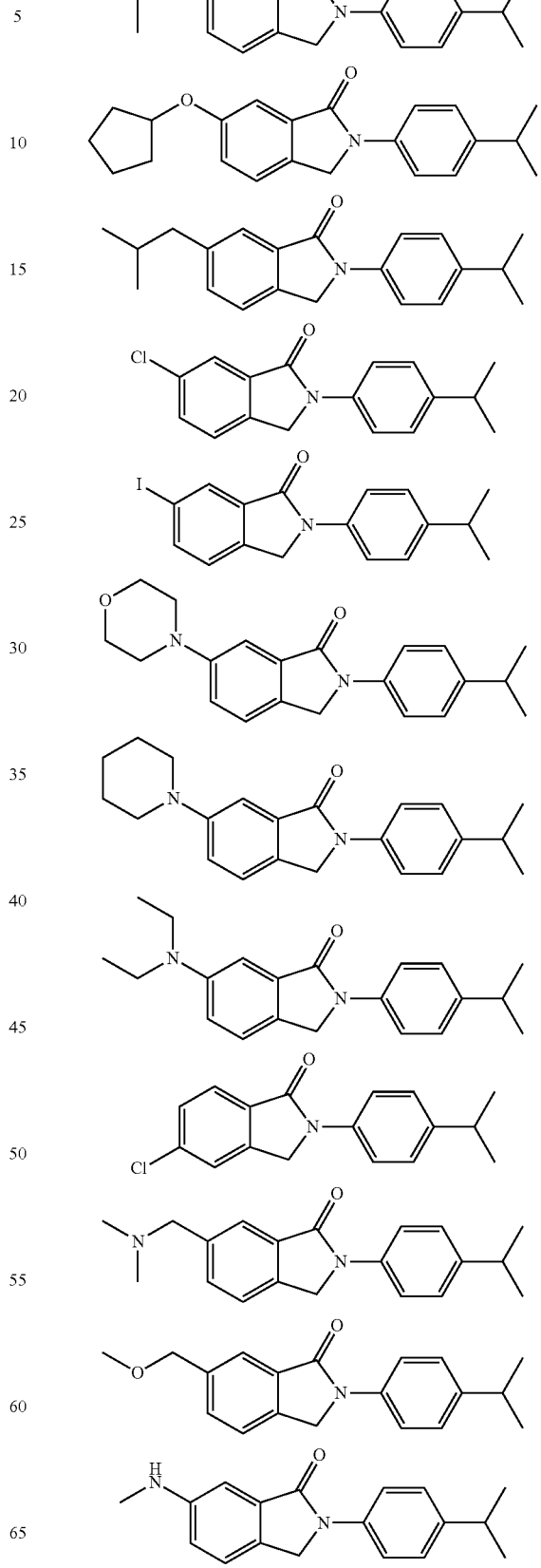 |

-continued
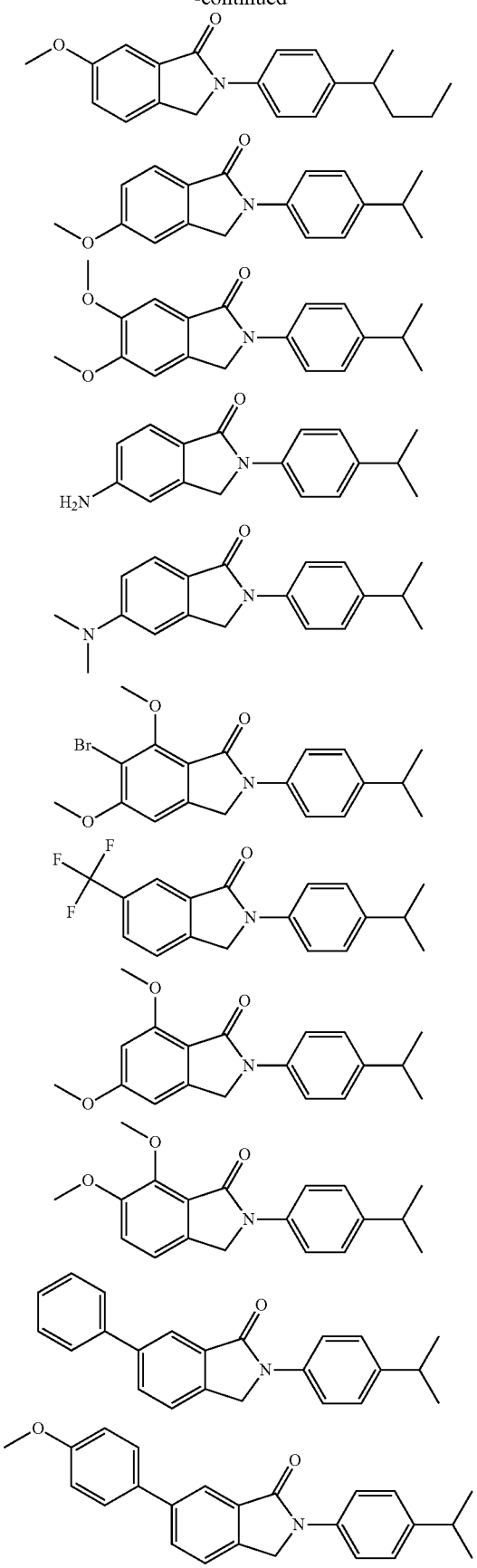
-continued
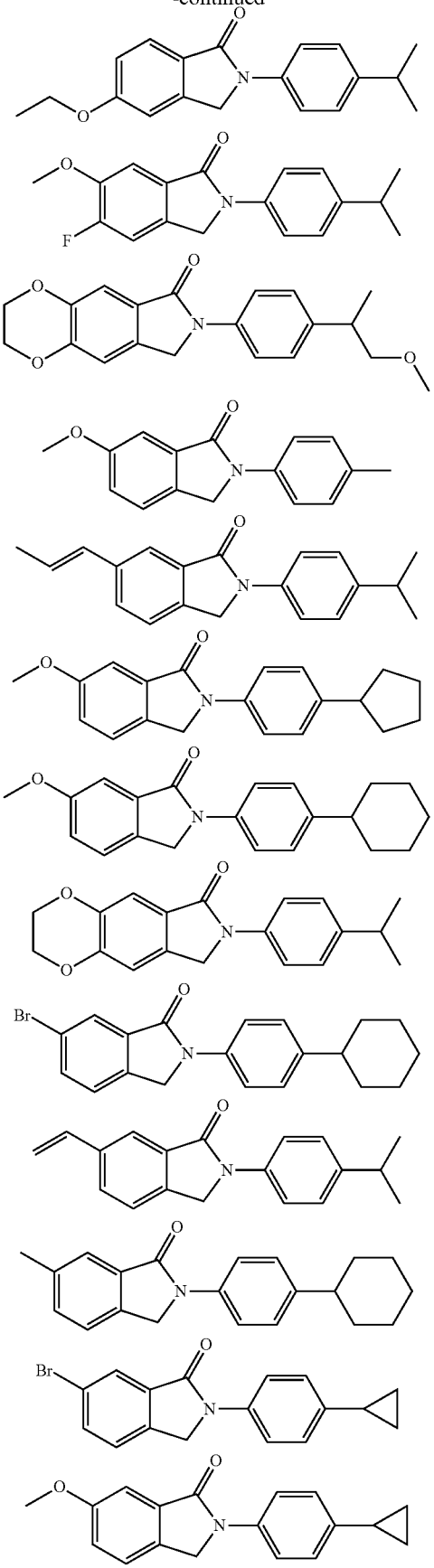

173
-continued
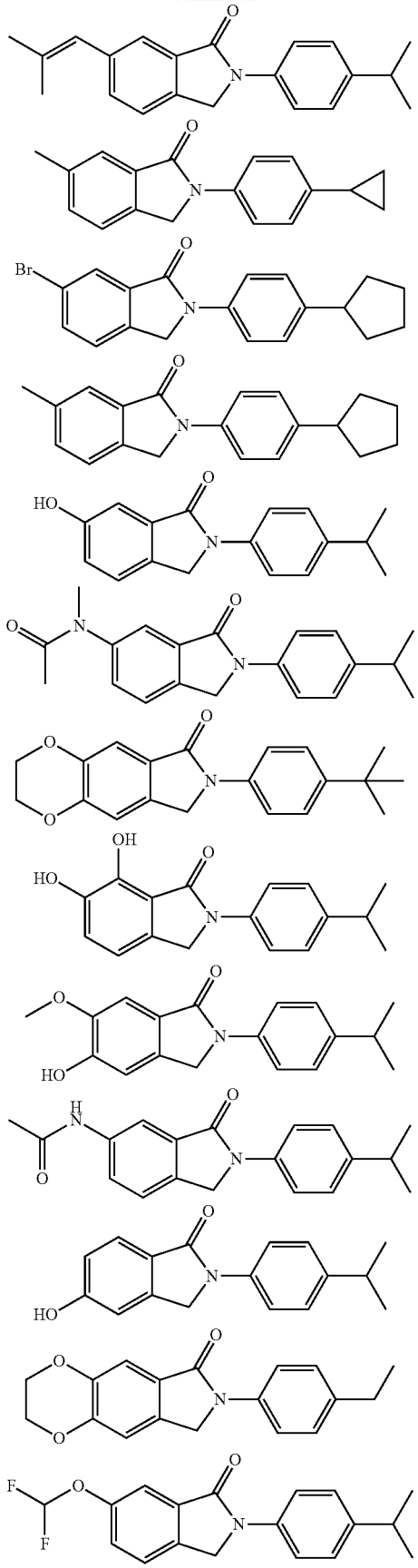
174
-continued
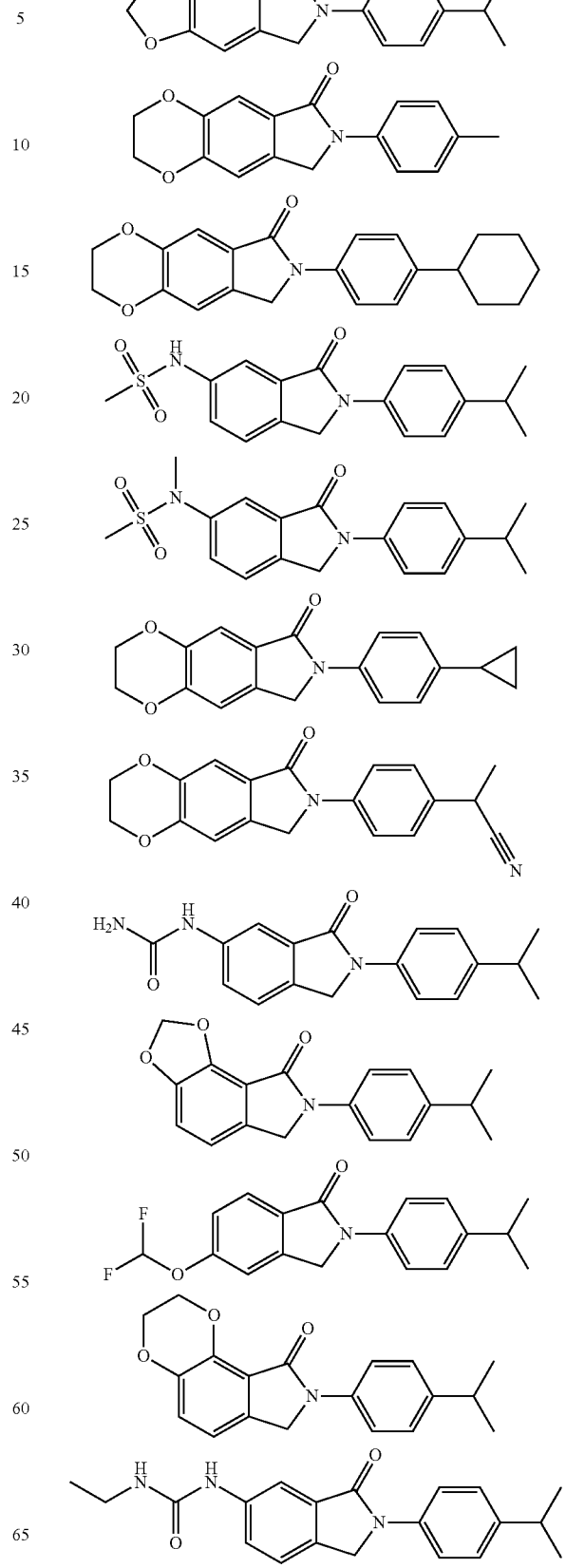

11. A composition comprising a compound of claim 1, and a carrier.

12. A compound of Formula I:

*I* wherein,
W is C(O) or C(S);
B is CH₂ or CH(C_nH_{2n+1}), wherein n is an integer from 1 to 8;
R₁ and R₂ are independently selected from the group consisting of H and C₁-C₃ alkyl, or R₁ and R₂ may be taken together with the carbon atom to which they are attached to form a C₃-C₆ cycloalkyl ring or a carbonyl group;
R₃ is selected from the group consisting of H, halogen, C₁-C₄ alkyl, C₁-C₄ alkoxy, C₁-C₄ haloalkyl, C₁-C₆ haloalkoxy, C₂-C₆ alkenyl, CN, NO₂, heteroaryl, and phenyl optionally substituted with any combination of one to five halogen, NO₂, CN, C₁-C₄ alkyl, C₁-C₄ haloalkyl, or C₁-C₄ alkoxy;
R₄, R₅, R₆ and R₇ are independently selected from the group consisting of H, hydroxyl, halogen, CN, NO₂, sulfonamide, C₁-C₈ alkyl, C₃-C₆ cycloalkyl, C₁-C₆ alkoxy, C₁-C₄ haloalkyl, C₁-C₆ haloalkoxy, C₂-C₈ alkenyl, amino, C₁-C₄ dialkyl amino, C₁-C₄ alkylamino, C₃-C₆ cycloalkylamino, morpholinyl, heteroaryl, arylamino, arylalkylamino, phenyl, C(O)R', NR'(COR"), NR'SO₂R" and NR'(CONR"R'''); wherein R', R" and R''' are independently H, C₁-C₆ alkyl, phenyl or substituted phenyl; and wherein the C₁-C₈ alkyl is optionally substituted with one or more members selected from the group consisting of C₁-C₄ alkoxy, C₁-C₄ haloalkyl, C₁-C₆ dialkyl amino, C₁-C₆ alkylamino, cycloalkylamino, arylamino, arylalkylamino, and morpholinyl; and the phenyl is optionally substituted with one or more members selected from the group consisting of halogen, NO₂, CN, C₁-C₄ alkyl, C₁-C₄ haloalkyl, and C₁-C₄ alkoxy;
wherein at least one of R₄, R₅, R₆ and R₇ is selected from the group consisting of CN, NO₂, sulfonamide, C₃-C₆ cycloalkyl, C₁-C₄ haloalkyl, C₁-C₆ haloalkoxy, C₂-C₈ alkenyl, amino, C₁-C₄ dialkyl amino, C₁-C₄ alkylamino, C₃-C₆ cycloalkylamino, morpholinyl, heteroaryl, arylamino, arylalkylamino, phenyl, C(O)R', NR'(COR"), NR'(COR") NR'SO₂R", NR'(CONR"R'''), and C₁-C₈ alkyl substituted with one or more members selected from the group consisting of C₁-C₄ alkoxy, C₁-C₄ haloalkyl, C₁-C₆ dialkyl amino, C₁-C₆ alkylamino, cycloalkylamino, arylamino, arylalkylamino, and morpholinyl; wherein R', R" and R" are independently H, C₁-C₆ alkyl, and phenyl optionally substituted with one or more members selected from the group consisting of halogen, NO$_2$, CN, C$_1$-C$_4$ alkyl, C$_1$-C$_4$ haloalkyl, and C$_1$-C$_4$ alkoxy;

or R$_4$ and R$_5$, R$_5$ and R$_6$, or R$_6$ and R$_7$ taken together with the carbon atoms to which they are attached form a dioxane or dioxolane ring;

X is

C(O)OR$_8$, wherein R$_8$ is H or C$_1$-C$_8$ alkyl wherein the alkyl optionally is substituted with one or members selected from the group consisting of C$_1$-C$_4$ alkoxy, C$_1$-C$_4$ haloalkyl, C$_1$-C$_6$ dialkyl amino, C$_1$-C$_6$ alkylamino, cycloalkylamino, phenyl, and morpholinyl.

13. A compound of claim 12, wherein the compound is:

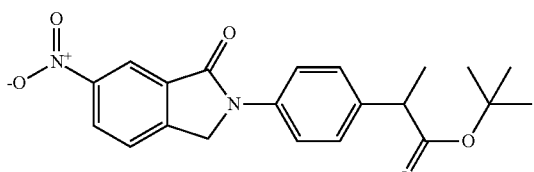
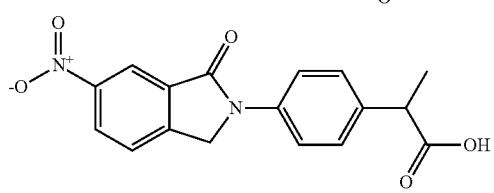
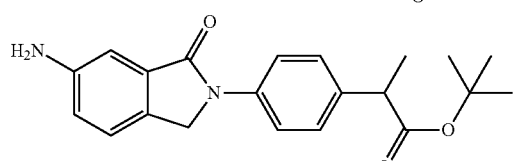
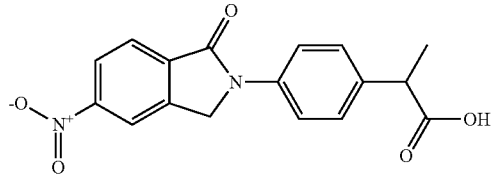
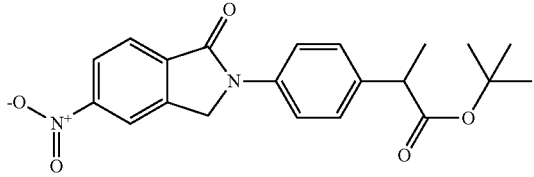
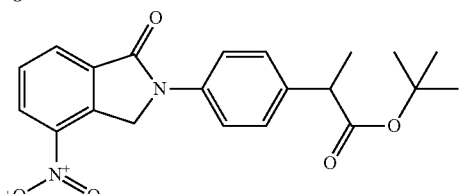
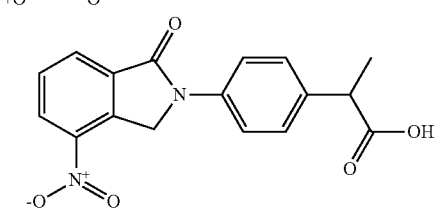

-continued

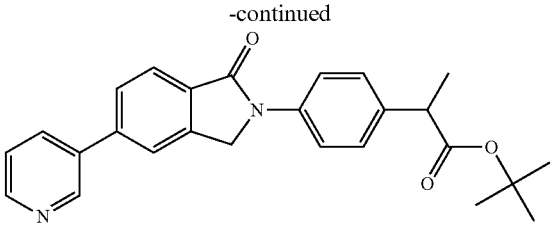
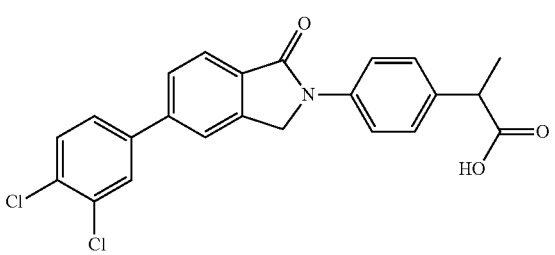
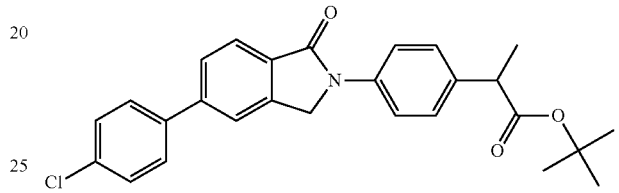
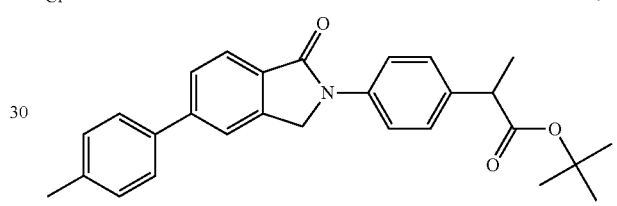
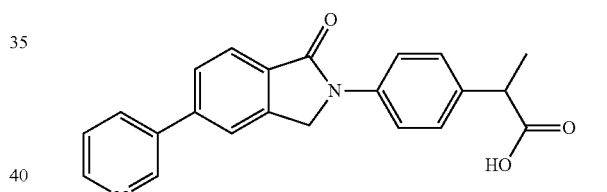
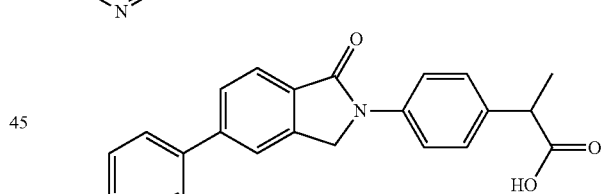
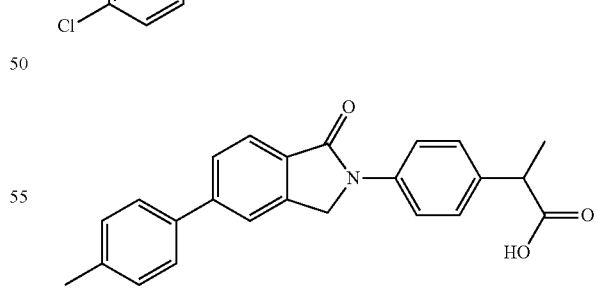
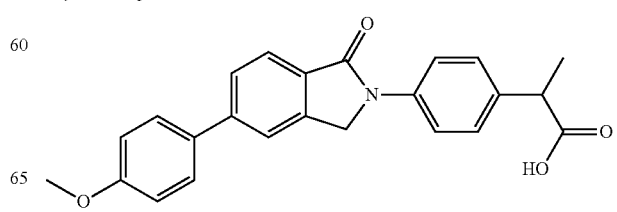

179
-continued
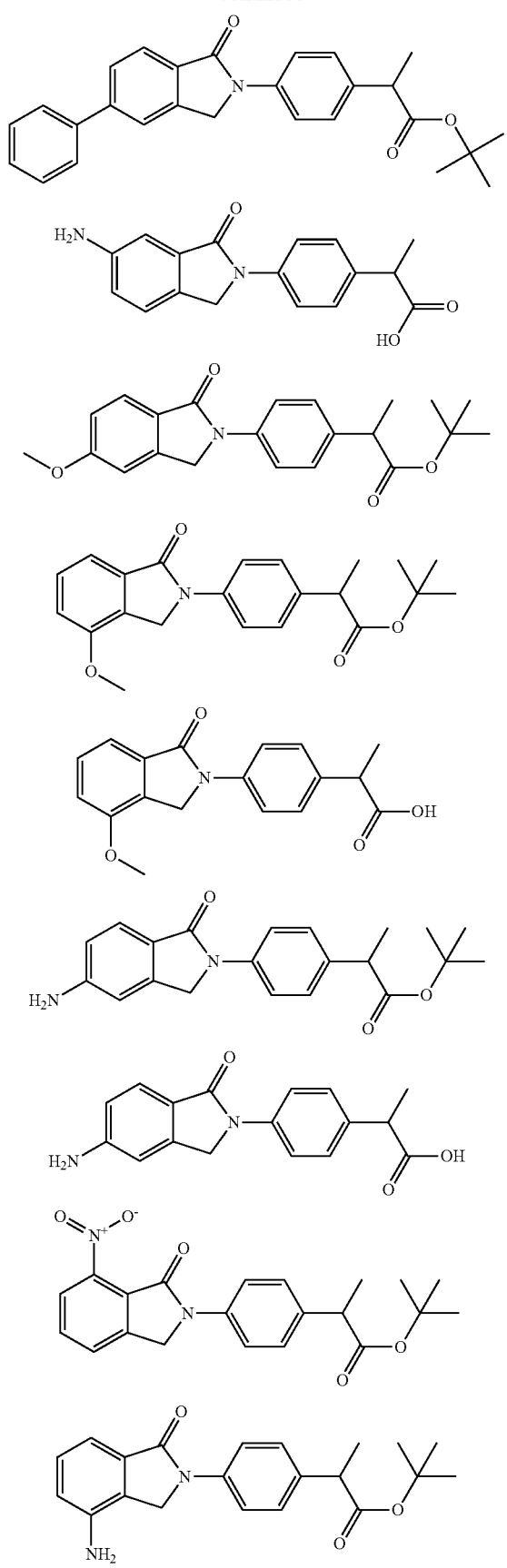
180
-continued
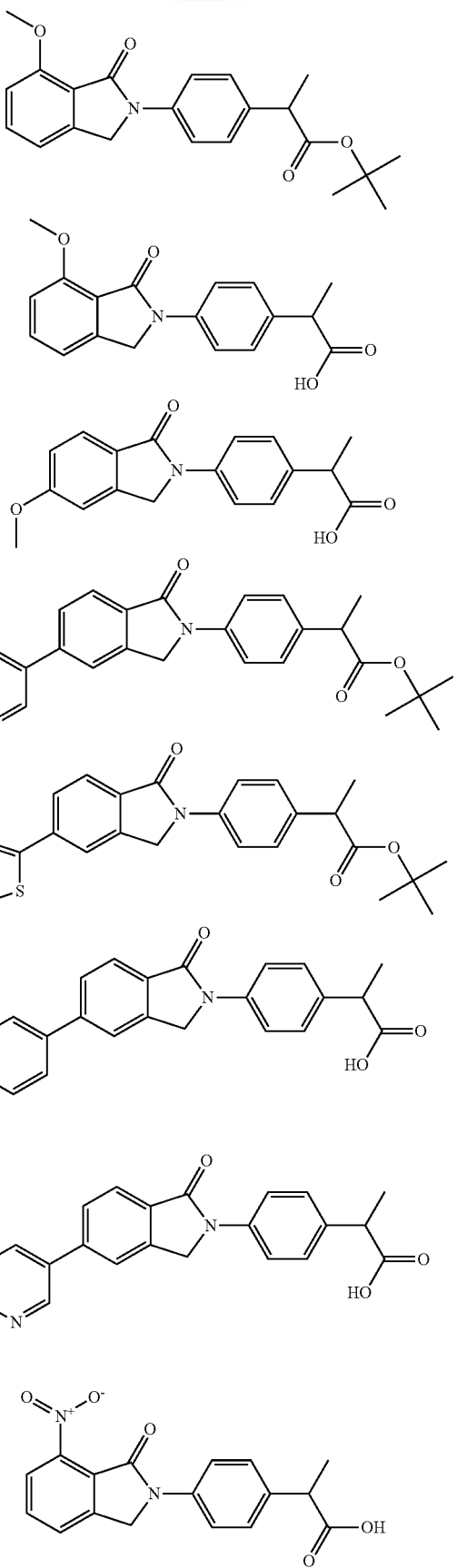

181
-continued
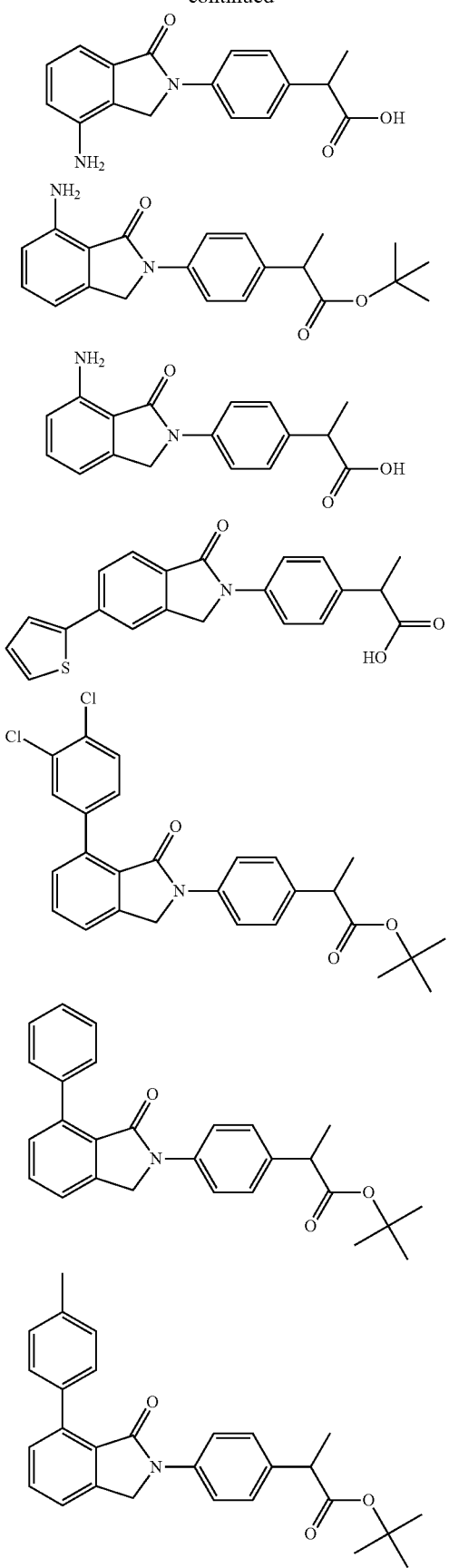
182
-continued
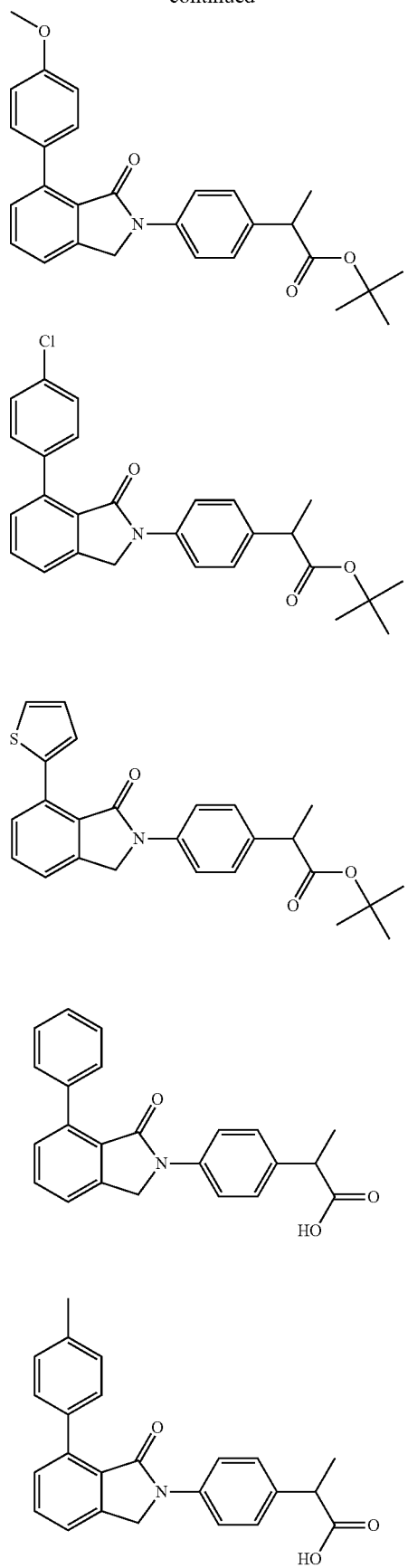

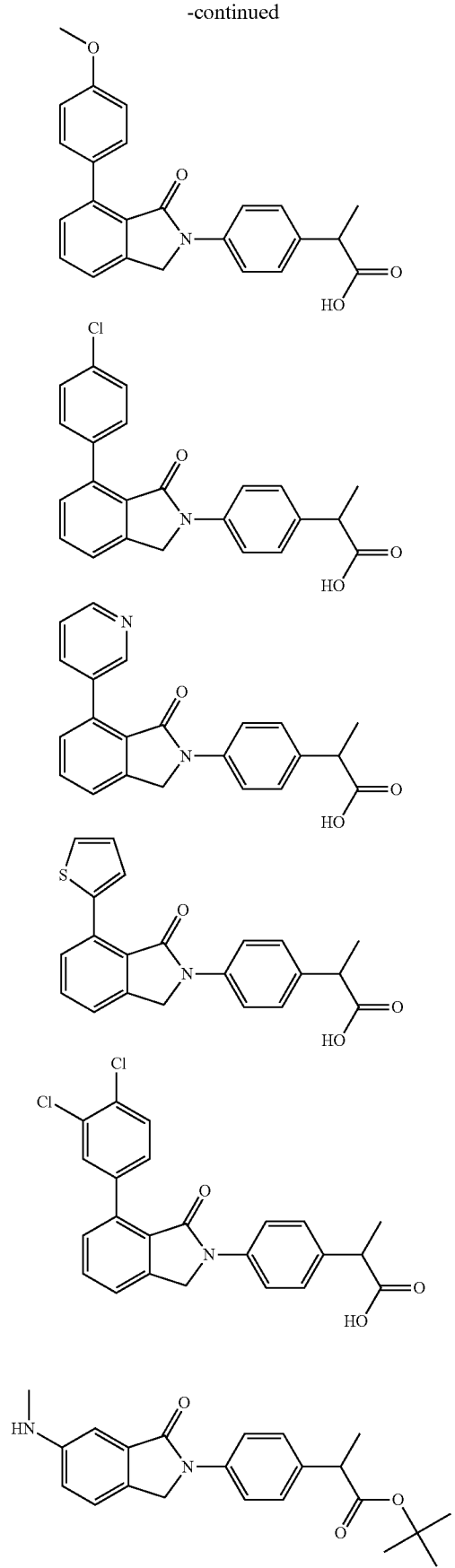
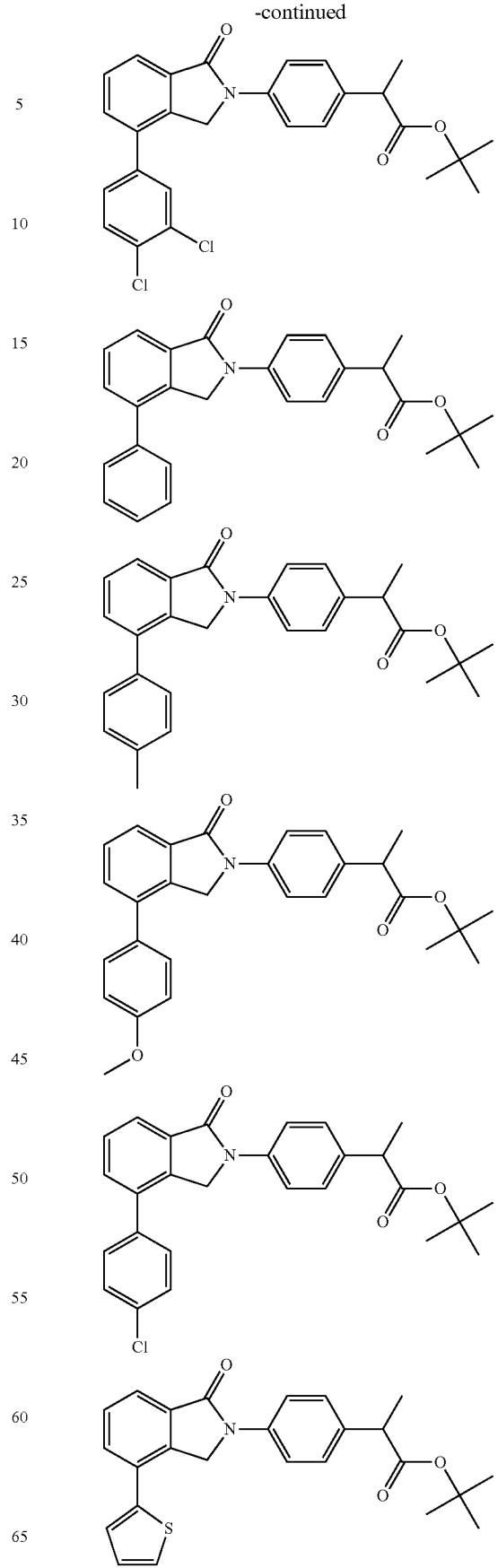

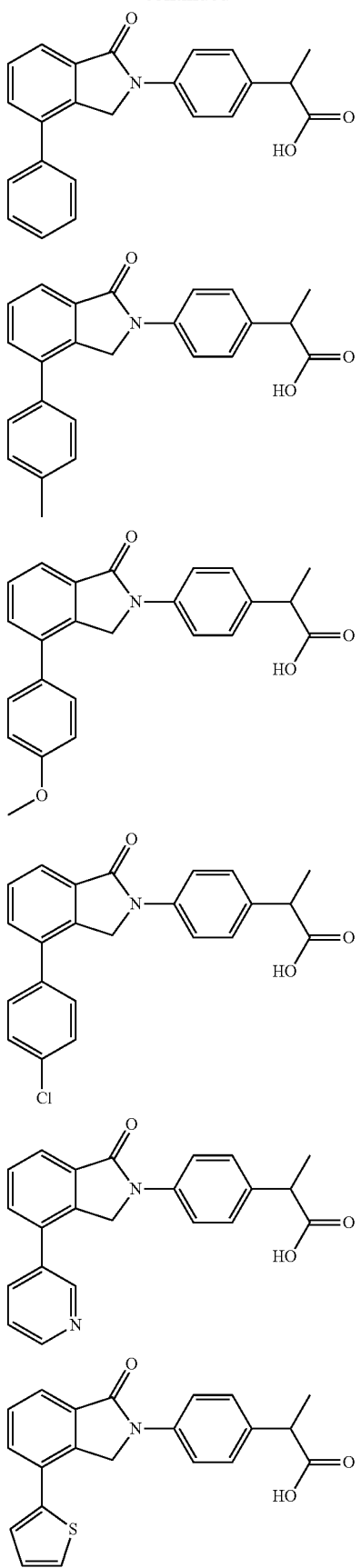
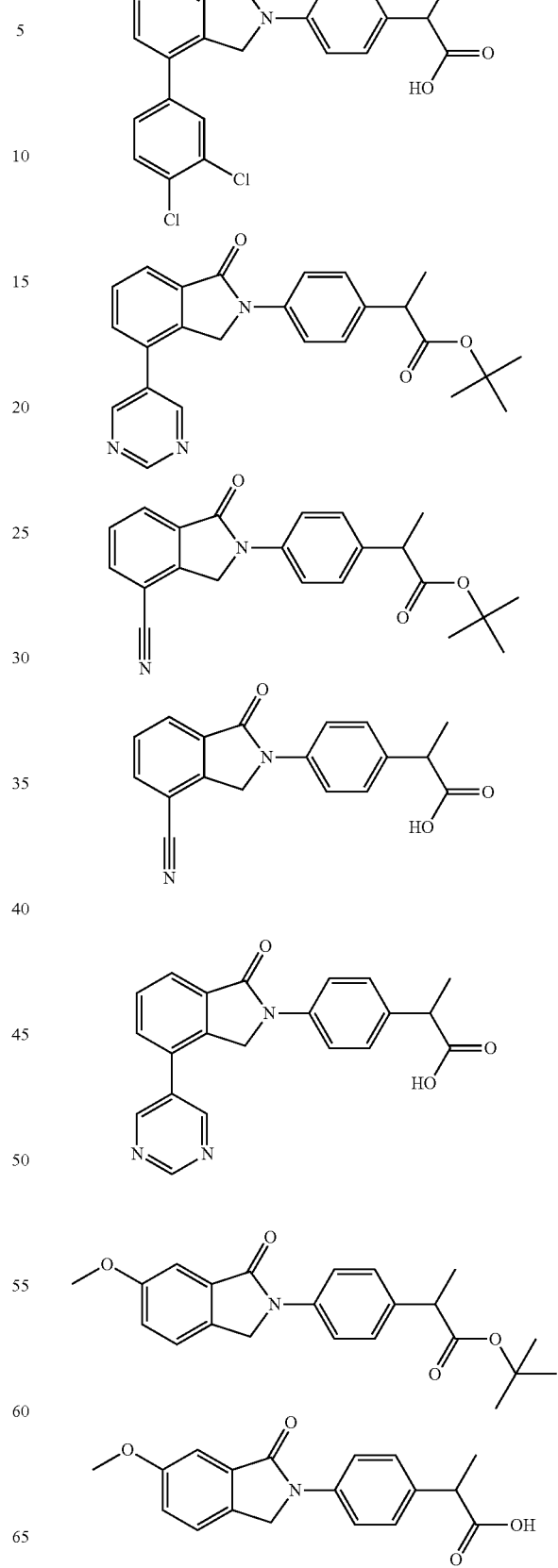

187
-continued
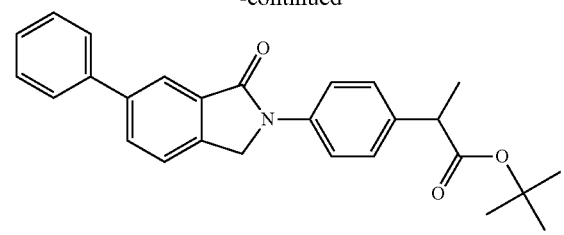
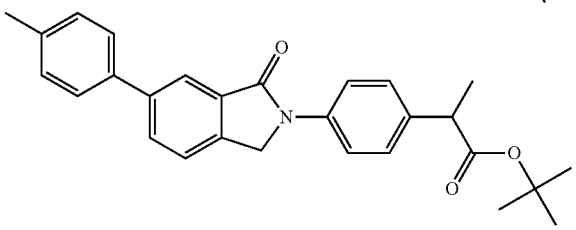
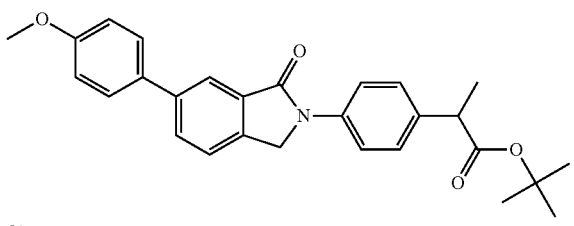
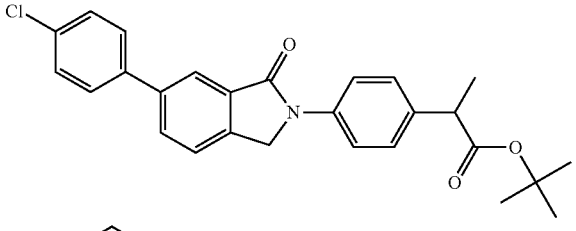
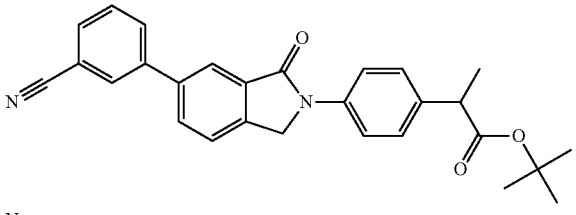
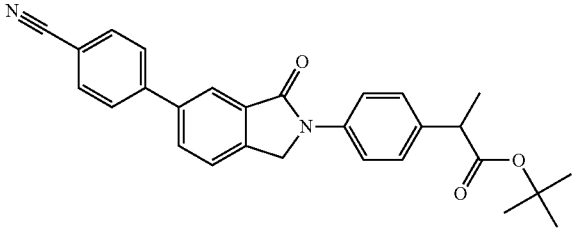
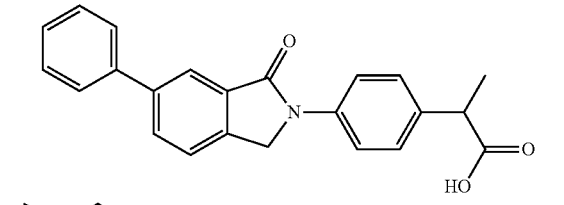
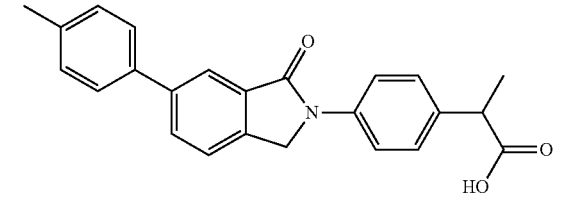
188
-continued
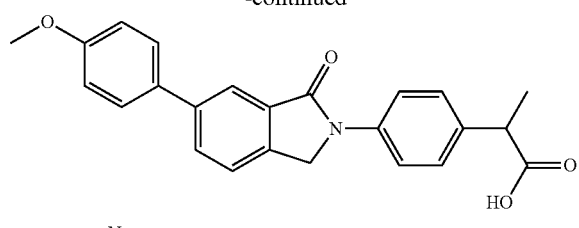
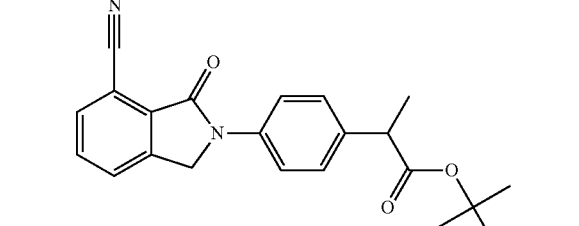
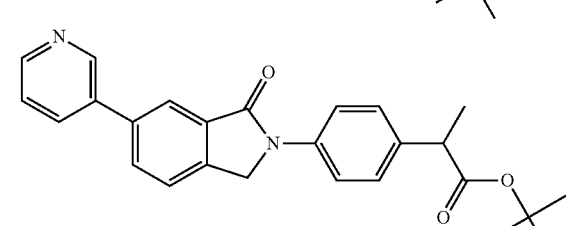
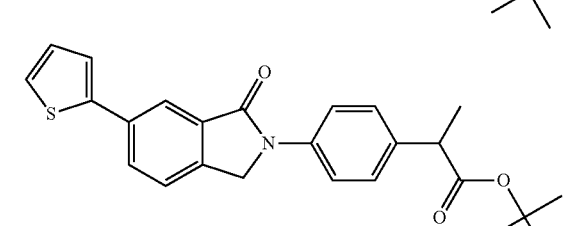
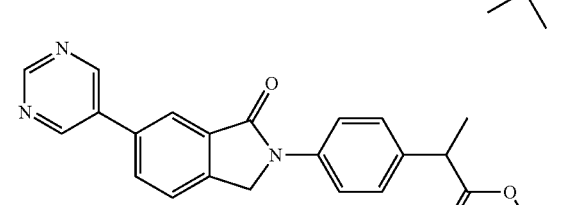
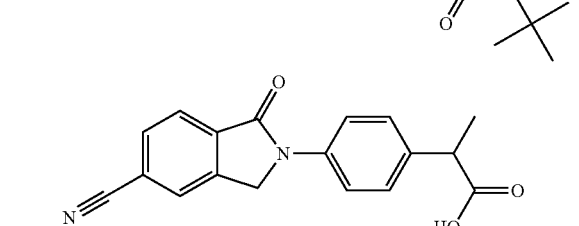
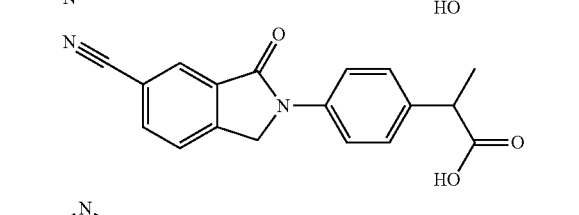
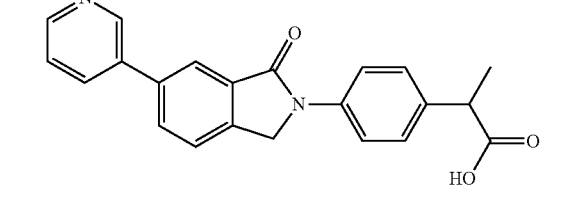

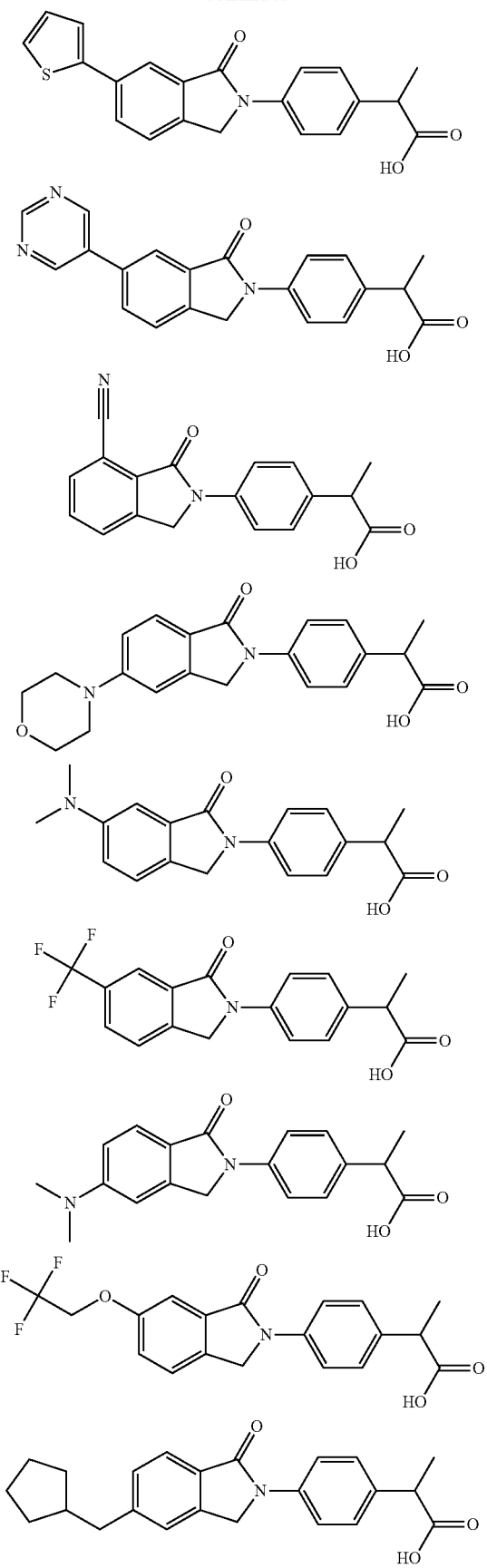
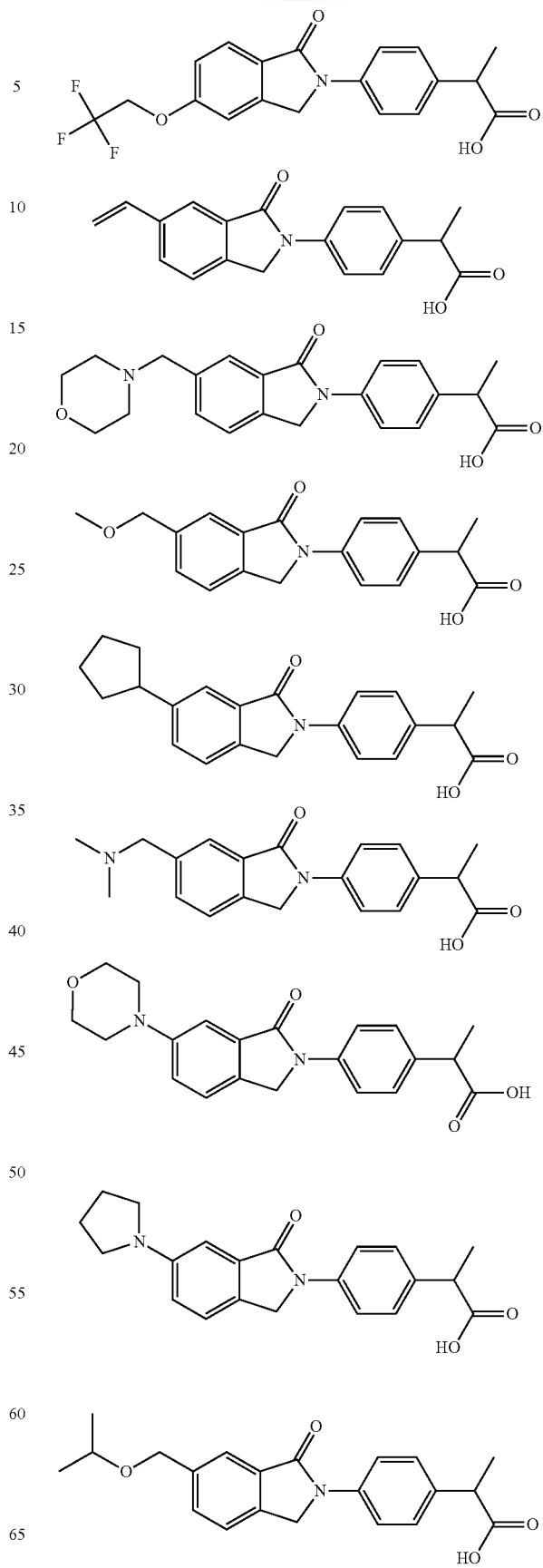

191
-continued
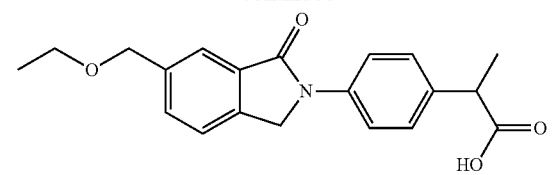
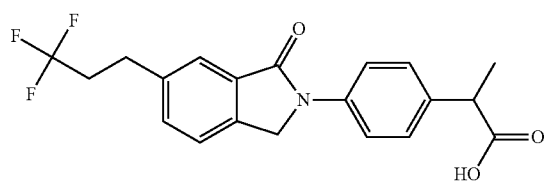
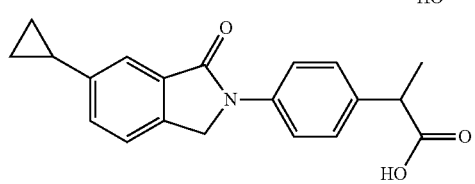
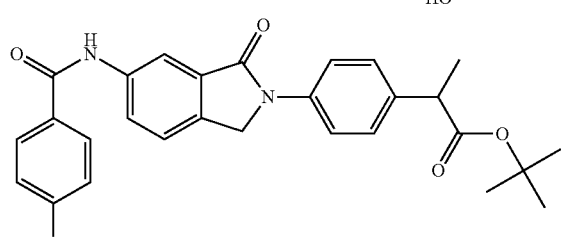
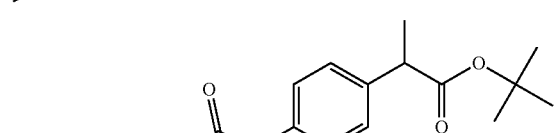
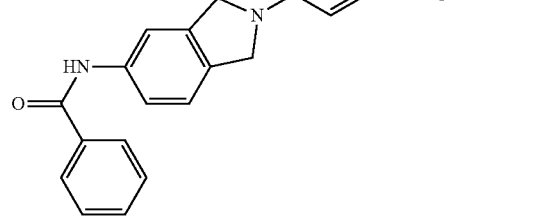
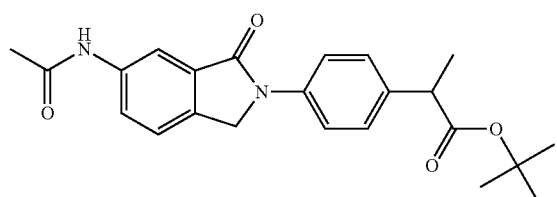
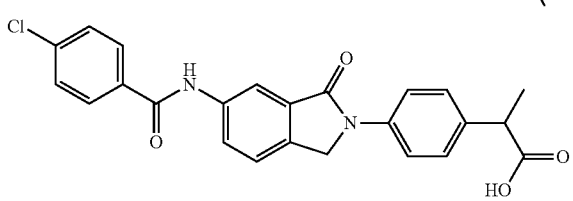
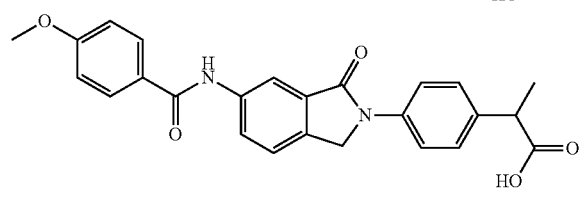
192
-continued
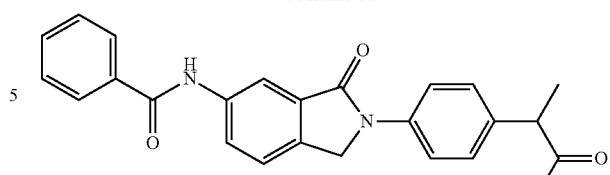
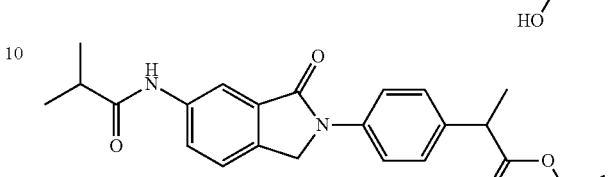
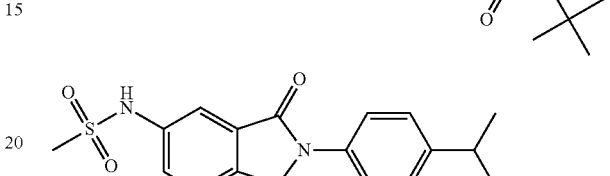
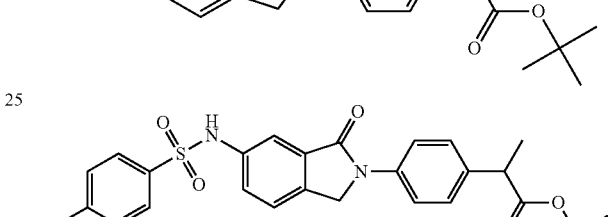
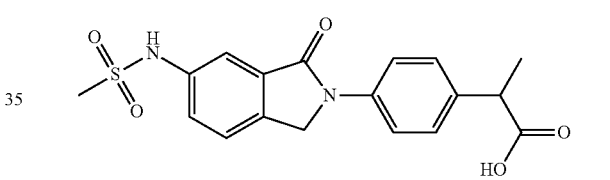
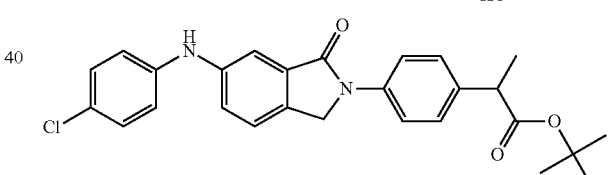
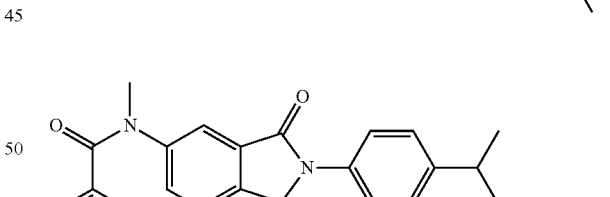
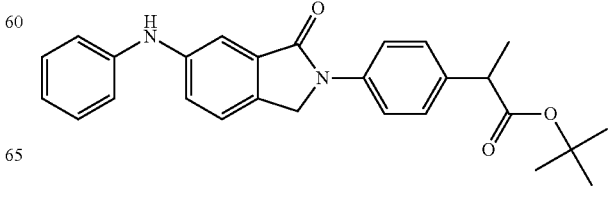

193
-continued
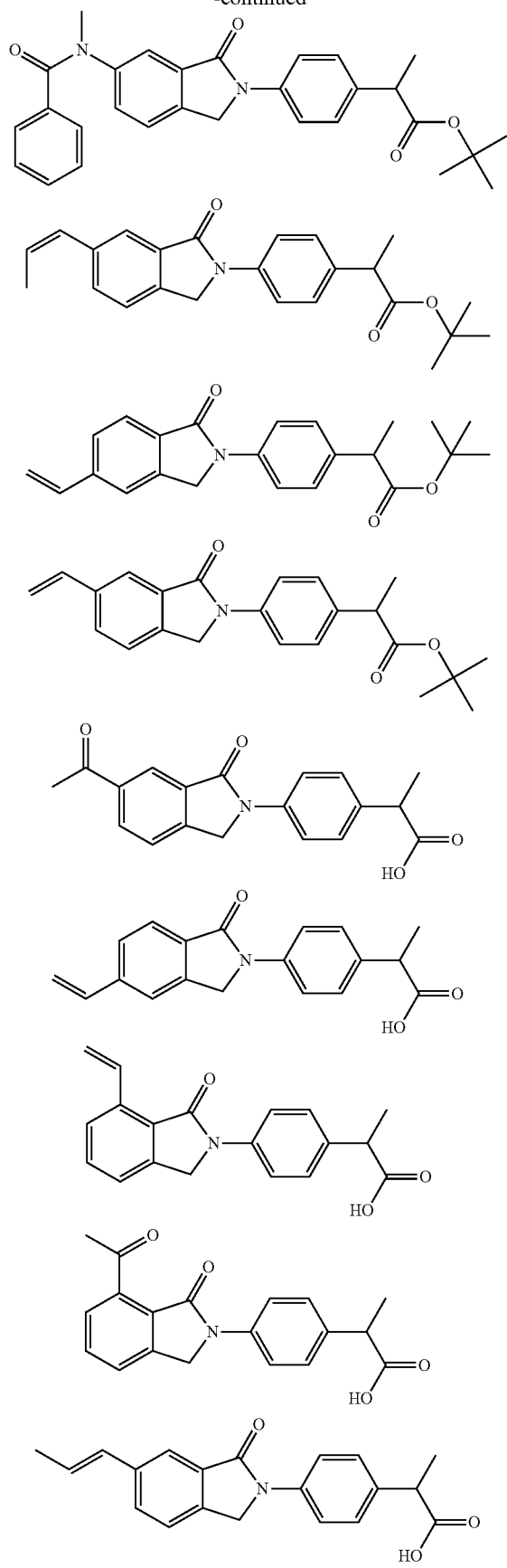
194
-continued
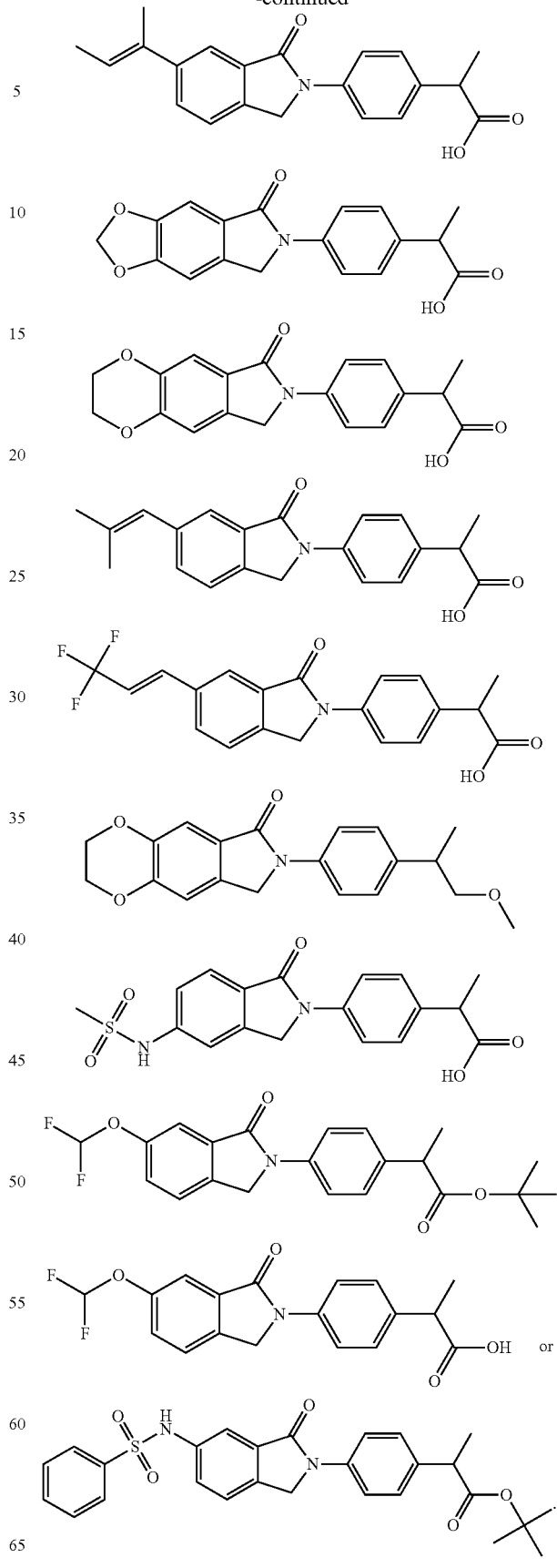

14. A compound of Formula I:

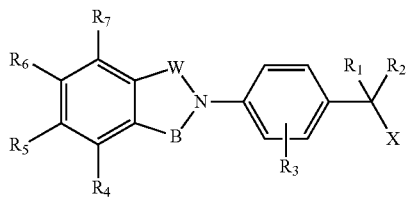

wherein,
W is C(O) or C(S);
B is $CH_2$ or $CH(C_nH_{2n+1})$, wherein n is an integer from 1 to 8;
$R_1$ and $R_2$ are independently selected from the group consisting of H and $C_1$-$C_3$ alkyl, or $R_1$ and $R_2$ may be taken together with the carbon atom to which they are attached to form a $C_3$-$C_6$ cycloalkyl ring or a carbonyl group;
$R_3$ is selected from the group consisting of H, halogen, $C_1$-$C_4$ alkyl, $C_1$-$C_4$ alkoxy, $C_1$-$C_4$ haloalkyl, $C_1$-$C_6$ haloalkoxy, $C_2$-$C_6$ alkenyl, CN, $NO_2$, heteroaryl, and phenyl optionally substituted with any combination of one to five halogen, $NO_2$, CN, $C_1$-$C_4$ alkyl, $C_1$-$C_4$ haloalkyl, or $C_1$-$C_4$ alkoxy;
$R_4$, $R_5$, and $R_6$ are independently selected from the group consisting of H, hydroxyl, halogen, CN, $NO_2$, sulfonamide, $C_1$-$C_8$ alkyl, $C_3$-$C_6$ cycloalkyl, $C_1$-$C_6$ alkoxy, $C_1$-$C_4$ haloalkyl, $C_1$-$C_6$ haloalkoxy, $C_2$-$C_8$ alkenyl, amino, $C_1$-$C_4$ dialkyl amino, $C_1$-$C_4$ alkylamino, $C_3$-$C_6$ cycloalkylamino, morpholinyl, heteroaryl, arylamino, arylalkylamino, phenyl, and C(O)R', NR'(COR"), $NR'SO_2R''$ and NR'(CONR"R'"); wherein R', R" and R'" are independently H, $C_1$-$C_6$ alkyl, phenyl or substituted phenyl; and wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, arylamino, arylalkylamino, and morpholinyl; and the phenyl is optionally substituted with one or more members selected from the group consisting of halogen, $NO_2$, CN, $C_1$-$C_4$ alkyl, $C_1$-$C_4$ haloalkyl, and $C_1$-$C_4$ alkoxy;
$R_7$ is selected from the group consisting of H, CN, sulfonamide, $C_1$-$C_8$ alkyl, $C_3$-$C_6$ cycloalkyl, $C_1$-$C_6$ alkoxy, $C_1$-$C_4$ haloalkyl, $C_1$-$C_6$ haloalkoxy, $C_2$-$C_8$ alkenyl, $C_1$-$C_4$ dialkyl amino, $C_1$-$C_4$ alkylamino, $C_3$-$C_6$ cycloalkylamino, morpholinyl, heteroaryl, arylamino, arylalkylamino, phenyl, and C(O)R', NR'(COR"), $NR'SO_2R''$ and NR'(CONR"R'"); wherein R', R" and R'" are independently H, $C_1$-$C_6$ alkyl, phenyl or substituted phenyl; and wherein the $C_1$-$C_8$ alkyl is optionally substituted with one or more members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, arylamino, arylalkylamino, and morpholinyl; and the phenyl is optionally substituted with one or more members selected from the group consisting of halogen, $NO_2$, CN, $C_1$-$C_4$ alkyl, $C_1$-$C_1$ haloalkyl, and $C_1$-$C_1$ alkoxy;
or $R_4$ and $R_5$, $R_5$ and $R_6$, or $R_6$ and $R_7$ taken together with the carbon atoms to which they are attached form a dioxane or dioxolane ring;

X is selected from the group consisting of
H;
CN;
$C(O)NR_9R_{10}$ or $CH_2NR_9R_{10}$, wherein $R_9$ and $R_{10}$ are independently selected from the group consisting of H and $C_1$-$C_6$ alkyl, or $R_9$ and $R_{10}$ together with the nitrogen to which they are attached form a $C_5$-$C_6$ cycloalkyl ring or a heteroring such as morphline;
$CH_2OR_{11}$, wherein $R_{11}$ is H, $C_1$-$C_8$ alkyl, or $C_3$-$C_6$ cycloalkyl, wherein the $C_1$-$C_8$ alkyl optionally is substituted with one or members selected from the group consisting of $C_1$-$C_4$ alkoxy, $C_1$-$C_4$ haloalkyl, $C_1$-$C_6$ dialkyl amino, $C_1$-$C_6$ alkylamino, cycloalkylamino, and morpholinyl;
$CH_2Z$, wherein Z is halogen;
C(O)NHOH;
C(O)NHCN;
$C(O)N(R_1)SO_2R_{13}$, wherein $R_{13}$ is $C_1$-$C_4$ alkyl, phenyl, or substituted phenyl;
$C_1$-$C_8$ alkyl, optionally substituted with one or more members selected from the group consisting of $C_1$-$C_4$ alkoxy, haloalkyl, $C_1$-$C_6$ dialkylamino, and $C_1$-$C_6$ alkylamino; and
$C_2$-$C_8$ alkenyl optionally substituted with one or more members selected from the group consisting of $C_1$-$C_4$ alkoxy, $C_1$-$C_4$ haloalkyl, $C_1$-$C_6$ dialkylamino, and $C_1$-$C_6$ alkylamino;
wherein at least one of $R_4$, $R_5$, $R_6$ and $R_7$ is not H.

15. A compound of claim 14, wherein the compound is:

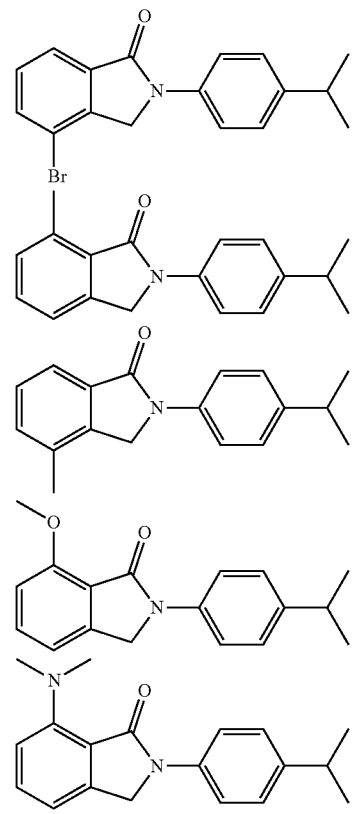

197
-continued
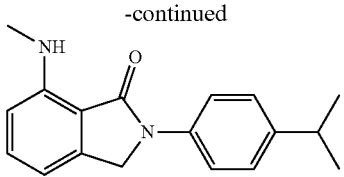
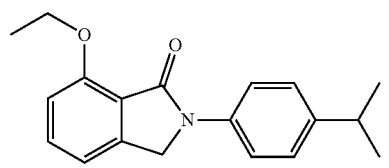
or
198
-continued
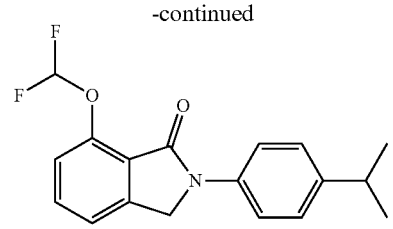
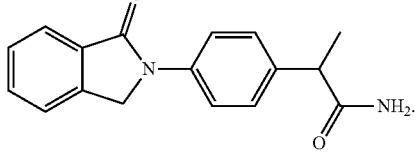
* * * * *